United States Patent
Walther et al.

(10) Patent No.: US 10,570,422 B2
(45) Date of Patent: Feb. 25, 2020

(54) METHOD FOR THE PREPARATION OF 2,4-DIHYDROXYBUTYRATE

(71) Applicant: ADISSEO FRANCE S.A.S., Antony (FR)

(72) Inventors: Thomas Walther, Lacroix-Falgarde (FR); Hélène Cordier, Labastidette (FR); Clémentine Dressaire, Toulouse (FR); Jean Marie Francois, Toulouse (FR); Robert Huet, Paris (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

(21) Appl. No.: 14/414,331

(22) PCT Filed: Jul. 10, 2013

(86) PCT No.: PCT/EP2013/064619
§ 371 (c)(1),
(2) Date: Jan. 12, 2015

(87) PCT Pub. No.: WO2014/009435
PCT Pub. Date: Jan. 16, 2014

(65) Prior Publication Data
US 2015/0147793 A1  May 28, 2015

Related U.S. Application Data

(60) Provisional application No. 61/670,405, filed on Jul. 11, 2012.

(51) Int. Cl.
| | |
|---|---|
| *C12P 7/42* | (2006.01) |
| *C12N 9/02* | (2006.01) |
| *C12N 9/04* | (2006.01) |
| *C12N 9/10* | (2006.01) |
| *C12N 9/12* | (2006.01) |
| *C12N 15/70* | (2006.01) |
| *C12N 1/21* | (2006.01) |
| *C12P 7/40* | (2006.01) |
| *C12P 7/52* | (2006.01) |

(52) U.S. Cl.
CPC ............. *C12P 7/42* (2013.01); *C12N 9/0006* (2013.01); *C12N 9/1096* (2013.01); *C12N 15/70* (2013.01); *C12Y 101/01027* (2013.01); *C12Y 101/01028* (2013.01); *C12Y 101/01037* (2013.01); *C12Y 101/01082* (2013.01); *C12Y 101/01272* (2013.01); *C12Y 101/01299* (2013.01); *C12Y 206/01001* (2013.01); *C12Y 206/01042* (2013.01); *C12Y 206/01057* (2013.01)

(58) Field of Classification Search
None
See application file for complete search history.

(56) References Cited

U.S. PATENT DOCUMENTS

| | | | | |
|---|---|---|---|---|
| 5,091,314 A * | 2/1992 | Marquardt | ........... | C12N 9/1096 435/108 |
| 8,900,838 B2* | 12/2014 | Soucaille | ................. | C12N 1/20 435/158 |

FOREIGN PATENT DOCUMENTS

WO  2012/056318 A1  5/2012

OTHER PUBLICATIONS

Arnold, F.H. 2001 Nature 409: 253-257.*
Bailey, J.E., 1991 Science 252(5013): 1668-1675. (Year: 1991).*
Keasling, J.D., 2010 Science 330(6009): 1355-1358. (Year: 2010).*
Yadav, V.G., et al. 2012 Metabolic Engineering 14: 233-241. (Year: 2012).*
Oue, S., et al. 1999 The Journal of Biological Chemistry 274(4): 2344-2349. (Year: 1999).*
Oct. 22, 2013 Search Report issued in International Application No. PCT/EP2013/064619.
Jan. 13, 2015 International Preliminary Report on Patentability issued in International Application No. PCT/EP2013/064619.
Roger S. Lane et al., "2-Keto-4-hydroxybutyrate. Synthesis, Chemical Properties, and as a Substrate for Lactate Dehydrogenase of Rabbit Muscle," Biochemistry, vol. 8, No. 7, Jul. 1969, pp. 2958-2966.
Dominique Madern, "Molecular Evolution Within the L-Malate and L-Lactate Dehydrogenase Super-Family," J. Mol. Evol. (2002), 54:825-840.
Arthur J. L. Cooper, "Asparagine Transaminase from Rat Liver," The Journal of Biological Chemistry, vol. 252, No. 6, 1977, pp. 2032-2038.
Madeleine Bouzon, et al., "A Synthetic Alternative to Canonical One-Carbon Metabolism," ACS Synth. Biol., 2017, pp. A-N.
T. Oshima et al., "Mechanism of Transaminase Action," Biochem J. (1961), 78, 116-119.

* cited by examiner

Primary Examiner — Marsha Tsay
(74) Attorney, Agent, or Firm — Oliff PLC

(57) ABSTRACT

A method for the preparation of 2,4-dihydroxybutyric acid from homoserine includes a first step of conversion of the primary amino group of homoserine to a carbonyl group to obtain 2-oxo-4-hydroxybutyrate, and a second step of reduction of the obtained 2-oxo-4-hydroxybutyrate (OHB) to 2,4-dihydroxybutyrate.

17 Claims, 3 Drawing Sheets
Specification includes a Sequence Listing.

METHOD FOR THE PREPARATION OF 2,4-DIHYDROXYBUTYRATE

The present invention relates to a novel method for the preparation of 2,4-dihydroxybutyrate (2,4-DHB) from homoserine comprising a two-step pathway:
- a first step of conversion of the primary amino group of homoserine to a carbonyl group to obtain 2-oxo-4-hydroxybutyrate, and
- a second step of reduction of the obtained 2-oxo-4-hydroxybutyrate (OHB) to obtain 2,4-DHB.

The carboxylic acids cited within the present application are equally named under their salt (e.g. 2,4-dihydroxybutyrate) or acid forms (e.g. 2,4-dihydroxybutyric acid).

2,4-dihydroxybutyric acid (equally 2,4-DHB or DHB) is a compound of considerable economic interest. DHB can be readily converted into α-hydroxy-γ-butyrolactone in aqueous media by adjusting the appropriate pH. α-hydroxy-γ-butyrolactone is a prominent precursor for the production of the methionine substitute 2-hydroxy-4-(methylthio)-butyrate (HMTB) (US 2009/318715) which has a large market in animal nutrition. At present, α-hydroxy-γ-butyrolactone is derived from γ-butyrolactone by a multi-stage process that implies halogenation of the γ-butyrolactone in position α, and subsequent substitution of the halogen atom by a hydroxyl group in alkaline medium (US 2009/318715).

From growing oil prices the need for the production of DHB from renewable resources arises. Microorganisms are capable of transforming biomass-derived raw material, e.g. sugars or organic acids, into a large variety of different chemical compounds (Werpy & Petersen, 2004). With the growing body of biochemical and genomic information it is possible to modify microorganisms such that they overproduce naturally occurring metabolic intermediates with high yield and productivity (Bailey, 1991). Optimization of production microorganisms often requires rational engineering of metabolic networks which ensures, among others, overexpression of enzymes required for the biosynthesis of the metabolite of interest, and alleviation of product feedback inhibition. Another possibility is the implementation of novel enzymatic systems that catalyze the production of a metabolite of interest.

Metabolic engineering approaches and enzymatic catalyses require detailed knowledge of the biochemistry and regulation of the metabolic pathway leading to the metabolite of interest. In the case of DHB production, this information is not available. Only few studies report the occurrence of DHB in patients with succinic semialdehyde dehydrogenase deficiency (Shinka et al., 2002) without, however, identifying enzymatic reactions implicated in DHB production. The zymotic or enzymatic production of DHB, therefore, requires (i) the identification of a thermodynamically feasible pathway which transforms an accessible precursor into DHB, (ii) the identification or construction of enzymes that are capable to catalyze individual reaction steps in the pathway and (iii) the functional expression of the pathway enzymes in an appropriate production organism. The present invention has as an objective to satisfy these needs.

Accordingly, one object of the present invention is a method of preparation of 2,4-DHB from homoserine comprising a two-step pathway (see FIG. 1):
- a first step of conversion of the primary amino group of homoserine to a carbonyl group to obtain OHB, and
- a second step of reduction of the obtained OHB to 2,4-DHB.

The first and/or the second step(s) of the method of the invention can be catalyzed either by an enzyme encoded by an endogenous or a heterologous gene.

In the description, enzymatic activities are also designated by reference to the genes coding for the enzymes having such activity. The use of the denomination of the genes is not limited to a specific organism, but covers all the corresponding genes and proteins in other organisms (e.g. microorganisms, functional analogues, functional variants and functional fragments thereof as long as they retain the enzymatic activity).

Within a further aspect of the invention, the enzyme converting the primary amino group of homoserine to a carbonyl group to obtain OHB can be homoserine transaminase, homoserine dehydrogenase, or homoserine oxidase.

Within a further aspect of the invention, the enzyme having homoserine transaminase activity can be identified among enzymes having aspartate transaminase (EC2.6.1.1) activity, branched-chain-amino-acid transaminase (EC2.6.1.42) activity, or aromatic-amino-acid transaminase (EC2.6.1.57) activity.

Within a further aspect of the invention, the homoserine transaminase can be the branched-chain-amino-acid transaminase from *Escherichia coli*, Ec-IlvE, and *Lactococcus lactis*, Ll-BcaT, the aromatic-amino-acid transaminases from *E. coli*, Ec-TyrB, *L. lactis*, Ll-AraT, and *Saccharomyces cerevisiae*, Sc-Aro8, or the aspartate transaminase from *E. coli*, Ec-AspC.

The second step of the method of the present invention is catalysed by an enzyme having OHB reductase activity. Within a further aspect of the invention, the enzyme having OHB reductase activity can be identified among enzymes having 2-hydroxyacid dehydrogenase activity, in particular among enzymes having lactate dehydrogenase (Ldh) (EC1.1.1.27, EC1.1.1.28), malate dehydrogenase (Mdh) (EC1.1.1.37, EC1.1.1.82, EC1.1.1.299) activity, or branched chain (D)-2-hydroxyacid dehydrogenase (EC1.1.1.272, EC1.1.1.345) activity. More specifically, the enzyme having homoserine transaminase activity is encoded by genes ilvE, tyrB, aspC, araT, bcaT, or ARO8.

In an even more specific aspect, the enzyme having homoserine transaminase activity is encoded by sequence set forth in SEQ ID No. 59, SEQ ID No. 61, SEQ ID No. 63, SEQ ID No. 65, SEQ ID No. 67 or SEQ ID No. 69 or any sequence sharing a homology of at least 50% with said sequences or corresponds to SEQ ID No. 60, SEQ ID No. 62, SEQ ID No. 64, SEQ ID No. 66, SEQ ID No. 68, SEQ ID No. 70 or any sequence sharing a homology of at least 50% with said sequences.

Within a further aspect of the invention, the OHB reductase enzyme can be the (L)-lactate dehydrogenase from *Lactococcus lactis* (Ll-LdhA), from *Oryctalagus cuniculus* (Oc-LldhA), from *Geobacillus stearothermophilus* (Gs-Lldh), or from *Bacillus subtilis* (Bs-Ldh), the (D)-lactate dehydrogenase from *Escherichia coli* (Ec-LdhA), the (L)-malate dehydrogenase from *Escherichia coli* (Ec-Mdh), or the branched chain (D)-2-hydroxyacid dehydrogenase from *Lactococcus lactis* (Ll-PanE).

In an even more specific aspect of the invention the OHB reductase enzyme is represented by the amino acid sequences SEQ ID No. 2, SEQ ID No. 4, SEQ ID No. 6, SEQ ID No. 8, SEQ ID No. 10, SEQ ID No. 12, SEQ ID No. 14, SEQ ID No. 288, SEQ ID No. 30, SEQ ID No. 32, SEQ ID No. 102, SEQ ID No. 104, SEQ ID No. 106, SEQ ID No. 108, SEQ ID No. 110, SEQ ID No. 112, SEQ ID No. 114, SEQ ID No. 116 or SEQ ID No. 118 or any sequence sharing a homology of at least 50% with said sequences, or is encoded by the nucleic acid sequences represented by SEQ ID No. 1, SEQ ID No. 3, SEQ ID No. 5, SEQ ID No. 7, SEQ ID No. 9, SEQ ID No. 11, SEQ ID No. 13, SEQ ID No. 287, SEQ ID No. 29, SEQ ID No. 31, SEQ ID No. 101, SEQ ID No. 103, SEQ ID No. 105, SEQ ID No. 107, SEQ ID No. 109, SEQ ID No. 111, SEQ ID No. 113, SEQ ID No. 115 or SEQ ID No. 117 or any sequence sharing a homology of at least 50% with said sequences.

In a further aspect, the invention also deals with the use of an enzyme reducing OHB to 2,4-DHB as above described.

Proteins sharing substantial homology with the above enzymes are also another aspect of the invention such as functional variants or functional fragments.

The expression "substantial homology" covers homology with respect to structure and/or amino acid components and/or biological activity.

More generally, within the meaning of the invention the homology between two protein sequences can be determined by methods well known by the skilled man in the art. It is generally defined as a percentage of sequence identity between a reference sequence and the sequence of a protein of interest.

As used herein, "percent (%) sequence identity" with respect to the amino acid or nucleotide sequences identified herein is defined as the percentage of amino acid residues or nucleotides in a candidate sequence that are identical with the amino acid residues or nucleotides in an enzyme sequence, after aligning the sequences and introducing gaps, if necessary, to achieve the maximum percent sequence identity, and not considering any conservative substitutions as part of the sequence identity. Methods for performing sequence alignment and determining sequence identity are known to the skilled artisan, may be performed without undue experimentation, and calculations of identity values may be obtained with definiteness. See, for example, Ausubel, et al., eds. (1995) Current Protocols in Molecular Biology, Chapter 19 (Greene Publishing and Wiley-Interscience, New York); and the ALIGN program (Dayhoff (1978) in Atlas of Protein Sequence and Structure 5:Suppl. 3 (National Biomedical Research Foundation, Washington, D.C.). A number of algorithms are available for aligning sequences and determining sequence identity and include, for example, the homology alignment algorithm of Needleman et al. (1970) J. Mol. Biol. 48:443; the local homology algorithm of Smith, et al. (1981) Adv. Appl. Math. 2:482; the search for similarity method of Pearson, et al. (1988) Proc. Natl. Acad. Sci. 85:2444; the Smith-Waterman algorithm (Meth. Mol. Biol. 70:173-187 (1997); and BLASTP, BLASTN, and BLASTX algorithms (see Altschul, et al. (1990) J. Mol. Biol. 215:403-410). Computerized programs using these algorithms are also available, and include, but are not limited to: ALIGN or Megalign (DNASTAR) software, or WU-BLAST-2 (Altschul, et al., Meth. Enzym., 266:460-480 (1996)); or GAP, BESTFIT, BLAST (Altschul, et al.), supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can be determined by the Smith-Waterman homology search algorithm (Meth. Mol. Biol. 70:173-187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum62 amino acid substitution matrix, with a gap weight of 12 and a length weight of 2. With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for increased sequence identity associated with inclusion of gaps in the derivative's amino acid sequence can be made by assigning gap penalties.

The enzymes according to the present invention having the same activity (either OHB reductase, or the enzyme converting the primary amino group of homoserine to a carbonyl group to obtain OHB) share at least about 50%, 70% or 85% amino acid sequence identity, preferably at least about 85% amino acid sequence identity, more preferably at least about 90% amino acid sequence identity, even more preferably at least about 95% amino acid sequence identity and yet more preferably 98% amino acid sequence identity. Preferably, any amino acid substitutions are "conservative amino acid substitutions" using L-amino acids, wherein one amino acid is replaced by another biologically similar amino acid. Conservative amino acid substitutions are those that preserve the general charge, hydrophobicity/hydrophilicity, and/or steric bulk of the amino acid being substituted. Examples of conservative substitutions are those between the following groups: Gly/Ala, Val/Ile/Leu, Lys/Arg, Asn/Gln, Glu/Asp, Ser/Cys/Thr, and Phe/Trp/Tyr. A derivative may, for example, differ by as few as 1 to 10 amino acid residues, such as 6-10, as few as 5, as few as 4, 3, 2, or even 1 amino acid residue.

The term functional variant encompasses enzymes that may present substantial sequence modifications when compared to the sequences specifically described within the present application but that still retain the original enzymatic activity.

It also means that the sequence of the enzyme may comprise less amino acids than the original one but said truncated enzyme still retains the original enzymatic activity.

According to an aspect of the invention, the activity of the enzyme catalyzing the first and/or the second step of the method of the present invention is enhanced. This enhancement can be measured by an enzymatic assay as described in Examples 1 or 4.

Improvement of said enzymes can be obtained by at least one mutation, said mutation(s) (i) improving the activity and/or substrate affinity of the mutated enzyme for homoserine or OHB respectively, and or (ii) decreasing the activity and/or substrate affinity of the mutated enzyme for their natural substrate.

Within the present invention, the expression "improve the activity and/or substrate affinity" means that the enzyme before mutation, was either
  unable to use the substrate, and/or
  synthesized the product of the reaction at a maximum specific rate at least three times lower, and/or
  had an affinity for homoserine or OHB that was at least three times lower, and/or.

had a maximum specific activity on the natural substrate that was at least three times higher, and/or.

had an affinity for the natural substrate that was at least three times higher.

In a still further aspect the invention encompasses the nucleotide sequences encoding the enzymes catalyzing the first and the second step of the method of the invention.

In an even more specific aspect of the invention the OHB reductase enzyme is encoded by the nucleic acid sequences represented by SEQ ID No. 1, SEQ ID No. 3, SEQ ID No. 5, SEQ ID No. 7, SEQ ID No. 9, SEQ ID No. 11, SEQ ID No. 13, SEQ ID No. 287, SEQ ID No. 29, SEQ ID No. 31, SEQ ID No. 101, SEQ ID No. 103, SEQ ID No. 105, SEQ ID No. 107, SEQ ID No. 109, SEQ ID No. 111, SEQ ID No. 113, SEQ ID No. 115 or SEQ ID No. 117 or any sequence sharing a homology of at least 50% with said sequences.

The OHB reductase according to the invention corresponds in a specific aspect to (L)-lactate dehydrogenase A comprising at least one mutation when a compared to the wild type enzyme in at least one of the positions V17, Q85, E89, I226, or A222. These positions are conserved in the lactate dehydrogenase family, and they are defined in this text by reference to the *Lactococcus lactis* (L)-lactate dehydrogenase A (SEQ ID No. 6). The skilled man in the art will then easily identify the corresponding amino acid residues in other lactate dehydrogenases by an alignment of the corresponding amino acid sequences. Therefore, the invention also provides for changes of these amino acids in other lactate dehydrogenase enzymes.

The OHB reductase according to the invention corresponds in a specific aspect to (L)-malate dehydrogenase comprising at least one mutation when compared to the wild type enzyme in at least one of the positions I12, R81, M85, D86, V93, G179, T211, or M227. These positions are conserved in the malate dehydrogenase family, and they are defined in this text by reference to the sequence of the *E. coli* (L)-malate dehydrogenase (SEQ ID No. 2). The man skilled in the art will easily identify the corresponding amino acid residues in other malate dehydrogenases by an alignment of the corresponding amino acid sequences. Therefore, the invention also provides for changes of these amino acids in other malate dehydrogenase enzymes.

In accordance with this invention, a "nucleic acid sequence" refers to a DNA or RNA molecule in single or double stranded form, preferably a DNA molecule. An "isolated DNA", as used herein, refers to a DNA which is not naturally-occurring or no longer in the natural environment wherein it was originally present, e.g., a DNA coding sequence associated with other regulatory elements in a chimeric gene, a DNA transferred into another host cell, or an artificial, synthetically-made DNA sequence having a different nucleotide sequence compared to any naturally-occurring DNA sequence.

The present invention also relates to a chimeric gene comprising, functionally linked to one another, at least one promoter which is functional in a host organism, a polynucleotide encoding anyone of the enzymes catalyzing first and second step of the method as defined according to the invention, and a terminator element that is functional in the same host organism. The various elements which a chimeric gene may contain are, firstly, elements regulating transcription, translation and maturation of proteins, such as a promoter, a sequence encoding a signal peptide or a transit peptide, or a terminator element constituting a polyadenylation signal and, secondly, a polynucleotide encoding a protein. The expression "functionally linked to one another" means that said elements of the chimeric gene are linked to one another in such a way that the function of one of these elements is affected by that of another. By way of example, a promoter is functionally linked to a coding sequence when it is capable of affecting the expression of said coding sequence. The construction of the chimeric gene according to the invention and the assembly of its various elements can be carried out using techniques well known to those skilled in the art. The choice of the regulatory elements constituting the chimeric gene depends essentially on the host organism in which they must function, and those skilled in the art are capable of selecting regulatory elements which are functional in a given host organism. The term "functional" is intended to mean capable of functioning in a given host organism.

The promoters which the chimeric gene according to the invention may contain are either constitutive or inducible. By way of example, the promoters used for expression in bacteria may be chosen from the promoters mentioned below. For expression in *Escherichia coli* mention may be made of the lac, trp, lpp, phoA, recA, araBAD, prou, cst-I, tetA, cadA, nar, tac, trc, lpp-lac, Psyn, cspA, PL, PL-9G-50, PR-PL, T7, [lambda]PL-PT7, T3-lac, T5-lac, T4 gene 32, nprM-lac, VHb and the protein A promoters or else the Ptrp promoter (WO 99/64607). For expression in Gram-positive bacteria such as *Corynebacteria* or *Streptomyces*, mention may be made of the PtipA or PS1 and PS2 (FR91/09870) promoters or those described in application EP0629699A2. For expression in yeasts and fungi, mention may be made of the *K. lactis* PLAC4 promoters or the *K. lactis* Ppgk promoter (patent application FR 91/05294), the *Trichoderma reesei* tef1 or cbh1 promoter (WO 94/04673), the *Penicillium funiculosum* his, csl or apf promoter (WO 00/68401) and the *Aspergillus niger* gla promoter.

According to the invention, the chimeric gene may also comprise other regulatory sequences, which are located between the promoter and the coding sequence, such as transcription activators (enhancers).

As such, the chimeric gene of the invention comprises in a specific embodiment at least, in the direction of transcription, functionally linked, a promoter regulatory sequence which is functional in a host organism, a nucleic acid sequence encoding a polynucleotide encoding anyone of the enzymes catalyzing first and second step of the method as defined according to the invention and a terminator regulatory sequence which is functional in said host organism.

The present invention also relates to a cloning and/or expression vector comprising a chimeric gene according to the invention or a nucleic acid sequence of the invention. The vector according to the invention is of use for transforming a host organism and expressing in this organism anyone of the enzymes catalyzing the first and/or the second step(s) of the method of the present invention. This vector may be a plasmid, a cosmid, a bacteriophage or a virus. Preferentially, the transformation vector according to the invention is a plasmid. Generally, the main qualities of this vector should be able to maintain itself and to self-replicate in the cells of the host organism, in particular by virtue of the presence of an origin of replication, and to express anyone of the enzymes catalyzing the first and/or the second step(s) of the method of the present invention therein. For the purpose of stable transformation of a host organism, the vector may also integrate into the genome. The choice of such a vector, and also the techniques of insertion of the chimeric gene according to the invention into this vector are part of the general knowledge of those skilled in the art. Advantageously, the vector used in the present invention also contains, in addition to the chimeric gene according to the invention, a chimeric gene encoding a selectable marker. This selectable marker makes it possible to select the host organisms which are effectively transformed, i.e. those which incorporated the vector. According to a particular embodiment of the invention, the host organism to be transformed is a bacterium, a yeast, a fungus. Among the selectable markers which can be used, mention may be made of markers containing genes for resistance to antibiotics, such as, for example, the hygromycinphosphotransferase gene. Other markers may be genes to complement an auxotrophy, such as the pyrA, pyrB, pyrG, pyr4, arg4, argB and trpC genes, the molybdopterin synthase gene or that of acetamidase. Mention may also be made of genes encoding readily identifiable enzymes such as the GUS enzyme, or genes encoding pigments or enzymes regulating the production of pigments in the transformed cells. Such selectable marker genes are in particular described in patent applications WO 91/02071, WO 95/06128, WO 96/38567 and WO 97/04103.

The present invention also relates to modified microorganisms.

More specifically, the modified microorganism of the invention allows the preparation of 2,4-DHB from homoserine by a two-step pathway comprising:
  a first step of conversion of the primary amino group of homoserine to a carbonyl group to obtain 2-oxo-4-hydroxybutyrate, and
  a second step of reduction of the obtained 2-oxo-4-hydroxybutyrate to obtain 2,4-dihydroxybutyrate.

The enzymes involved in the two steps are those above described.

The term "microorganism" is intended to mean any lower unicellular organism into which the chimeric gene(s), nucleic acid(s) or vector(s) according to the invention may be introduced in order to produce 2,4-DHB. Preferably, the host organism is a microorganism, in particular a fungus, for example of the *Penicillium, Aspergillus* and more particularly *Aspergillusflavus, Chrysosporium* or *Trichoderma* genus, a yeast, in particular of the Saccharomycetaceae, Pichiaceae or Schizosaccharomycetaceae, most preferentially *Saccharomyces cerevisiae, Schizosaccharomyces pombe, Kluyveromyces lactis, Kluyveromyces marxianus*, or *Pichia jadinii, Pichia stipitis* or *Pichia pastoris*, a bacterium, preferentially selected among Enterobacteriaceae, Clostridiaceae, Bacillaceae, Streptomycetaceae, Streptococcaceae, Methylobacteriacae, and Corynebacteriaceae, most preferentially *Escherichia coli, Bacillus subtilis, Corynebacterium glutamicum, Clostridium acetobutylicum, Methylobacterium extorquens* or *Lactococcus lactis*.

The present invention also relates to modified microorganisms containing at least one chimeric gene according to the invention, either integrated into their genome or carried on an extra-chromosomal genetic element, for example a plasmid. In a more specific aspect of the invention, the transformed host organism comprises a nucleic acid of the invention encoding a polypeptide converting the primary amino acid group of homoserine to a carbonyl group to obtain OHB and/or a nucleic acid encoding a polypeptide reducing OHB in 2,4-DHB or a chimeric gene comprising a nucleic acid encoding a polypeptide converting the primary amino acid group of homoserine to a carbonyl group to obtain OHB, and/or a OHB reductase or an expression vector comprising a nucleic acid encoding a polypeptide converting the primary amino group of homoserine to a carbonyl group to obtain OHB, or a polypeptide having a OHB reductase activity.

Within a further aspect of the invention, the synthetic pathway for the conversion of homoserine into DHB is expressed in a microorganism with enhanced production of homoserine. Enhanced production of homoserine in microorganisms can be achieved by (i) overexpressing the enzymes aspartate kinase, aspartate semialdehyde dehydrogenase, and homoserine dehydrogenase, (ii) by rendering the aspartate kinase enzyme insensitive to product inhibition that can be brought about by lysine, methionine, or threonine, and (iii) by deletion of metabolic pathways that branch off the homoserine biosynthesis pathway. Overexpression of aspartate kinase, aspartate semialdehyde dehydrogenase, and homoserine dehydrogenase can be achieved by expressing the enzymes from a multicopy plasmid under the control of an appropriate constitutive or inducible promoter. Alternatively, overexpression of said enzymes can be achieved by deletion of transcriptional repressors that limit the transcription of genes coding for aspartate kinase, aspartate semialdehyde dehydrogenase, and homoserine dehydrogenase. Aspartate kinases can be rendered insensitive to inhibition by aspartate-derived amino acids by introducing appropriate mutations into their amino acid sequences. Entry points into metabolic pathways that branch off the homoserine biosynthesis pathway are catalyzed by enzymes having O-succinyl homoserine or O-acetyl homoserine synthase activity (entry into methionine biosynthesis), homoserine kinase activity (entry into threonine biosynthesis), or diaminopimelate decarboxylase activity (entry into lysine biosynthesis). Deletion of genes encoding proteins having said enzymatic activities avoids formation aspartate-derived amino acids and therefore aids homoserine formation.

Accordingly, deletion of the genes metA, thrB, and lysA in *E. coli* attenuates pathways that branch of the homoserine biosynthetic pathway. The increase of enzymatic activities of the homoserine pathway in *E. coli* can be achieved, for instance, by the overexpression of the bifunctional aspartate kinase-homoserine dehydrogenase mutant thrA S345F (insensitive to threonine inhibition) and asd (both genes from *E. coli*); or by the overexpression of the monofunctional aspartate kinase mutant lysC E250K (insensitive to lysine), asd (both genes from *E. coli*), and the homoserine dehydrogenase gene HOM6 from *S cerevisiae*.

The microorganism of the invention may also have attenuated capacity to export homoserine which increases the intracellular availability of this amino acid. In order to achieve decreased homoserine export from the cells, permeases capable of exporting homoserine can be deleted. Such permeases may be identified by overexpressing genomic libraries in the microorganism and cultivating said microorganism at inhibitory concentrations of homoserine or structurally similar amino acids such as threonine, leucine, or aspartate (Zakataeva et al. 1999/FEBS Lett/452/228-232). Genes whose overexpression confers growth at increased concentrations of either of said amino acids are likely to participate in homoserine export.

In a further aspect, the microorganism of the invention being *Escherichia coli* carries deletions in the homoserine efflux transporters rhtA, rhtb, and/or rhtC.

Efficient production of DHB can be ensured by optimizing carbon flux repartitioning in the metabolic network of the host organism with respect to the optimization of cofactor supply for DHB synthesis, and attenuation of competing pathways that cause formation of metabolic by-products other than DHB. An important tool for strain improvement provides constraint-based flux balance analysis. This method allows calculating the theoretical yield of a given metabolic network depending on cultivation conditions, and facilitates identification of metabolic targets for overexpression or deletion. The experimental techniques used for overexpression and deletion of the metabolic target reaction are described (Example 8).

Accordingly, the microorganism of the invention may also exhibit enzymatic activities chosen among phosphoenolpyruvate carboxylase, phosphoenolpyruvate carboxykinase, isocitrate lyase, pyruvate carboxylase, and hexose symporter permease which is increased, and/or at least one of the enzymatic activities chosen among lactate dehydrogenase, alcohol dehydrogenase, acetate kinase, phosphate acetyltransferase, pyruvate oxidase, isocitrate lyase, fumarase, 2-oxoglutarate dehydrogenase, pyruvate kinase, malic enzyme, phosphoglucose isomerase, phosphoenolpyruvate carboxylase, phosphoenolpyruvate carboxykinase, pyruvate-formate lyase, succinic semialdehyde dehydrogenase, sugar-transporting phosphotransferase, ketohydroxyglutarate aldolase, homoserine-O-succinyl transferase, homoserine kinase, homoserine efflux transporter, diaminopimelate decarboxylase, and/or methylglyoxal synthase which is (are) decreased.

In a further aspect, the microorganism of the invention being *Escherichia coli* overexpresses at least one of the genes chosen among ppc, pck, aceA, galP, asd, thrA, metL, lysC all *E. coli*; pycA from *L. lactis*, and/or has at least one of the genes deleted chosen among ldhA, adhE, ackA, pta, poxB, focA, pflB, sad, gabABC, sfcA, maeB, ppc, pykA, pykF, mgsA, sucAB, ptsI, ptsG, pgi, fumABC, aldA, lldD, icIR, metA, thrB, lysA, eda, rhtA, rhtB, rhtC.

The present invention also encompasses a method of production of 2,4-DHB comprising the steps of
culturing the modified microorganism of the invention in an appropriate culture medium,
recovering 2,4-DHB from the culture medium.
Said 2,4-DHB can be further purified.

Product separation and purification is very important factor enormously affecting overall process efficiency and product costs. Methods for product recovery commonly comprise the steps cell separation, as well as product purification, concentration and drying, respectively.

Cell Separation

Ultrafiltration and centrifugation can be used to separate cells from the fermentation medium. Cell separation from fermentation media is often complicated by high medium viscosity. Therefore, we can add additives such as mineral acids or alkali salts, or heating of the culture broth to optimize cell separation.

Product Recovery

A variety of ion-exchange chromatographic methods can be applied for the separation of DHB either before or after biomass removal. They include the use of primary cation exchange resins that facilitate separation of products according to their isoelectric point. Typically, the resin is charged with the solution, and retained product is eluted separately following increase of pH (e.g. by adding ammonium hydroxide) in the eluent. Another possibility is the use of ion-exchange chromatography using fixed or simulated moving bed resins. Different chromatographic steps may have to be combined in order to attain adequate product purity. Those purification methods are more economical compared with a costly crystallization step, also providing additional advantages and flexibility regarding the form of final product.

Product Concentration and Drying

The purification process can also comprise a drying step which may involve any suitable drying means such as a spray granulator, spray dryer, drum dryer, rotary dryer, and tunnel dryer. Concentrated DHB solutions can be obtained by heating fermentation broths under reduced pressure by steam at 130° C. using a multipurpose concentrator or thin film evaporator.

Figure 1:
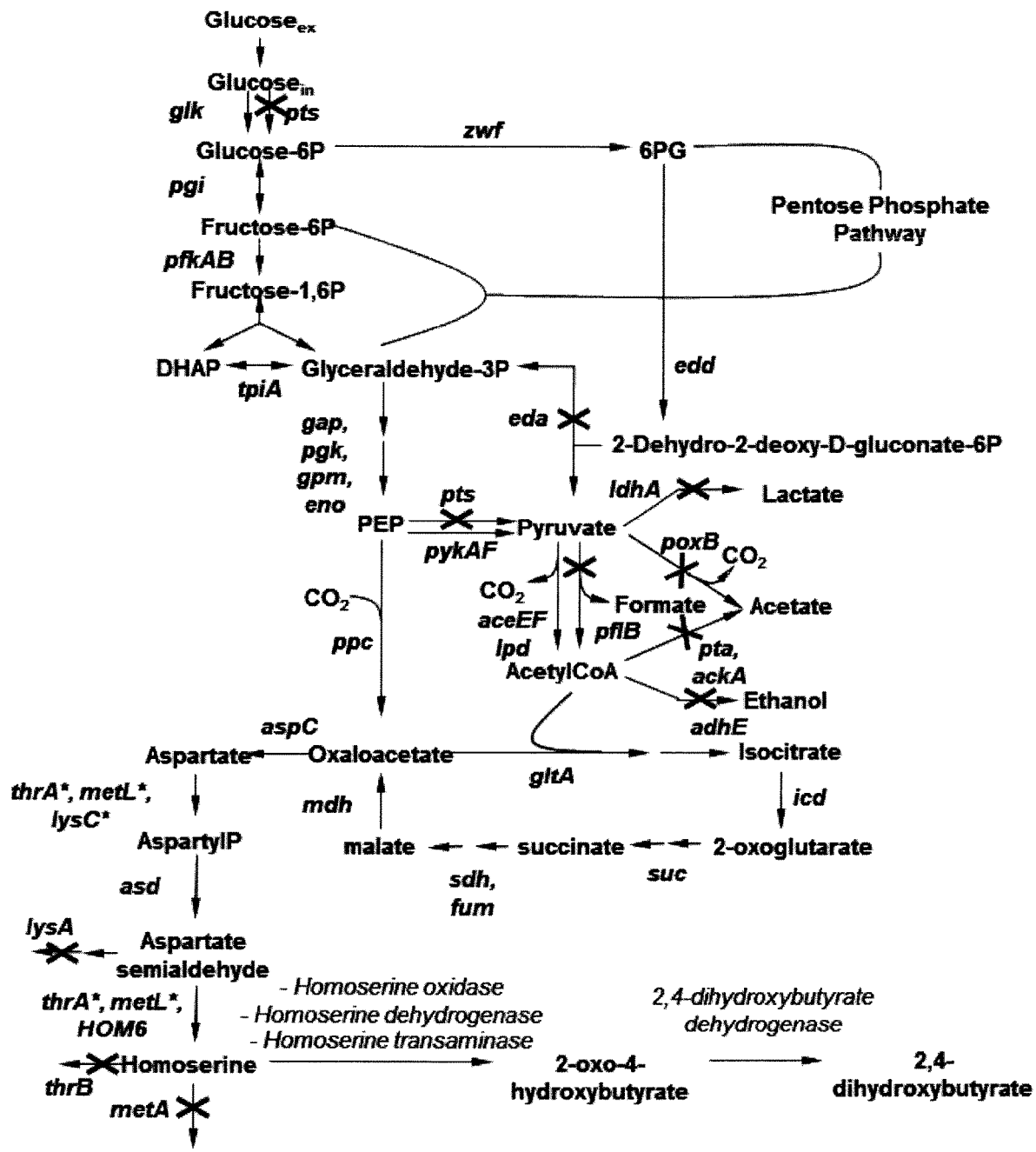
FIG. 1: Method of preparation of 2,4-DHB from homoserine comprising a two step pathway which employs a first step of conversion of the primary amino group of homoserine to a carbonyl group to obtain OHB, and a second step of reduction of the obtained OHB to 2,4-DHB.

The following non limiting examples illustrate the invention.

EXAMPLES

Example 1: Demonstration of OHB Reductase Activity

Construction of Plasmids Containing Wild-Type Genes Coding for Lactate Dehydrogenase or Malate Dehydrogenase:

The genes coding for (L)-malate dehydrogenase in *Escherichia coli*, Ec-mdh (SEQ ID No. 1), (D)-lactate dehydrogenase in *E. coli*, Ec-ldhA (SEQ ID No. 3), (L)-lactate dehydrogenase of *Lactococcus lactis*, Ll-ldhA (SEQ ID No. 5), (L)-lactate dehydrogenase of *Bacillus subtilis*, Bs-ldh (SEQ ID No. 7), (L)-lactate dehydrogenase of *Geobacillus stearothermophilus*, Gs-ldh (SEQ ID No. 9), the two isoforms of the (L)-lactate dehydrogenase of *Oryctalagus cuniculus*, Oc-ldhA (SEQ ID No. 11 and SEQ ID No. 13), were amplified by PCR using the high-fidelity polymerase Phusion™ (Fermentas) and the primers listed in Table 1. Genomic DNAs of *E. coli* MG1655, *L. Lactis* IL1403, and *B. subtilis* strain 168 were used as the template. The genes Oc-ldhA, and Gs-ldh were codon-optimized for expression in *E. coli* and synthesized by MWG Eurofins. The primers introduced restriction sites (Table 1) upstream of the start codon and downstream of the stop codon, respectively, facilitating the ligation of the digested PCR products into the corresponding sites of the pET28a+ (Novagen) expression vector using T4 DNA ligase (Fermentas). Ligation products were transformed into *E. coli* DH5α cells (NEB). The resulting pET28-Ec-mdh, pET28-Ec-ldhA, pET28-Ll-ldhA, pET28-Bs-ldh, pET28-Gs-ldh, and pET28-Oc-ldhA plasmids were isolated and shown by DNA sequencing to contain the correct full-length sequence of the *E. coli* mdh, *E. coli* ldhA, *L. lactis* ldhA, *B. subtilis* ldh, *G. stearothermophilus* ldh, and *O. cuniculus* ldhA genes, respectively. The corresponding protein sequences are represented by SEQ ID No. 2, SEQ ID No. 4, SEQ ID No. 6, SEQ ID No. 8, SEQ ID No. 10, SEQ ID No. 12 and SEQ ID No. 14, respectively.

TABLE 1

Primer sequences and restriction sites used for amplification and cloning of candidate enzymes

| Gene | Forward and reverse primer sequence 5' - 3' | Restriction sites |
|---|---|---|
| Ec-mdh | TATAATCATATGAAAGTCGCAGTCCTC (SEQ ID No 15). | NdeI |
|  | TATAATGGATCCTTACTTATTAACGAACTC (SEQ ID No. 16) | BamHI |
| Ll-ldhA | TATAATCATATGGCTGATAAACAACGTAAAAAA (SEQ ID No. 17) | NdeI |
|  | TATAATGGATCCTTAGTTTTTAACTGCAGAAGCAAA (SEQ ID No. 18) | BamHI |
| Bs_ldh | TATAATGCTAGCATGATGAACAAACATGTAAATAAAGT (SEQ ID No. 19) | NdeI |
|  | TATAATGGATCCTTAGTTGACTTTTTGTTC (SEQ ID No. 20) | BamHI |
| Gs-ldh | Gene was delivered by MWG Eurofins™ in pET28a vector | NdeI BamHI |
| Oc-ldhA | TATAATGCTAGCATGGCGGCGTTGAAAGAC (SEQ ID No. 21) | NheI |
|  | ATTATAGAATTCTTAAAATTGCAGTTCTTT (SEQ ID No. 22) | EcoRI |
| Ll-panE | TATAATCATATGAGAATTACAATTGCCGG (SEQ ID No. 23) | NdeI |
|  | TATAATGGATCCTTATTTTGCTTTTAATAACTCTTCTTTGC (SEQ ID No. 24) | BamHI |
| Ec-ldhA | TATAATCATATGAAACTCGCCGTTTATAG (SEQ ID No. 25) | NdeI |
|  | TATAATGGATCCTTAAACCAGTTCGTTCGG (SEQ ID No. 26) | BamHI |

Expression of Enzymes:

*E. coli* BL21 (DE3) star cells were transformed with the appropriate plasmids using standard genetic protocols (Sambrook, Fritsch, & Maniatis, 1989). Enzymes with an N-terminal hexa-His tag were expressed in 50 mL LB cultures that were inoculated from an overnight culture at $OD_{600}$ of 0.1 and grown to $OD_{600}$ of 0.6 before protein expression was induced by addition of 1 mM isopropyl β-D-1-thiogalactopyranoside (IPTG) to the culture medium. After 15 h of protein expression, cells were harvested by centrifugation at 4000 g at 4° C. for 10 min and discarding the supernatant. Cell pellets were stored at −20° C. until further analysis. Growth and protein expression were carried out at 25° C. Culture media contained 50 μg/mL kanamycin.

Purification of Enzymes:

Frozen cell pellets of expression cultures were resuspended in 0.5 mL of breakage buffer (50 mM Hepes, 300 mM NaCl, pH 7.5) and broken open by four successive rounds of sonication (sonication interval: 20 s, power output: 30%, sonicator: Bioblock Scientific, VibraCell™ 72437). Cell debris was removed by centrifuging the crude extracts for 15 min at 4° C. at 4000 g and retaining the clear supernatant. RNA and DNA were removed from the extracts by adding 15 mg/mL streptomycin sulfate (Sigma), centrifuging the samples at 13000 g for 10 min at 4° C. and retaining the supernatant. Clear protein extract was incubated for 1 h at 4° C. with 0.75 mL (bed volume) of Talon™ Cobalt affinity resin (Clontech). The suspension was centrifuged at 700 g in a table top centrifuge and supernatant was removed. The resin was washed with 10 bed volumes of wash buffer (50 mM Hepes, 300 mM NaCl, 15 mM Imidazole, pH 7.5) before proteins were eluted with 0.5 mL of elution buffer (50 mM Hepes, 300 mM NaCl, 250 mM Imidazole, pH 7.5). Purity of eluted enzymes was verified by SDS-PAGE analysis. Protein concentrations were estimated with the method of Bradford (Bradford (1976, Anal. Biochem. 72: 248-54). To stabilize the lactate dehydrogenase enzymes, the elution buffer was systematically exchanged by 100 mM phosphate buffer adjusted to pH 7. The protein sample was transferred to an Amicon™ Ultra centrifugal filter (cut-off 10 kDa), and centrifuged during 8 min at 4000 g at 4° C. to remove the buffer. The protein was diluted into phosphate buffer and the procedure was repeated 4 times.

Enzymatic Assays:

The reaction mixture contained 60 mM Hepes (pH 7), 50 mM potassium chloride, 5 mM $MgCl_2$, 0.25 mM NADH, (optionally 5 mM fructose-1,6-bisphosphate) (all products from Sigma), and appropriate amounts of purified malate or lactate dehydrogenase or cell extract. Reactions were started by adding appropriate amounts of 2-oxo-4-hydroxybutyrate (OHB), pyruvate, or oxaloacetate (OAA). Enzymatic assays were carried out at 37° C. in 96-well flat bottomed microtiter plates in a final volume of 250 μL. The reactions were followed by the characteristic absorption of NADH at 340 nm ($\varepsilon_{NADH}$=6.22 $mM^{-1}$ $cm^{-1}$) in a microplate reader (Bio-Rad 680XR).

OHB was synthesized by incubating 125 mM homoserine with snake venom (L)-amino acid oxidase (1.25 U/mL, Sigma) and catalase (4400 U/mL, Sigma) in 100 mM Tris buffer at pH 7.8 for 90 min at 37° C. Subsequently, the reaction mixture was purified on an Amicon™ Ultra centrifugal filter with a cut-off of 10 kDa to eliminate the enzymes (method adapted from Wellner & Lichtenberg, 1971).

OHB was quantified by mixing 100 µL of the tested solution with 1 mL of a solution containing 1 M sodium arsenate and 1 M boric acid at pH 6.5. The mixture was incubated at room temperature for 30 min and the absorbance at 325 nm was used to quantify OHB. The relation between absorbance and concentration of the ketone was calibrated using pyruvate solutions of known concentrations (method adapted from (Wellner & Lichtenberg, 1971)). The typical OHB yield of the method was 90%.

Results:

The kinetic parameters are listed in Table 2 for the tested enzymes on their natural substrates and OHB. Significant OHB reductase activity was found for all lactate dehydrogenases of different biological origin. Malate dehydrogenase, Mdh, of *E. coli* only had very minor activity on OHB. The branched chain 2-oxo-acid dehydrogenase, PanE, from *L. lactis* also had significant activity on OHB.

TABLE 2

Summary of kinetic parameters of selected candidate enzymes on their natural substrate and OHB

| Enzyme | Max. specific activity [µmol/(mg min)] | | Substrate affinity, Km [mM] | |
|---|---|---|---|---|
| | Natural substrate[a] | OHB[b] | Natural substrate[a] | OHB |
| Ec-Mdh | 95.6 | 0.01 | 0.04 | ns |
| Ll-Ldh | 184 | 18 | 2.7 | ns |
| Gs-Ldh | 87.7 | 66.8 | 1.2 | 1.3 |
| Bs-Ldh | 170 | 15.7 | nd | ns |
| Ll-PanE | nd | 2.58 | nd | ns |
| Oc-LdhA | 68.3 | 6.5 | 1.5 | 13 |
| Ec-LdhA | 265 | 0.56 | 1.8 | 4.8 |

[a] Natural substrates for Mdh and Ldh are oxaloacetate and pyruvate, respectively
[b] When enzymes could not be saturated, maximum specific activity refers to the activity estimated at 20 mM substrate concentration
ns—not saturated
nd—not determined

Example 2: Construction of Lactate Dehydrogenase Enzymes with Improved OHB Reductase Activity Site-directed mutagenesis of the *L. lactis* ldhA gene was carried out using the pET28-Ll-ldhA plasmid as the template. Point mutations to change the amino acid sequence were introduced by PCR (Phusion 1 U, HF buffer 20% (v/v), dNTPs 0.2 mM, direct and reverse primers 0.04 µM each, template plasmid 30-50 ng, water) using the oligonucleotide pairs listed in Table 3. The genes mutated by PCR contained a new restriction site listed in Table 3 (introduced using silent mutations) in addition to the functional mutation to facilitate identification of mutated clones. The PCR products were digested by DpnI at 37° C. for 1 h to remove template DNA, and transformed into competent *E. coli* DH5α (NEB) cells. The mutated plasmids were identified by restriction site analysis and were verified to carry the desired mutations by DNA sequencing.

TABLE 3

Oligonucleotides used to mutate lactate dehydrogenase
IdhA from *L. lactis* (nnk denotes a degenerated codon with k
representing either thymine or cytosine)

| Protein | Mutation | Primer sequences 5' - 3' | Restriction site |
|---|---|---|---|
| Ll-LdhA | Q85nnk | GTCTTGACTTCTGGTGCTCCANNKAAACCAGGTG AAACGCGTCTT (SEQ ID NO. 27) AAGACGCGTTTCACCTGGTTTMNNTGGAGCACCA GAAGTCAAGAC (SEQ ID NO. 28) | MluI |
| Ll-LdhA | I226V | CGTGATGCTGCTTACTCGATCGTCGCTAAAAAAG GTG (SEQ ID No. 99) CACCTTTTTTAGCGACGATCGAGTAAGCAGCATC ACG (SEQ ID No. 100) | PvuI |

Figure 2:
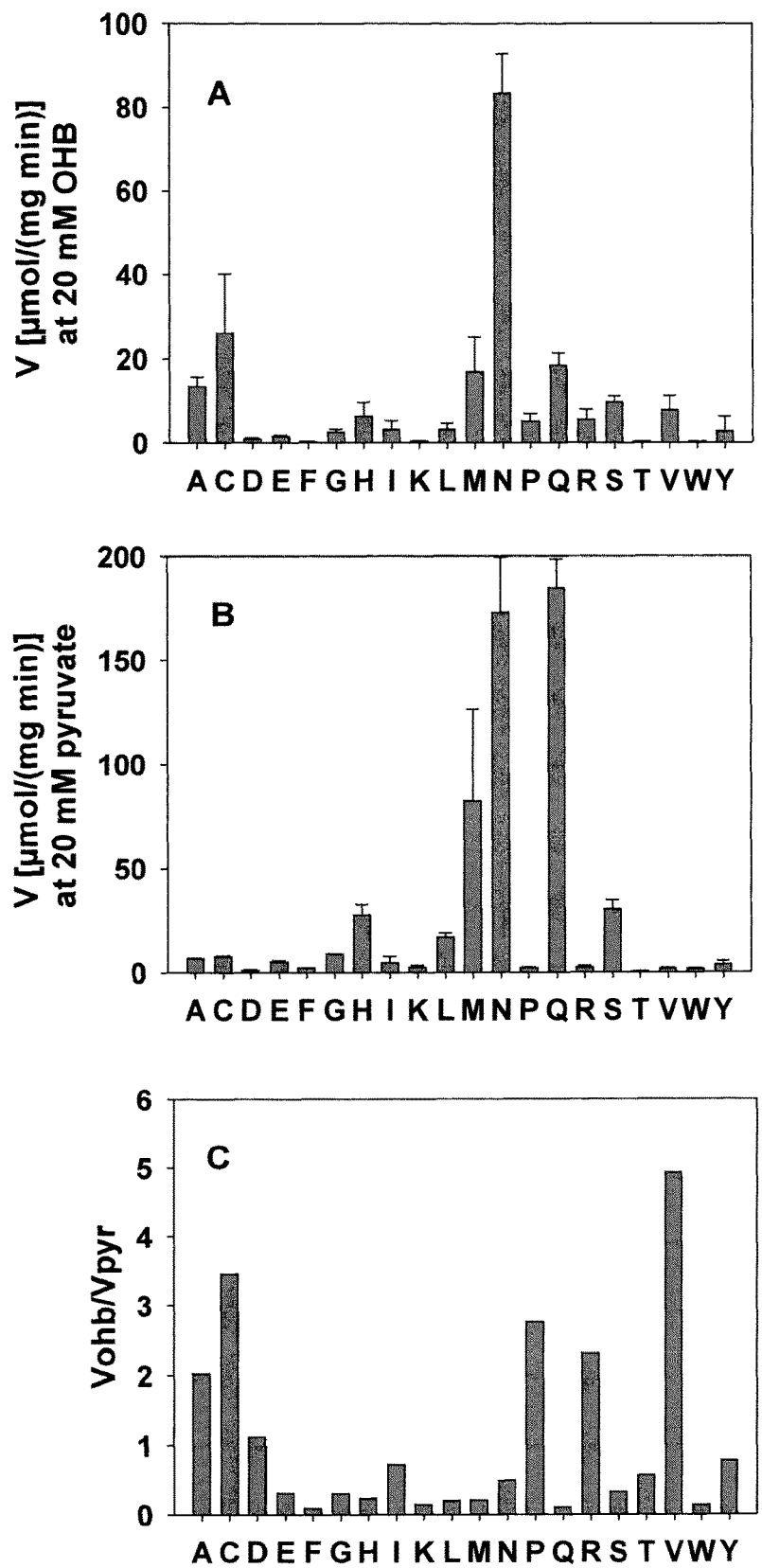
FIG. 2: Specific activities of purified *L. lactis* lactate dehydrogenase mutated in position Q85. (A) specific activities on OHB, (B) specific activities on pyruvate, (C) Substrate specificity expressed as ratio of Vmax values on OHB and pyruvate. Values higher than 1 in graph C indicate preference for OHB (no saturation of enzymatic activity was obtained on either substrate for mutated enzymes between 0 and 50 mM OHB or pyruvate). Activities were measured at a substrate concentration of 20 mM.

Mutant enzymes were expressed, purified and tested for OHB and pyruvate reductase activity as described in Example 1. The activity measurements for both substrates are summarized in FIG. 2. The results demonstrate that the replacement of Gln85 by preferably alanine, cysteine, asparagine, or methionine yields an increase of the enzyme's specificity for OHB, and/or an increase in maximum specific OHB reductase activity.

The mutation Q85N in Ll-Ldh was combined with mutation I226V. It was demonstrated that this exchange had a major positive impact on substrate affinity for OHB.

TABLE 4

Summary of kinetic parameters of *L. lactis* lactate dehydrogenase A, Ll-LdhA, mutants on pyruvate and OHB

| Mutant Enzyme | Seq ID | Max. specific activity [µmol/(mg min)] | | Km [mM] | |
|---|---|---|---|---|---|
| | | Pyruvate | OHB | Pyruvate | OHB |
| Q85N | SEQ ID No. 30 | 184 | 63.9 | 22.1 | 29.2 |
| Q85NI226V | SEQ ID No. 32 | 11.5 | 4.9 | 1.4 | 3.3 |

Example 3: Construction of Malate Dehydrogenase Enzymes with Improved OHB Reductase Activity Site-directed mutagenesis of the mdh gene from *E. coli* was carried out as described in Example 2 using the primers listed in Table 5. Plasmid pET28-Ec-mdh was used as the template.

TABLE 5

Oligonucleotides used to mutate malate dehydrogenase mdh from *E. coli*. (nnk denotes a degenerated codon with k representing either thymine ocytosine)

| Protein | Mutation | Primer sequences 5' - 3' | Restr. site |
|---|---|---|---|
| Ec-Mdh | R81nnk | TTATCTCTGCAGGCGTAGCGNNKAAACCCGGGATGGATCGTTC (SEQ ID No. 33) GAACGATCCATCCCGGGTTTMNNCGCTACGCCTGCAGAGATAA (SEQ ID No. 34) | SmaI |
| Ec-Mdh | R81AM85E | TTATCTCTGCAGGCGTAGCGGCTAAACCGGGTGAGGATCGTTCC GACCTG (SEQ ID NO. 35) CAGGTCGGAACGATCCTCACCCGGTTTAGCCGCTACGCCTGCA GAGATAA (SEQ ID NO. 36) | no SmaI |
| Ec-Mdh | R81A M85Q | TTATCTCTGCAGGCGTAGCGGCTAAACCGGGTCAGGATCGTTCC GACCTG (SEQ ID NO. 37) CAGGTCGGAACGATCCTGACCCGGTTTAGCCGCTACGCCTGCA GAGATAA (SEQ ID NO. 38) | no SmaI |
| Ec-Mdh | I12V | GTCGCAGTCCTCGGCGCCGCTGGCGGTGTCGGCCAGGCGCTTG CAC (SEQ ID NO. 39 GTGCAAGCGCCTGGCCGACACCGCCAGCGGCGCCGAGGACTG CGAC (SEQ ID NO. 40) | NarI |
| Ec-Mdh | G179D | CCG GTT ATT GGC GGC CAC TCT GAT GTT ACC ATT CTG CCG CTG CTG (SEQ ID NO. 41) CAGCAGCGGCAGAATGGTAACATCAGAGTGGCCGCCAATAACC GG (SEQ ID NO. 42) | EaeI |
| Ec-Mdh | R81AD86S | GGCGTAGCGGCTAAACCGGGTATGTCTCGTTCCGACCTG (SEQ ID NO. 43) CAGGTCGGAACGAGACATACCCGGTTTAGCCGCTACGCC (SEQ ID NO. 44) | no SmaI |

Figure 3:
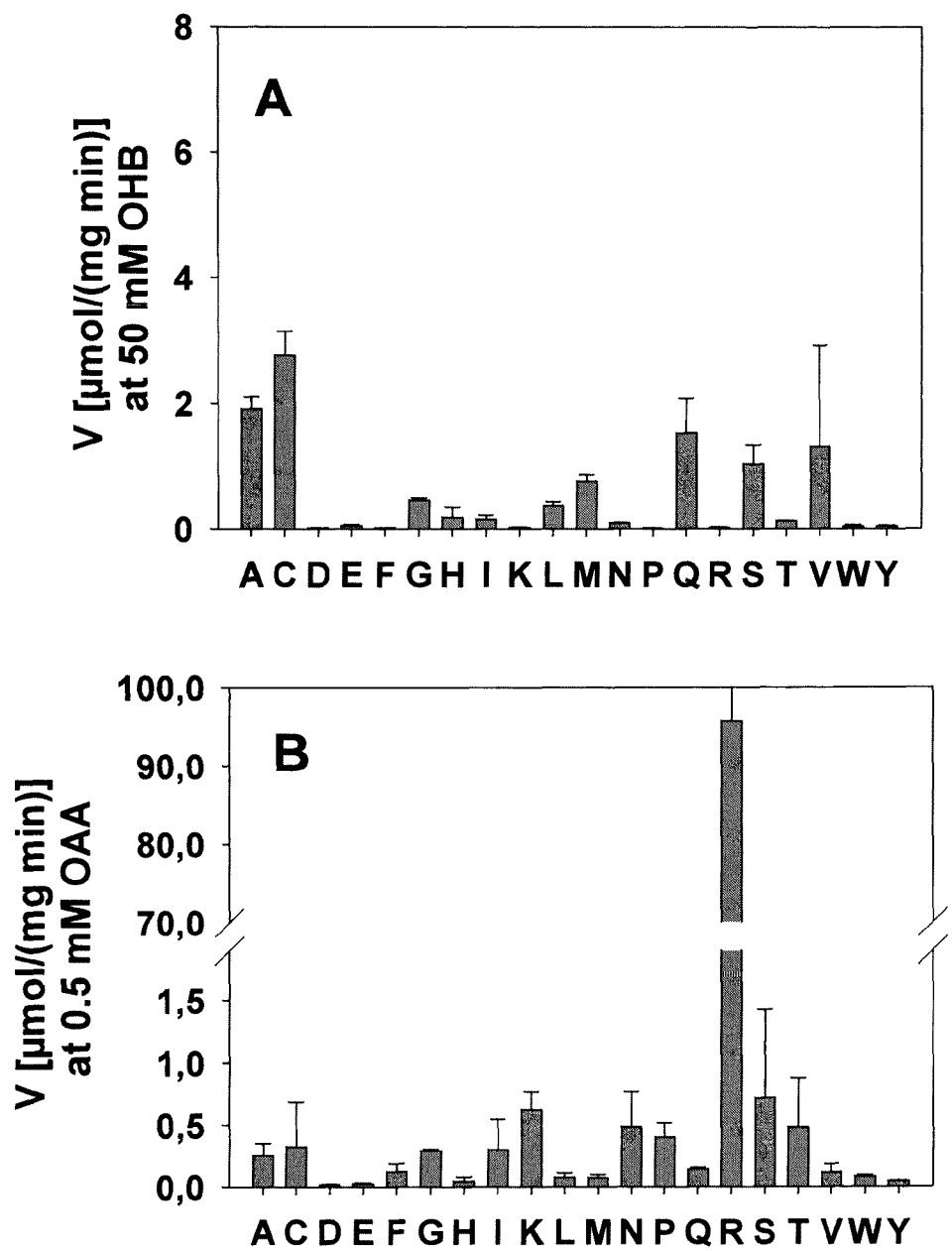
FIG. 3: Specific activities of purified *E. coli* malate dehydrogenase mutated in position R81. (A) specific activities on OHB, (B) specific activities on oxaloacetate. Activities were measured at a substrate concentration of 20 mM OHB or 0.5 mM oxaloacetate.

Mutant enzymes were expressed, purified and tested for OHB and oxaloacetate reductase activity as described in Example 1. The activity measurements on OHB and oxaloacetate are summarized in FIG. 3. The results demonstrate that replacement of Arg81 by alanine, cysteine, glycine, histidine, isoleucine, leucine, methionine, asparagine, glutamine, serine, threonine, or valine confer significant OHB reductase activity, and concomitant decrease of oxaloacetate reductase activity.

The mutation R81A in Ec-Mdh was combined with additional changes in the protein sequence. The results are listed in Table 6. It was demonstrated that the introduction of mutations M85Q, M85E, I12V, D86S or G179D result in an increased activity on OHB.

TABLE 6

Summary of kinetic parameters of *E. coli* malate dehydrogenase mutants on oxaloacetate (OAA) and OHB

| Mutant Enzyme | Seq ID | Max. specific activity [μmol/(mg min)] | | Km [mM] | |
|---|---|---|---|---|---|
| | | OAA[a] | OHB[b] | OAA | OHB |
| Wild-type | SEQ ID No. 2 | 95 | 0.01 | 0.04 | ns |
| R81A | SEQ ID No. 102 | 1.16 | 1.8 | ns | ns |
| R81A M85Q | SEQ ID No. 104 | 0.5 | 4.99 | ns | ns |
| R81A M85E | SEQ ID No. 106 | 1 | 3 | ns | ns |
| R81A M85Q I12V | SEQ ID No. 108 | 1.84 | 18.9 | ns | 15 |
| R81A M85E I12V | SEQ ID No. 110 | 2.2 | 12.54 | ns | ns |
| R81A G179D | SEQ ID No. 112 | 0.37 | 4.16 | ns | ns |
| R81A D86S | SEQ ID No. 1114 | 0.67 | 14.6 | ns | ns |
| R81A I12V | SEQ ID No. 115 | 0.5 | 4.9 | ns | ns |
| R81A G179D D86S | SEQ ID No. 118 | 0.54 | 19 | ns | ns |

[a] activity was measured at 0.5 mM oxaloacetate
[b] activity was measured at 20 mM OHB
ns—not saturated at concentrations of up to 50 mM of OHB and 0.5 mM of oxaloacetate

Example 4: Demonstration of Homoserine Transaminase Activity for Selected Transaminases The genes coding for different transaminases in *E. coli*, *S. cerevisiae*, and *L. lactis* were amplified by PCR using the high-fidelity polymerase Phusion™ (Finnzymes) and the primers listed in Table 7. Genomic DNA of *E. coli* MG1655, *S. cerevisiae* BY4741, and *L. lactis* IL1403 were used as the templates. The primers introduced restriction sites (Table 7) upstream of the start codon and downstream of the stop codon, respectively, facilitating the ligation of the digested PCR products into the corresponding sites of the pET28a+ (Novagen) expression vector using T4 DNA ligase (Biolabs). Ligation products were transformed into *E. coli* DH5α cells. The resulting plasmids were isolated and shown by DNA sequencing to contain the correct full-length sequence of the corresponding genes. The references to the corresponding protein sequences are listed in Table 7.

Transaminase Assays (Reaction Scheme)

Transaminase: Amino acid+2-oxoglutarate→2-oxo-acid+glutamate

Dehydrogenase: 2-oxo-acid+NADH→2-hydroxy-acid+NAD$^+$

The reaction mixture contained 60 mM Hepes (pH 7), 50 mM potassium chloride, 5 mM MgCl$_2$, 4 mM 2-oxoglutarate, 0.1 mM pyridoxal-5'-phosphate (PLP), 0.25 mM NADH, (optionally 5 mM fructose-1,6-bisphosphate) (all products from Sigma), 4 Units/mL of auxiliary 2-hydroxy-acid dehydrogenase, and appropriate amounts of purified aminotransferase or cell extract. The auxiliary dehydrogenase enzyme was purified PanE from *L. lactis* in case of the amino acids phenylalanine and leucine (Chambellon, Rijnen, Lorquet, Gitton, van HylckamaVlieg, Wouters, &

TABLE 7

Primer sequences and restriction sites used for amplification and cloning of candidate enzymes (Abbreviations used for source organism: Ec—*E. coli*, Sc—*S. cerevisiae*, Ll—*L. lactis*). All the genes were cloned into pET28a+ (Novagen), adding an N-terminal Hexa-HisTag.

| Gene | Forward and reverse primer sequences 5' - 3' | Gene sequence | Protein sequence | Restriction sites |
|---|---|---|---|---|
| Ec-ilvE | tataatgctagcatgaccacgaagaaagctgattaca (SEQ ID No. 47) tataatggatccttattgattaacttgatctaacc (SEQ ID No. 48) | SEQ ID No. 59 | SEQ ID No. 60 | NheI BamHI |
| Ec-tyrB | Tataatgctagcgtgtttcaaaaagttgacg (SEQ ID No. 49) Tataatggatccttacatcaccgcagcaaac (SEQ ID No. 50) | SEQ ID No. 61 | SEQ ID No. 62 | NheI BamHI |
| Ec-aspC | Tataatgctagcatgtttgagaacattaccgc (SEQ ID No. 51) Tataatggatccttacagcactgccacaatcg (SEQ ID No. 52) | SEQ ID No. 63 | SEQ ID No. 64 | NheI BamHI |
| Ll-araT | Tataatgctagcatggatttattaaaaaaatttaaccct aa (SEQ ID No. 53) Tataatggatcctcagccacgttttttagtcacataa (SEQ ID No. 54) | SEQ ID No. 65 | SEQ ID No. 66 | NheI BamHI |
| Ll-bcaT | Tataatgctagcatggcaattaatttagactg (SEQ ID No.55) Tataatggatccttaatcaactttaactatcc (SEQ ID No. 56) | SEQ ID No. 67 | SEQ ID No. 68 | NheI BamHI |
| Sc-ARO8 | Tataatcatatgatcatgactttacctgaatcaaaaga (SEQ ID No. 57) Tataatggatccctatttggaaataccaaattcttcg (SEQ ID No.58) | SEQ ID No. 69 | SEQ ID No. 70 | NheI BamHI |

Enzymes were expressed and purified as described in Example 1, and tested for homoserine transaminase activity under the conditions described below.

Enzymatic Assays:

Transaminase activity of several candidate aminotransferases was quantified with 2-oxoglutarate as the amino group acceptor. Transaminase reactions were carried out using homoserine and the preferred amino acid of the enzymes. The reactions were followed by the amino acid-dependent oxidation of NADH in the coupled dehydrogenase reaction.

Yvon, 2009), malate dehydrogenase (Sigma) in case of aspartate, and rabbit muscle (L)-lactate dehydrogenase (Sigma) when homoserine was used as the starting substrate. Reactions were started by adding 50 mM of the amino acid.

Enzymatic assays were carried out at 37° C. in 96-well flat bottomed microtiter plates in a final volume of 250 μL. The reactions were followed by the characteristic absorption of NAD(P)H at 340 nm ($\varepsilon_{NADPH}$=6.22 mM$^{-1}$ cm$^{-1}$) in a microplate reader (BioRad 680XR).

Results:

The kinetic parameters of different aminotransferases are listed in Table 8. Significant homoserine transaminase activity was found for the listed transaminase enzymes.

TABLE 8

Transaminase activities of tested candidate enzymes on homoserine and their preferred amino acid substrate (Abbreviations used for source organism: Ec—*E. coli*, Sc—*S. cerevisiae*, Ll—*L. lactis*).

| Enzyme | Max. specific activity on different substrates [µmol/(min mg$_{prot}$)] | |
|---|---|---|
| | Homoserine* | Preferred amino acid |
| Ec-IlvE | 0.077 | 10.6$^{(L)}$ |
| Ec-TyrB | 0.057 | 9.03$^{(P)}$ |
| Ec-AspC | 0.082 | 74.031$^{(A)}$ |
| Ll-AraT | 0.109 | 11.72$^{(P)}$ |
| Ll-BcaT | 0.028 | 30.39$^{(L)}$ |
| Sc-ARO8 | 0.076 | 20.5$^{(P)}$ |

*activity measured at 50 mM homoserine,

Example 5: Construction of Plasmids for Overexpression of the Homoserine Pathway Enzymes Construction of the Plasmids pTAC-op-HMS1 and pACT3-op-HMS1

The plasmid pET28-LYSCwt was constructed by amplifying the lysC gene by PCR using high fidelity polymerase Phusion™ (Finnzymes) and the direct and reverse primers 5'CACGAGGTACATATGTCTGAAATTGTT-GTCTCC3' (SEQ ID No. 71) and 5'CTTCCAGGGGATC-CAGTATTTACTCAAAC3' (SEQ ID No. 72) that introduced a NdeI and BamHI restriction sites upstream of the start codon and downstream of the stop codon, respectively. Genomic DNA from *E. coli* MG1655 was used as the template. The PCR product was digested with NdeI and BamHI, ligated into the corresponding sites of the pET28a (Novagen) expression vector using T4 DNA ligase (Biolabs), and transformed into *E. coli* DH5α cells. The resulting pET28-LYSCwt plasmid was isolated and shown by DNA sequencing to contain the full-length lysC gene having the correct sequence (SEQ ID No. 73).

Site-directed mutagenesis of lysC to alleviate inhibition by lysine was carried out using the pET28-LYSCwt plasmid as the template. A point mutation to change the amino acid sequence in position 250 from glutamate to lysine (E250K, SEQ ID No. 36) was introduced by PCR (Phusion 1 U, HF buffer 20% (v/v), dNTPs 0.2 mM, direct and reverse primers 0.04 µM each, template plasmid 50 ng, water) using the oligonucleotides 5'GCGTTTGCCGAAGCG-GCAAAGATGGCCACTTTTG3' (SEQ ID No. 74) and 5'CAAAAGTGGCCATCTTTGCCGCTTCG-GCAAACGC3' (SEQ ID No. 75). The PCR product (SEQ ID No. 35) was digested by DpnI at 37° C. for 1 h to remove template DNA, and transformed into competent *E. coli* DH5α (NEB) cells. The mutated plasmid pET28-LYSC* was identified by restriction site analysis and verified to carry the desired mutations by DNA sequencing.

The plasmid pET28-ASDwt was constructed by amplifying the asd gene of *E. coli* by PCR using high fidelity polymerase Phusion™ (Finnzymes) and the direct and reverse primers 5'TATAATGCTAGCATGAAAAATGTTG-GTTTTATCGG3' (SEQ ID No. 76) and 5'TATAATGGA-TCCTTACGCCAGTTGACGAAGC3' (SEQ ID No. 77) that introduced a NheI and BamHI restriction site upstream of the start codon and downstream of the stop codon, respectively. Genomic DNA from *E. coli* DH5α was used as the template. The PCR product was digested with NheI and BamHI, ligated into the corresponding sites of the pET28a (Novagen) expression vector using T4 DNA ligase (Biolabs), and transformed into *E. coli* DH5α cells. The resulting pET28-ASDwt plasmid was isolated and shown by DNA sequencing to contain the full-length asd gene having the correct sequence (SEQ ID No. 98).

The plasmid pET28-HOM6 wt was constructed by amplifying the HOM6 gene of *S. cerevisiae* by PCR using high fidelity polymerase Phusion™ (Finnzymes) and the direct and reverse primers 5'TATAATCATATGAGCACTAAAGT-TGTTAATG3' (SEQ ID No. 78) and 5'TATAATGGATC-CCTAAAGTCTTTGAGCAATC3' (SEQ ID No. 79) that introduced a NdeI and BamHI restriction site upstream of the start codon and downstream of the stop codon, respectively. Genomic DNA from *S. cerevisiae* BY4741 was used as the template. The PCR product was digested with NdeI and BamHI, ligated into the corresponding sites of the pET28a (Novagen) expression vector using T4 ligase (Biolabs), and transformed into *E. coli* DH5α cells. The resulting pET28-HOM6 wt plasmid was isolated and shown by DNA sequencing to contain the full-length HOM6 gene having the correct sequence (SEQ ID No. 97).

The plasmid pET28-LYSC* was used as the backbone for the construction of the pTAC-op-HMS plasmid that enabled the expression of lysine-insensitive aspartate kinase, aspartate semialdehyde dehydrogenase, and homoserine dehydrogenase from an inducible tac promoter.

The asd gene was obtained by PCR from pET28-asdwt. The whole coding region and part of the upstream region comprising the pET28 ribosome binding site (rbs) and the in-frame N-terminal His-Tag were amplified by PCR using high fidelity polymerase Phusion™ (Finnzymes) and the direct and reverse primers 5'TATAAGGATCCGTT-TAACTTTAAGAAGGAGATATACCATGGG3' (SEQ ID No. 80) and 5'TATAAGAATTCTTACGCCAGTTGAC-GAAG3' (SEQ ID No. 81) that introduced a BamHI and EcoRI restriction site upstream of the rbs and downstream of the stop codon, respectively. The PCR product was digested with BamHI and EcoRI, ligated into the corresponding sites of pET28-LYSC*, using T4 DNA ligase (Biolabs), and transformed into *E. coli* DH5α cells. The resulting pET28-LYSC*-ASD plasmid was isolated and shown by DNA sequencing to have the correct sequence.

The HOM6 gene was obtained by PCR from pET28-HOM6 wt. The whole coding region and part of the upstream region comprising the pET28 ribosome binding site and the in-frame N-terminal His-Tag were amplified by PCR using high fidelity polymerase Phusion™ (Finnzymes), the direct primer 5'TATAAGCGGCCGCGTTTAACTT-TAAGAAGGAGATAT3' (SEQ ID No. 82), and the reverse primer 5'TATAAACTCGAGCCTAAAGTCTTTGAG-CAAT3' (SEQ ID No. 83) that introduced a NotI and a PspXI restriction site upstream of the rbs and downstream of the stop codon, respectively. The PCR product was digested with NotI and PspXI, ligated into the corresponding sites of pET28-LYSC*-ASD, using T4 DNA ligase (Biolabs), and transformed into *E. coli* DH5α cells. The resulting pET28-op-HMS1 plasmid was isolated and shown by DNA sequencing to have the correct sequence.

The 5' upstream promoter region simultaneously regulating the expression of the three genes (i.e. the T7 promoter in pET28a+) can be replaced with any other promoter, inducible or constitutive, by digesting the plasmids with SphI and XbaI and cloning another promoter region with suitable restriction sites.

In the present non-exclusive example, the T7 promoter of the pET28a+ backbone was replaced by the artificial IPTG-inducible tac promoter (de Boer et al., 1983). The tac promoter was obtained from plasmid pEXT20 (Dykxhoorn et al., 1996) by digesting this plasmid with SphI and XbaI. The DNA fragment containing the promoter was purified and cloned into SphI and XbaI digested pET28-op-HMS1 obtaining pTAC-op-HMS1. The resulting pTAC-op-HMS plasmid was isolated and shown by DNA sequencing to have the correct sequence.

The operon containing the coding sequences of lysC*, asd, and HOM6 was PCR amplified from the plasmid pTAC-op-HMS1 using the primers 5'-TATAAAGATCTTA-GAAATAATTTTGTTTA-3' (SEQ ID No. 84) and 5'-TATAATCTAGACTAAAGTCTTTGAGCAAT-3' (SEQ ID No. 85) which introduced a BglII and a XbaI restriction site at the 5' and the 3' end, respectively, of the PCR fragment. The fragment was purified, digested with BglII and XbaI and cloned into the corresponding sites of pACT3 (Dykxhoorn et al., 1996) to obtain the vector pACT3-op-HMS1. The resulting pACT3-op-HMS1 plasmid was isolated and shown by DNA sequencing to have the correct sequence.

Construction of the Plasmids pEXT20-op-HMS2 and pACT3-op-HMS2

The plasmid pET28-thrAwt was constructed by amplifying the E. coli thrA gene encoding bifunctional enzyme aspartate kinase/homoserine dehydrogenase I by PCR using high fidelity polymerase Phusion™ (Finnzymes) and the direct and reverse primers 5'-TATAATCATATGCGAGTGT-TGAAGTTCG-3' (SEQ ID No. 86) and 5'-TATAATG-GATCCTCAGACTCCTAACTTCCA-3' (SEQ ID No. 87) that introduced a NdeI and BamHI restriction sites upstream of the start codon and downstream of the stop codon, respectively. Genomic DNA from E. coli MG1655 was used as the template. The PCR product was digested with NdeI and BamHI, ligated into the corresponding sites of the pET28a+ (Novagen) expression vector using T4 DNA ligase (Biolabs), and transformed into NEB 5-alpha competent E. coli cells (NEB). The resulting pET28-thrAwt plasmid was isolated and shown by DNA sequencing to contain the full-length thrA gene having the correct sequence (SEQ ID No. 88). The corresponding protein is represented by SEQ ID No. 89.

An aspartate kinase/homoserine dehydrogenase with strongly decreased sensitivity for inhibition by threonine was constructed by site directed mutagenesis, replacing serine in position 345 with phenylalanine (S345F). Site-directed mutagenesis was carried out using the direct and reverse primers 5'-TGT CTCGAGCCCGTATTTTCGTGGTGCTG-3' (SEQ ID No. 90) and 5'-CAGCACCACGAAAATACGGG CTCGAGACA-3' (SEQ ID No. 91) and the pET28-thrAwt plasmid as the template. A single point mutation to change the amino acid sequence was introduced by PCR (Phusion 1 U, HF buffer 20% (v/v), dNTPs 0.2 mM, direct and reverse primers 0.04 µM each, template plasmid 30-50 ng, water). Plasmids created by PCR contained a new restriction site for XhoI (underlined) introduced by silent mutation in addition to the functional mutation to facilitate identification of mutated clones. The PCR products were digested by DpnI at 37° C. for 1 h to remove template DNA, and transformed into DH5α competent E. coli cells (NEB). The mutated plasmid pET_Ec_thrA_S345F was identified by restriction site analysis and verified to carry the desired mutation by DNA sequencing.

The thrAS345F coding region of the bifunctional E. coli aspartate kinase/homoserine dehydrogenase was obtained by PCR using the plasmid pET_Ec_thrA_S345F as the template (SEQ ID No. 92). The whole coding region was amplified by PCR using high fidelity polymerase Phusion™ (Finnzymes) and the direct and reverse primers 5'-TATAAT GAGCTCGTTTAACTTTAAGAAGGAGATATACCATGC GAGTGTTGA AGTTCGGCG-3' (SEQ ID No. 93) and 5'-TATAATCCCGGGTCAGACTCCTAACTTCCA-3' (SEQ ID No. 94) that introduced a SacI and XmaI restriction site (underlined) upstream of the start codon and downstream of the stop codon, respectively. The direct primer includes the ribosome binding site (bold face) sequence of pET28. The PCR product was digested with SacI and XmaI, ligated into the corresponding sites of either pEXT20 or pACT3 (Dykxhoorn, St Pierre, & Linn, 1996), using T4 DNA ligase (Biolabs), and transformed into E. coli DH5α cells. The resulting pEXT20-op-HMS2_step1 and pACT3-op-HMS2_step1 plasmids were isolated and shown by DNA sequencing to have the correct sequence.

Escherichia coli aspartate semialdehyde dehydrogenase asd was amplified by PCR using high fidelity polymerase Phusion™ (Finnzymes) and the direct and reverse primers 5'-TATAATCCCGGGGTTTAACTTTAAGAAGGAGATAT ACCATGAAAAATGTTG GTTTTATCGGC-3' (SEQ ID No. 95) and 5'-TATAATGGATCC TTACGCCAGTTGAC-GAAG-3' (SEQ ID No. 96) that introduced a XmaI and BamHI restriction site upstream of the start codon and downstream of the stop codon, respectively (SEQ ID No. 98). The direct primer includes the ribosome binding site sequence of pET28. Genomic DNA of E coli MG1655 was used as the template. The PCR product was digested with XmaI and BamHI, ligated into the corresponding sites of pEXT20-op-HMS2_step1 and pACT3-op-HMS2_step1, directly downstream the E. coli thrA gene, using T4 DNA ligase (Biolabs), and transformed into E. coli DH5α cells. The resulting pEXT20-op-HMS2 and pACT3-op-HMS2 plasmids were isolated and shown by DNA sequencing to have the correct sequence.

Example 6: Construction of Plasmids for Overexpression of Phosphoenolpyruvate (PEP) Carboxykinase, PEP Carboxylase, Pyruvate Kinase, Pyruvate Carboxylase, Isocitrate Lyase Enzymes and the Galactose Symporter Permease The plasmid pACT3-pck harbouring the PEP carboxykinase encoding pck gene of E. coli was constructed by amplifying the pck coding sequence using genomic DNA from E. coli MG1655 as the template and the forward and reverse primers, respectively, 5'TATAATCCCGGGAT-GCGCGTTAACAATGGTTTGACC3' (SEQ ID No. 119) and 5'TATAATTCTAGATTACAGTTTCGGACCAGCCG3' (SEQ ID No. 120). The DNA fragment was digested with XmaI and XbaI, ligated into the corresponding sites of the pACT3 expression vector (Dykxhoorn et al., 1996) using T4 DNA ligase (Biolabs), and transformed into E. coli DH5α cells. The transformants were selected on solid LB medium containing chloramphenicol (25 µg/mL). The resulting plasmid was isolated and correct insertion of the pck gene was verified by sequencing. Plasmids pACT3-aceA, pACT3-ppc, pACT3-galP, pACT3-pck and pACT3-pycA harbouring, respectively, aceA, ppc, galP, or pck (all E. coli) or pycA from Lactococcus lactis were constructed analogously using the primers listed in Table 9.

TABLE 9

Primers used for construction of plasmids for gene overexpression.
Restriction sites used for cloning into pACT3 are underlined

| Gene | Primer | Linker | Sequence |
|---|---|---|---|
| Ec_pck | Ec_pck_clon_for | XmaI | tataatcccgggatgcgcgttaacaatggtttgacc (SEQ ID No. 121) |
| | Ec_pck_clon_rev | XbaI | tataattctagattacagtttcggaccagccg (SEQ ID No. 122) |
| Ec_ppc | Ec_ppc_clon_for | XmaI | tataatcccgggatgaacgaacaatattcc (SEQ ID No. 123) |
| | Ec_ppc_clon_rev | XbaI | tataattctagattagccggtattacgcat (SEQ ID No. 124) |
| Ec_aceA | Ec_aceA_clon_for | XmaI | tataatcccgggatgaaaacccgtacacaacaaatt (SEQ ID No. 125) |
| | Ec_aceA_clon_rev | XbaI | tataattctagattagaactgcgattcttcag (SEQ ID No. 126) |
| Ll_pycA | Ll_pycA_clon_for | XmaI | tataatcccgggatgaaaaaactactcgtcgccaat (SEQ ID No. 127) |
| | Ll_pycA_clon_rev | XbaI | tataattctagattaattaatttcgattaaca (SEQ ID No. 128) |
| Ec_galP | Ec_galP_clon_for | XmaI | tataatcccgggatgcctgacgctaaaaaacaggggcggt (SEQ ID No. 129) |
| | Ec_galP_clon_rev | XbaI | tataattctagattaatcgtgagcgcctatttc (SEQ ID No. 130) |

Example 7: Construction of the Plasmid for Overexpression of the Homoserine Transaminase and the OHB Reductase The coding sequence of the branched chain amino transferase, IlvE, from *E. coli* was PCR amplified using the forward and reverse primers 5'-ACAATTTCACACAG-GAAACAGAATTCGAGCTCGGTACCGTTTAACTT-TAAG AAGGAGATATACCATGACCAC-GAAGAAAGCTGATTAC-3' (SEQ ID No. 131) and 5'-GGATAACTTTTTTACGTTGTTTATCAGCCATGG-TATATCTCCTTCTTAAAGT TAAACGGATCCTTATT-GATTAACTTG-3' (SEQ ID No. 132), respectively, and plasmid pET28-Ec-ilvE (Example 4) as the template. The coding sequence of lactate dehydrogenase, LdhA, from *L. lactis* was PCR amplified using the forward and reverse primers 5'-TAATATGGATCCGTTTAACTT-TAAGAAGGAGATATACCATGGCTGATAAAC AACG-TAAAAAAGTTATCC-3' (SEQ ID No. 133) and 5'-CAAT-GCGGAATATTGTTCGTTCATGGTATATCTCCTTCTTA-AAGTTAAACTC TAGATTAGTTTTTAACTGCA-GAAGCAAATTC-3' (SEQ ID No. 134), respectively, and plasmid pET28-Ll-ldhA (Example 1) as the template. The amplified PCR fragments were fused in an overlap extension PCR by adding 150 ng of each fragment to 50 µL of the reaction mix and running a PCR using primers 5'-ACAATTTCACACAGGAAACAGAATTCGAGCTCG-GTACCGTTTAACTTTAAG AAGGAGATATACCAT-GACCACGAAGAAAGCTGATTAC-3' (SEQ ID No. 135) and 5'-CAATGCGGAATATTGTTCGTTCATGG-TATATCTCCTTCTTAAAGTTAAACTC TAGATT-AGTTTTTAACTGCAGAAGCAAATTC-3' (SEQ ID No. 136). The resulting PCR fragment was purified, digested with KpnI and XbaI, and ligated into the corresponding sites of pEXT20 (Dykxhoorn, St Pierre, & Linn, 1996) using T4 DNA ligase (Fermentas). The ligation product was transformed into *E. coli* DH5α. The resulting plasmid pEXT20-DHB was isolated and shown by DNA sequencing to contain the correct full-length coding sequences of Ec-ilvE and Ll-ldhA. The plasmid was then transformed into *E. coli* MG1655-derived mutant strains and tested regarding DHB production.

Example 8: Construction of Optimized Strains for DHB Production

Several genes were disrupted in *E. coli* strain MG1655 in order to optimise carbon flux repartitioning and cofactor supply for DHB production. Gene deletions were carried out using phage transduction method, or the lambda red recombinase method according to Datsenko et al. (Datsenko & Wanner, 2000).

Protocol for Introduction of Gene Deletions Using the Phage Transduction Method:

Strains carrying the desired single deletions were obtained from the Keio collection (Baba et al., 2006). Phage lysates of single deletion mutants were prepared by inoculating 10 mL of LB medium containing 50 µg/mL kanamycin, 2 g/L glucose, and 5 mM $CaCl_2$ with 100 µL of overnight precultures. Following an incubation of 1 h at 37° C., 200 µL of phage lysate prepared from the wild-type MG1655 strain were added, and cultures were incubated for another 2-3 h until cell lysis had completed. After addition of 200 µL chloroform, cell preparations were first vigorously vortexted and then centrifuged for 10 min at 4500×g. The clear lysate was recovered and stored at 4° C.

The receptor strain was prepared for phage transduction by an overnight cultivation at 37° C. in LB medium. A volume of 1.5 mL of the preculture was centrifuged at 1500×g for 10 min. The supernatant was discarded and the cell pellet was resuspended in 600 µl of a solution containing 10 mM $MgSO_4$ and 5 mM $CaCl_2$. The transduction was carried out by mixing 100 µL of the solution containing the receptor strain with 100 µL of lysate and incubating this mixture at 30° C. for 30 min. Thereafter, 100 µL of a 1M sodium citrate solution were added followed by vigorous vortexing. After addition of 1 mL LB medium, the cell suspension was incubated at 37° C. for 1 h before spreading the cells on LB agar dishes containing 50 μg/mL kanamycin. Clones able to grow in presence of the antibiotic were confirmed by colony PCR to contain the desired deletion using the primers listed in Table 11. After the introduction of each gene deletion, the antibiotic marker was removed as described above following the method of (Cherepanov & Wackernagel, 1995). The deletions ΔldhA, ΔadhE, ΔmetA, ΔthrB, ΔrhtB, and ΔlldD were successively introduced by the described method.

Protocol for Introduction of Gene Deletions Using the Lambda-Red Recombinase Method:

The deletion cassettes were prepared by PCR using high fidelity polymerase Phusion™ (Finnzymes), and the FRT-flanked kanamycin resistance gene (kan) of plasmid pKD4 as the template (Datsenko & Wanner, 2000). Sense primers contained sequences corresponding to the 5' end of each targeted gene (underlined) followed by 20 bp corresponding to the FRT-kan-FRT cassette of pKD4. Anti-sense primers contained sequences corresponding to the 3' end region of each targeted gene (underlined) followed by 20 bp corresponding to the cassette. The primers are described in Table 10. PCR products were digested with DpnI and purified prior to transformation.

E. coli MG1655 strain was rendered electro-competent by growing the cells to an $OD_{600}$ of 0.6 in LB liquid medium at 37° C., concentrating the cells 100-fold, and washing them twice with ice-cold 10% glycerol. The cells were transformed with plasmid pKD46 (Datsenko & Wanner, 2000) by electroporation (2.5 kV, 200 Ω, 25 μF, in 2 mm gap cuvettes). Transformants were selected at 30° C. on ampicillin (100 μg/mL) LB solid medium.

Disruption cassettes were transformed into electro-competent E. coli strains harbouring the lambda Red recombinase-expressing plasmid pKD46. The cells were grown at 30° C. in liquid SOB medium containing ampicillin (100 μg/mL). The lambda red recombinase system was induced by adding 10 mM arabinose when $OD_{600}$ of the cultures reached 0.1. Cells were further grown to an $OD_{600}$ of 0.6 before they were harvested by centrifugation, washed twice with ice-cold 10% glycerol, and transformed with the disruption cassette by electroporation. After an overnight phenotypic expression at 30° C. in LB liquid medium, cells were plated on solid LB medium containing 25 μg/mL kanamycin. Transformants were selected after cultivation at 30° C.

The gene replacement was verified by colony PCR using Crimson Taq polymerase (NEB). A first reaction was carried out with the flanking locus-specific primers (see Table 11) to verify simultaneous loss of the parental fragment and gain of the new mutant specific fragment. Two additional reactions were done by using one locus-specific primer together with one of the corresponding primers k1rev, or k2 for (see Table 11) that align within the FRT-kanamycin resistance cassette (sense locus primer/k1rev and k2for/reverse locus primer).

The resistance gene (FRT-kan-FRT) was subsequently excised from the chromosome using the FLP recombinase-harbouring plasmid pCP20 (Cherepanov & Wackernagel, 1995) leaving a scar region containing one FRT site. pCP20 is an ampicillin and CmR plasmid that shows temperature-sensitive replication and thermal induction of FLP recombinase synthesis. Kanamycin resistant mutants were transformed with pCP20, and ampicillin-resistant transformants were selected at 30° C. Transformants were then grown on solid LB medium at 37° C. and tested for loss of all antibiotic resistances. Excision of the FRT-kanamycin cassette was analysed by colony PCR using crimson taq polymerase and the flanking locus-specific primers (Table 11). Multiple deletions were obtained by repeating the above described steps.

TABLE 10

Primers used for gene disruptions. Sequences homologous to target genes are underlined

| Gene | Primer | Sequence |
|---|---|---|
| ldhA | Δ_ldhA_for | gaaggttgcgcctacactaagcatagttgttgatgagtgtaggctggagctgcttc (SEQ ID No. 137) |
|  | Δ_ldhA_rev | ttaaaccagttcgttcgggcaggtttcgccttttcatgggaattagccatggtcc SEQ ID No. 138) |
| adhE | Δ_adhE_for | atggctgttactaatgtcgctgaacttaacgcactcgtagagcgtgtgtaggctggagctgcttc (SEQ ID No. 139) |
|  | Δ_adhE_rev | ttaagcggattttttcgcttttttctcagctttagccggagcagccatatgaatatcctccttag (SEQ ID No. 140) |
| ackA | Δ_ackA_for | atgtcgagtaagttagtactggttctgaactgcggtagttcttcagtgtaggctggagctgcttc (SEQ ID No. 141) |
|  | Δ_ackA_rev | tcaggcagtcaggcggctcgcgtcttgcgcgataaccagttcttccatatgaatatcctccttag (SEQ ID No. 142) |
| focA-pflB | Δ_focA-pflB_for | ttactccgtatttgcataaaaaccatgcgagttacgggcctataagtgtaggctggagctgcttc (SEQ ID No. 143) |
|  | Δ_focA-pflB rev | atagattgagtgaaggtacgagtaataacgtcctgctgctgttctcatatgaatatcctccttag (SEQ ID No. 144) |
| pta | Δ_pta_for | gtgtcccgtattattatgctgatccctaccggaaccagcgtcggtgtgtaggctggagctgcttc (SEQ ID No. 145) |
|  | Δ_pta_rev | ttactgctgctgtgcagactgaatcgcagtcagcgcgatggtgtacatatgaatatcctccttag (SEQ ID No. 146) |
| poxB | Δ_poxB_for | atgaaacaaacggttgcagcttatatcgccaaaacactcgaatcggtgtaggctggagctgcttc (SEQ ID No. 147) |
|  | Δ_poxB_rev | ttaccttagccagtttgttttcgccagttcgatcacttcatcacccatatgaatatcctccttag (SEQ ID No. 148) |
| sad | Δ_sad_for | atgaccattactccggcaactcatgcaatttcgataaatcctgccgtgtaggctggagctgcttc (SEQ ID No. 149) |

TABLE 10-continued

Primers used for gene disruptions. Sequences homologous to target genes are underlined

| Gene | Primer | Sequence |
|---|---|---|
| | Δ_sad_rev | tcagatccggtctttccacaccgtctggatattacagaattcgtgcatatgaatatcctccttag (SEQ ID No. 150) |
| gabD | Δ_gabD_for | atgaaacttaacgacagtaacttattccgccagcaggcgttgattgtgtaggctggagctgcttc (SEQ ID No. 151) |
| | Δ_gabD_rev | ttaaagaccgatgcacatatatttgatttctaagtaatcttcgatcatatgaatatcctccttag (SEQ ID No. 152) |
| gadA | Δ_gadA_for | atggaccagaagctgttaacggatttccgctcagaactactcgatgtgtaggctggagctgcttc (SEQ ID No. 153) |
| | Δ_gadA_rev | tcaggtgtgtttaaagctgttctgctgggcaatacccctgcagtttcatatgaatatcctccttag (SEQ ID No. 154) |
| gadB | Δ_gadB_for | atggataagaagcaagtaacggatttaaggtcggaactactcgatgtgtaggctggagctgcttc (SEQ ID No. 155) |
| | Δ_gadB_rev | tcaggtatgtttaaagctgttctgttgggcaatacccctgcagtttcatatgaatatcctccttag (SEQ ID No. 156) |
| gadC | Δ_gadC_for | atggctacatcagtacagacaggtaaagctaagcagctcacattagtgtaggctggagctgcttc (SEQ ID No. 157) |
| | Δ_gadC_rev | ttagtgtttcttgtcattcatcacaatatagtgtggtgaacgtgccatatgaatatcctccttag (SEQ ID No. 158) |
| sfcA | Δ_sfcA_for | atggaaccaaaaacaaaaaaacagcgttcgctttatatcccttacgtgtaggctggagctgcttc (SEQ ID No. 159) |
| | Δ_sfcA_rev | ttagatggaggtacggcggtagtcgcggtattcggcttgccagaacatatgaatatcctccttag (SEQ ID No. 160) |
| maeB | Δ_maeB_for | atggatgaccagttaaaacaaagtgcacttgatttccatgaatttgtgtaggctggagctgcttc (SEQ ID No. 161) |
| | Δ_maeB_rev | ttacagcggttgggtttgcgcttctaccacggccagcgccaccatcatatgaatatcctccttag (SEQ ID No. 162) |
| ppc | Δ_ppc_for | atgaacgaacaatattccgcattgcgtagtaatgtcagtatgctcgtgtaggctggagctgcttc (SEQ ID No. 163) |
| | Δ_ppc_rev | ttagccggtattacgcatacctgccgcaatcccggcaatagtgaccatatgaatatcctccttag (SEQ ID No. 164) |
| pykA | Δ_pykA_for | atgtccagaaggcttcgcagaacaaaaatcgttaccacgttaggcgtgtaggctggagctgcttc (SEQ ID No. 165) |
| | Δ_pykA_rev | ttactctaccgttaaaatacgcgtggtattagtagaacccacggtcatatgaatatcctccttag (SEQ ID No. 166) |
| pykF | Δ_pykF_for | atgaaaaagaccaaaattgtttgcaccatcggaccgaaaaccgaagtgtaggctggagctgcttc (SEQ ID No. 167) |
| | Δ_pykF_rev | ttacaggacgtgaacagatgcggtgttagtagtgccgctcggtaccatatgaatatcctccttag (SEQ ID No. 168) |
| mgsA | Δ_mgsA_for | atggaactgacgactcgcactttacctgcgcggaaacatattgcggtgtaggctggagctgcttc (SEQ ID No. 169) |
| | Δ_mgsA_rev | ttacttcagacggtccgcgagataacgctgataatcggggatcagcatatgaatatcctccttag (SEQ ID No. 170) |
| iclR | Δ_iclR_for | atggtcgcacccattcccgcgaaacgcggcagaaaaccgccgttgtgtaggctggagctgcttc (SEQ ID No. 171) |
| | Δ_iclR_rev | tcagcgcattccaccgtacgccagcgtcacttccttcgccgctttcatatgaatatcctccttag (SEQ ID No. 172) |
| icd | Δicd_for | atgaaaagtaaagtagttgttccggcacaaggcaagaagatcaccgtgtaggctggagctgcttc (SEQ ID No. 173) |
| | Δicd_rev | ttacatgttttcgatgatcgcgtcaccaaactctgaacatttcagcatatgaatatcctccttag (SEQ ID No. 174) |
| sucA | Δ_sucA_for | atgcagaacagcgctttgaaagcctggttggactcttcttacctcgtgtaggctggagctgcttc (SEQ ID No. 175) |
| | Δ_sucA_rev | ttattcgacgttcagcgcgtcattaaccagatcttgttgctgttttcatatgaatatcctccttag (SEQ ID No. 176) |
| sucB | Δ_sucB_for | atgagtagcgtagatattctggtccctgacctgcctgaatccgtagtgtaggctggagctgcttc (SEQ ID No. 177) |
| | Δ_sucB_rev | ctacacgtccagcagcagacgcgtcggatcttccagcaactctttcatatgaatatcctccttag (SEQ ID No. 178) |
| frdA | Δ_frdA_for | gtgcaaacctttcaagccgatcttgccattgtaggcgccggtggcgtgtaggctggagctgcttc (SEQ ID No. 179) |

TABLE 10-continued

Primers used for gene disruptions. Sequences homologous to target genes are underlined

| Gene | Primer | Sequence |
|---|---|---|
| | Δ_frdA_rev | <u>tcagccattcgccttctccttcttattggctgcttccgccttatc</u>catatgaatatcctccttag (SEQ ID No. 180) |
| frdB | Δ_frdB_for | <u>atggctgagatgaaaaacctgaaaattgaggtggtgcgctataac</u>gtgtaggctggagctgcttc (SEQ ID No. 181) |
| | Δ_frdB_rev | <u>ttagcgtggtttcagggtcgcgataagaaagtctttcgaactttc</u>catatgaatatcctccttag (SEQ ID No. 182) |
| frdC | Δ_frdC_for | <u>atgacgactaaacgtaaaccgtatgtacggccaatgacgtccacc</u>gtgtaggctggagctgcttc (SEQ ID No. 183) |
| | Δ_frdC_rev | <u>ttaccagtacagggcaacaaacaggattacgatggtggcaaccac</u>catatgaatatcctccttag (SEQ ID No. 184) |
| frdD | Δ_frdD_for | <u>atgattaatccaaatccaaagcgttctgacgaaccggtattctgg</u>gtgtaggctggagctgcttc (SEQ ID No. 185) |
| | Δ_frdD_rev | <u>ttagattgtaacgacaccaatcagcgtgacaactgtcaggatagc</u>catatgaatatcctccttag (SEQ ID No. 186) |
| ptsI | Δ_ptsI_for | <u>atgatttcaggcatttttagcatcccgggtatcgctttcggtaaag</u>tgtaggctggagctgcttc (SEQ ID No. 187) |
| | Δ_ptsI_rev | <u>ttagcagattgttttttcttcaatgaacttgttaaccagcgtcat</u>catatgaatatcctccttag (SEQ ID No. 188) |
| ptsG | Δ_ptsG_for | <u>atgtttaagaatgcatttgctaacctgcaaaaggtcggtaaatcgg</u>tgtaggctggagctgcttc (SEQ ID No. 189) |
| | Δ_ptsG_rev | <u>ttagtggttacggatgtactcatccatctcggttttcaggttatc</u>catatgaatatcctccttag (SEQ ID No. 190) |
| lacI | Δ_lacI_for | <u>gtgaaaccagtaacgttatacgatgtcgcagagtatgccggtgtc</u>gtgtaggctggagctgcttc (SEQ ID No. 191) |
| | Δ_lacI_rev | <u>tcactgcccgctttccagtcgggaaacctgtcgtgccagctgcat</u>catatgaatatcctccttag (SEQ ID No. 192) |
| lldD | Δ_lldD_for | <u>atgattatttccgcagccagcgattatcgcgccgcagcgcaacgc</u>gtgtaggctggagctgcttc (SEQ ID No. 193) |
| | Δ_lldD_rev | <u>ctatgccgcattcccttcgccatgggagccagtgccgcaggcaa</u>catatgaatatcctccttag (SEQ ID No. 194) |
| pgi | Δ_pgi_for | <u>atgaaaaacatcaatccaacgcagaccgctgcctggcaggcacta</u>gtgtaggctggagctgcttc (SEQ ID No. 195) |
| | Δ_pgi_rev | <u>ttaaccgcgccacgctttatagcggttaatcagaccattggtcga</u>catatgaatatcctccttag (SEQ ID No. 196) |
| metA | Δ_metA_for | <u>atgccgattcgtgtgccggacgagctacccgccgtcaatttcttg</u>gtgtaggctggagctgcttc (SEQ ID No. 197) |
| | Δ_metA_rev | <u>ttaatccagcgttggattcatgtgccgtagatcgtatggcgtgat</u>catatgaatatcctccttag (SEQ ID No. 198) |
| thrB | Δ_thrB_for | <u>atggttaaagtttatgccccggcttccagtgccaatatgagcgtcg</u>tgtaggctggagctgcttc (SEQ ID No. 199) |
| | Δ_thrB_rev | <u>ttagttttccagtactcgtgcgcccgccgtatccagccggcaaat</u>catatgaatatcctccttag (SEQ ID No. 200) |
| lysA | Δ_lysA_for | <u>atgccacattcactgttcagcaccgataccgatctcaccgccgaa</u>gtgtaggctggagctgcttc (SEQ ID No. 201) |
| | Δ_lysA_rev | <u>ttaaagcaattccagcgccagtaattcttcgatggtctggcgacg</u>catatgaatatcctccttag (SEQ ID No. 202) |
| eda | Δ_eda_for | <u>atgaaaaactggaaaacaagtgcagaatcaatcctgaccaccggc</u>gtgtaggctggagctgcttc (SEQ ID No. 203) |
| | Δ_eda_rev | <u>ctcgatcgggcattttgacttttacagcttagcgccttctacagc</u>catatgaatatcctccttag (SEQ ID No. 204) |
| recA | Δ_recA_for | <u>atggctatcgacgaaaacaaacagaaagcgttggcggcagcact</u>ggtgtaggctggagctgcttc (SEQ ID No. 205) |
| | Δ_recA_rev | <u>ttaaaaatcttcgttagtttctgctacgccttcgctatcatctac</u>catatgaatatcctccttag (SEQ ID No. 206) |
| asd | Δ_asd_for | <u>atgaaaaatgttggttttatcggctggcgcggtatggtcggctccg</u>tgtaggctggagctgcttc (SEQ ID No. 207) |
| | Δ_asd_rev | <u>ttacgccagttgacgaagcatccgacgcagcggctccgcggccccc</u>catatgaatatcctccttag (SEQ ID No. 208) |

TABLE 11

Primer pairs used for verification of gene disruptions

| Deleted gene | Sequence (5' - 3') | |
|---|---|---|
| | Forward primer | Reverse primer |
| K2 for/k1 rev | cggtgccctgaatgaactgc (SEQ ID No. 209) | cagtcatagccgaatagcct (SEQ ID No. 210) |
| ldhA | atacgtgtcccgagcggtag (SEQ ID No. 211) | tacacatcccgccatcagca (SEQ ID No. 212) |
| adhE | Gaagtaaacgggaaaatcaa (SEQ ID No. 213) | Agaagtggcataagaaaacg (SEQ ID No. 214) |
| ackA | ccattggctgaaaattacgc (SEQ ID No. 215) | gttccattgcacggatcacg (SEQ ID No. 216) |
| focA_pflB | atgccgtagaagccgccagt (SEQ ID No. 217) | tgttggtgcgcagctcgaag (SEQ ID No. 218) |
| pta | gcaaatctggtttcatcaac (SEQ ID No. 219) | tcccttgcacaaaacaaagt (SEQ ID No. 220) |
| poxB | ggatttggttctcgcataat (SEQ ID No. 221) | agcattaacggtagggtcgt (SEQ ID No. 222) |
| sad | gctgattctcgcgaataaac (SEQ ID No. 223) | aaaaacgttcttgcgcgtct (SEQ ID No. 224) |
| gabD | tctgtttgtcaccaccccgc (SEQ ID No. 225) | Aagccagcacctggaagcag (SEQ ID No. 226) |
| gadA | aagagctgccgcaggaggat (SEQ ID No. 227) | gccgccctcttaagtcaaat (SEQ ID No. 228) |
| gadB | ggattttagcaatattcgct (SEQ ID No. 229) | cctaatagcaggaagaagac (SEQ ID No. 230) |
| gadC | gctgaactgttgctggaaga (SEQ ID No. 231) | ggcgtgcttttacaactaca (SEQ ID No. 232) |
| sfcA | tagtaaataacccaaccggc (SEQ ID No. 233) | tcagtgagcgcagtgtttta (SEQ ID No. 234) |
| maeB | attaatggtgagagtttgga (SEQ ID No. 235) | tgcttttttttattattcgc (SEQ ID No. 236) |
| ppc | gctttataaaagacgacgaa (SEQ ID No. 237) | gtaacgacaattccttaagg (SEQ ID No. 238) |
| pykA | tttatatgcccatggttttct (SEQ ID No. 239) | atctgttagaggcggatgat (SEQ ID No. 240) |
| pykF | ctggaacgttaaatctttga (SEQ ID No. 241) | ccagtttagtagctttcatt (SEQ ID No. 242) |
| iclR | gatttgttcaacattaactcatcgg (SEQ ID No. 243) | tgcgattaacagacaccctt (SEQ ID No. 244) |
| mgsA | tctcaggtgctcacagaaca (SEQ ID No. 245) | tatggaagaggcgctactgc (SEQ ID No. 246) |
| icd | cgacctgctgcataaacacc (SEQ ID No. 247) | tgaacgctaaggtgattgca (SEQ ID No. 248) |
| sucA | acgtagacaagagctcgcaa (SEQ ID No. 249) | catcacgtacgactgcgtcg (SEQ ID No. 250) |
| sucB | tgcaactttgtgctgagcaa (SEQ ID No. 251) | tatcgcttccgggcattgtc (SEQ ID No. 252) |
| frdA | Aaatcgatctcgtcaaatttcagac (SEQ ID No. 253) | aggaaccacaaatcgccata (SEQ ID No. 254) |
| frdB | gacgtgaagattactacgct (SEQ ID No. 255) | agttcaatgctgaaccacac (SEQ ID No. 256) |
| frdC | tagccgcgaccacggtaagaaggag (SEQ ID No. 257) | cagcgcatcacccggaaaca (SEQ ID No. 258) |

TABLE 11-continued

Primer pairs used for verification of gene disruptions

| Deleted gene | Sequence (5' - 3') Forward primer | Reverse primer |
|---|---|---|
| frdD | atcgtgatcattaacctgat (SEQ ID No. 259) | ttaccctgataaattaccgc (SEQ ID No. 260) |
| ptsG | ccatccgttgaatgagtttt (SEQ ID No. 261) | tggtgttaactggcaaaatc (SEQ ID No. 262) |
| ptsI | gtgacttccaacggcaaaag (SEQ ID No. 263) | ccgttggtttgatagcaata (SEQ ID No. 264) |
| lacI | Gaatctggtgtatatggcga (SEQ ID No. 265) | Tcttcgctattacgccagct (SEQ ID No. 266) |
| lldD | Cgtcagcggatgtatctggt (SEQ ID No. 267) | Gcggaatttctggttcgtaa (SEQ ID No. 268) |
| pgi | Ttgtcaacgatggggtcatg (SEQ ID No. 269) | Aaaaatgccgacataacgtc (SEQ ID No. 270) |
| lysA | Tctcaaagcgcgcaagttcg (SEQ ID No. 271) | Ggtattgatgtaccgggtgagatt (SEQ ID No. 272) |
| metA | Tcgacagaacgacaccaaat (SEQ ID No. 273) | Cactgtgaacgaaggatcgt (SEQ ID No. 274) |
| thrB | Tgttggcaatattgatgaag (SEQ ID No. 275) | Gacatcgctttcaacattgg (SEQ ID No. 276) |
| eda | Gacagacaggcgaactgacg (SEQ ID No. 277) | Gcgcagatttgcagattcgt (SEQ ID No. 278) |
| recA | Tggcggcagtgaagagaagc (SEQ ID No. 279) | Gcaataacgcgctcgtaatc (SEQ ID No. 280) |
| asd | Acaaagcaggataagtcgca (SEQ ID No. 281) | Gacttcaggtaaggctgtga (SEQ ID No. 282) |
| rhtA | CAGAGAACTGCGTAAGTATTACGCA (SEQ ID No. 283) | TAGTGGTAACAAGCGTGAAAAACAA (SEQ ID No. 284) |
| rhtB | ATGAAGACTCCGTAAACGTTTCCCC (SEQ ID No. 285) | CAAAAATAGACACACCGGGAGTTCA (SEQ ID No. 286) |

The plasmid co-expressing aspartate kinase, aspartate semialdehyde dehydrogenase, and homoserine dehydrogenase (pACT3-op-HMS1) was transformed together with the plasmid expressing the homoserine transaminase and the OHB reductase (pEXT20-DHB) into the optimized host strains. Transformants were selected on solid LB medium containing chloramphenicol (25 μg/mL) and ampicillin (100 μg/mL). Non-exclusive examples of constructed strains are listed in Table 12.

TABLE 12

Examples of strains constructed for DHB production

| Strain | Relevant Genotype |
|---|---|
| MG1655 | Wild-type |
| ECE73 | ΔldhA ΔadhE ΔmetA ΔthrB |
| ECE74 | ΔldhA ΔadhE ΔmetA ΔthrB pACT3-op-HMS1 |
| ECE75 | ΔldhA ΔadhE ΔmetA ΔthrB pEXT20-DHB |
| ECE76 | ΔldhA ΔadhE ΔmetA ΔthrB pACT3-op-HMS1 pEXT20-DHB |
| ECE77 | ΔldhA ΔadhE ΔmetA ΔthrB ΔlldD pACT3-op-HMS1 pEXT20-DHB |
| ECE78 | ΔldhA ΔadhE ΔmetA ΔthrB ΔrhtB pACT3-op-HMS1 pEXT20-DHB |

It is understood that removal of the lacI gene from the backbone of the above described plasmids along with the genomic deletion of lacI in the host strain may render protein expression from above described plasmids constitutive.

Example 9: Demonstration of the Zymotic Production of DHB Via the Homoserine-OHB Pathway Strains and Cultivation Conditions:

Experiments were carried out with strains listed in Table 12. All cultivations were carried out at 37° C. on an Infors rotary shaker running at 170 rpm. Overnight cultures (3 mL medium in test tube) were inoculated from glycerol stocks and used to adjust an initial $OD_{600}$ of 0.05 in 100 mL growth cultures cultivated in 500 mL shake flasks. IPTG was added at a concentration of 1 mmol/L when $OD_{600}$ in the growth cultures reached 0.8. One liter culture medium contained, 20 g glucose, 18 g $Na_2HPO_4*12\ H_2O$, 3 g $KH_2PO_4$, 0.5 g NaCl, 2 g $NH_4Cl$, 0.5 g $MgSO_4*7\ H_2O$, 0.015 $CaCl_2*2\ H_2O$, 1 mL of 0.06 mol/L $FeCl_3$ stock solution prepared in 100 times diluted concentrated HCl, 2 mL of 10 mM thiamine HCl stock solution, 20 g MOPS and 1 mL of trace element solution (containing per liter: 0.04 g $Na_2EDTA*2H_2O$, 0.18 g $CoCl_2*6\ H_2O$, $ZnSO4*7\ H_2O$, 0.04 g $Na_2MoO4*2\ H_2O$, 0.01 g $H_3BO_3$, 0.12 g $MnSO_4*H_2O$, 0.12 g $CuCl_2*H2O$.). Medium pH was adjusted to 7 and medium was filter-sterilized. The antibiotics kanamycin sulphate, ampicillin, and chloramphenicol were added at concentrations of 50 mg/L, 100 mg/L, and 25 mg/L, respectively, when necessary.

Estimation of DHB Concentration by LC-MS Analyses:

Liquid anion exchange chromatography was performed on an ICS-3000 system from Dionex (Sunnyvale, USA) equipped with an automatic eluent (KOH) generator system (RFIC, Dionex), and an autosampler (AS50, Dionex) holding the samples at 4° C. Analytes were separated on an IonPac AS11 HC (250×2 mm, Dionex) column protected by an AG11 HC (50×2 mm, Dionex) pre-column. Column temperature was held at 25° C., flow rate was fixed at 0.25 mL/min, and analytes were eluted applying the KOH gradient described earlier (Groussac E, Ortiz M & Francois J (2000): Improved protocols for quantitative determination of metabolites from biological samples using high performance ionic-exchange chromatography with conductimetric and pulsed amperometric detection. Enzyme. Microb. Technol. 26, 715-723). Injected sample volume was 15 µL. For background reduction, an ASRS ultra II (2 mm, external water mode, 75 mA) anion suppressor was used. Analytes were quantified using a mass-sensitive detector (MSQ Plus, Thermo) running in ESI mode (split was ⅓, nitrogen pressure was 90 psi, capillary voltage was 3.5 kV, probe temperature was 450° C.).

Results:

After 24 h cultivation, the DHB concentration in the supernatant of different strains was quantified by LC-MS analyses. The strains ECE73, ECE74, ECE75, and ECE76 had produced 0 mg/L, 3.7 mg/L, 0.67 mg/L, and 11.9 mg/L of DHB, respectively.

REFERENCES

Chambellon, E., Rijnen, L., Lorquet, F., Gitton, C., van Hylckama Vlieg, J. E. T., Wouters, J. A. & Yvon, M. (2009). The D-2-hydroxyacid dehydrogenase incorrectly annotated PanE is the sole reduction system for branched-chain 2-keto acids in Lactococcus lactis. J. Bacteriol 191, 873-881.

Cherepanov, P. P. & Wackernagel, W. (1995). Gene disruption in Escherichia coli: TcR and KmR cassettes with the option of Flp-catalyzed excision of the antibiotic-resistance determinant. Gene 158, 9-14.

Datsenko, K. A. & Wanner, B. L. (2000). One-step inactivation of chromosomal genes in Escherichia coli K-12 using PCR products. Proc. Natl. Acad. Sci. U.S.A. 97, 6640-6645.

Dykxhoorn, D. M., St Pierre, R. & Linn, T. (1996). A set of compatible tac promoter expression vectors. Gene 177, 133-136.

Hädicke, O. & Klamt, S. (2010). CASOP: a computational approach for strain optimization aiming at high productivity. J. Biotechnol 147, 88-101.

Klamt, S., Saez-Rodriguez, J. & Gilles, E. D. (2007). Structural and functional analysis of cellular networks with CellNetAnalyzer. BMC Syst Biol 1, 2.

Rothman, S. C. & Kirsch, J. F. (2003). How does an enzyme evolved in vitro compare to naturally occurring homologs possessing the targeted function? Tyrosine aminotransferase from aspartate aminotransferase. J. Mol. Biol 327, 593-608.

Sambrook, J., Fritsch, E. F. & Maniatis, T. (1989). Molecular Cloning: A Laboratory Manual, 2 éd. Cold Spring Harbor: Cold Spring Harbor Laboratory Press.

Schuster, S., Dandekar, T. & Fell, D. A. (1999). Detection of elementary flux modes in biochemical networks: a promising tool for pathway analysis and metabolic engineering. Trends Biotechnol 17, 53-60.

Wellner, D. & Lichtenberg, L. A. (1971). Assay of amino acid oxidase. Methods in Enzymology 17, Part B, 593-596.

The invention claimed is:

1. A method for the preparation of 2,4-dihydroxybutyrate from homoserine comprising:

deaminating homoserine to form 2-oxo-4-hydroxybutyrate (OHB), where the deamination of homoserine is catalyzed by an enzyme having homoserine transaminase activity, wherein the enzyme having homoserine transaminase activity either is encoded by the sequence set forth in SEQ ID NO: 59, SEQ ID NO: 61, SEQ ID NO: 63, SEQ ID NO: 65, SEQ ID NO: 67 or SEQ ID NO: 69, or is selected from SEQ ID NO: 60, SEQ ID NO: 62, SEQ ID NO: 64, SEQ ID NO: 66, SEQ ID NO: 68 or SEQ ID NO: 70 or is selected from any sequence sharing a sequence identity of at least 90% with SEQ ID NO: 60, SEQ ID NO: 62, SEQ ID NO: 64, SEQ ID NO: 66, SEQ ID NO: 68 or SEQ ID NO: 70, and the enzyme having homoserine transaminase activity is produced via a transformed host microorganism that comprises a first chimeric gene including a first nucleic acid sequence encoding the enzyme having homoserine transaminase activity for converting the primary amino acid group of homoserine to a carbonyl group to obtain OHB; and reducing the OHB to form 2,4-dihydroxybutyrate (2,4-DHB), where the reduction of OHB is catalyzed by an enzyme having OHB reductase activity, wherein
the enzyme having OHB reductase activity is an OHB reductase that is selected from the group consisting of (D)-lactate dehydrogenase from *Escherichia coli* (SEQ ID NO: 4), (L)-lactate dehydrogenase from *Lactococcus lactis* (SEQ ID NO: 6), the two isoforms of (L)-lactate dehydrogenase from *Oryctalagus cuniculus* (SEQ ID NO: 12 and SEQ ID NO: 14), (L)-lactate dehydrogenase from *Geobacillus stearothermophilus* (SEQ ID NO: 10), (L)-lactate dehydrogenase from *Bacillus subtilis* (SEQ ID NO: 8), (L)-malate dehydrogenase from *Escherichia coli* (SEQ ID NO: 2), branched chain (D)-2-hydroxyacid dehydrogenase from *Lactococcus lactis*, and dehydrogenases having an amino acid sequence sharing a sequence identity of at least 90% with at least one of said sequences, and
the enzyme having OHB reductase activity being produced via the transformed host microorganism, which further comprises a second chimeric gene including a second nucleic acid sequence encoding the enzyme having OHB reductase activity for reducing OHB to 2,4-DHB.

2. The method of claim 1 wherein the OHB reductase is
a lactate dehydrogenase comprising at least one mutation in position V17, Q85, E89, I1226, or A222, said positions being defined by reference to the L-*Lactis* LdhA (SEQ ID NO: 6); or
a malate dehydrogenase comprising at least one mutation in position A112, R81, M85, D86, V93, G179, T211, or M227, said positions being defined by reference to the *E. coli* Mdh (SEQ ID NO: 2).

3. A method for the preparation of 2,4-dihydroxybutyrate from homoserine comprising:
deaminating homoserine to form 2-oxo-4-hydroxybutyrate (OHB), where the deamination of homoserine is catalyzed by an enzyme having homoserine transaminase activity, wherein
the enzyme having homoserine transaminase activity either
is encoded by the sequence set forth in SEQ ID NO: 59, SEQ ID NO: 61, SEQ ID NO: 63, SEQ ID NO: 65, SEQ ID NO: 67 or SEQ ID NO: 69, or
is selected from SEQ ID NO: 60, SEQ ID NO: 62, SEQ ID NO: 64, SEQ ID NO: 66, SEQ ID NO: 68 or SEQ ID NO: 70 or is selected from any sequence sharing a sequence identity of at least 90% with SEQ ID NO: 60, SEQ ID NO: 62, SEQ ID NO: 64, SEQ ID NO: 66, SEQ ID NO: 68 or SEQ ID NO: 70, and
the enzyme having homoserine transaminase activity is produced via a transformed host microorganism that comprises a first chimeric gene including a first nucleic acid sequence encoding the enzyme having homoserine transaminase activity for converting the primary amino acid group of homoserine to a carbonyl group to obtain OHB; and
reducing the OHB to form 2,4-dihydroxybutyrate (2,4-DHB), where the reduction of OHB is catalyzed by an enzyme having OHB reductase activity, wherein the enzyme having OHB reductase activity is an OHB reductase that either
is selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 288, SEQ ID NO: 30, SEQ ID NO: 32, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116 or SEQ ID NO: 118 or is selected from any sequence sharing a sequence identity of at least 90% with SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 288, SEQ ID NO: 30, SEQ ID NO: 32, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116 or SEQ ID NO: 118, or
is encoded by a nucleic acid sequence selected from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 287, SEQ ID NO: 29, SEQ ID NO: 31, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115 or SEQ ID NO: 117.

4. A modified microorganism for the preparation of 2,4-DHB (2,4-dihydroxybutyrate) from homoserine via a two-step pathway comprising:
deaminating homoserine to form 2-oxo-4-hydroxybutyrate (OHB), where the deamination of homoserine is catalyzed by an enzyme having homoserine transaminase activity, wherein
the enzyme having homoserine transaminase activity either
is encoded by the sequence set forth in SEQ ID NO: 59, SEQ ID NO: 61, SEQ ID NO: 63, SEQ ID NO: 65, SEQ ID NO: 67 or SEQ ID NO: 69, or
is selected from SEQ ID NO: 60, SEQ ID NO: 62, SEQ ID NO: 64, SEQ ID NO: 66, SEQ ID NO: 68 or SEQ ID NO: 70 or is selected from any sequence sharing a sequence identity of at least 90% with SEQ ID NO: 60, SEQ ID NO: 62, SEQ ID NO: 64, SEQ ID NO: 66, SEQ ID NO: 68 or SEQ ID NO: 70, and
reducing the OHB to form 2,4-DHB, where the reduction of OHB is catalyzed by an enzyme having OHB reductase activity, wherein
the enzyme having OHB reductase activity is an OHB reductase that is selected from the group consisting of (D)-lactate dehydrogenase from *Escherichia coli* (SEQ ID NO: 4), (L)-lactate dehydrogenase from *Lactococcus lactis* (SEQ ID NO: 6), the two isoforms of (L)-lactate dehydrogenase from *Oryctalagus cuniculus* (SEQ ID NO: 12 and SEQ ID NO: 14), (L)-lactate dehydrogenase from *Geobacillus stearothermophilus* (SEQ ID NO: 10), (L)-lactate dehydrogenase from *Bacillus subtilis* (SEQ ID NO: 8), (L)-malate dehydrogenase from *Escherichia coli* (SEQ ID NO: 2), branched chain (D)-2-hydroxyacid dehydrogenase from *Lactococcus lactis*, and dehydrogenases having an amino acid sequence sharing a sequence identity of at least 90% with at least one of said sequences; wherein
the modified microorganism is a host microorganism that has been transformed to enhance production of 2,4-DHB compared to a non-transformed host microorganism, the transformed microorganism comprising:
a first chimeric gene including a first nucleic acid sequence encoding the enzyme having homoserine transaminase activity for converting the primary amino acid group of homoserine to a carbonyl group to obtain OHB, and a second chimeric gene including a second nucleic acid sequence encoding the enzyme having OHB reductase activity for reducing OHB to 2,4-DHB.

5. The modified microorganism according to claim 4 wherein transformed host microorganism has been further transformed to enhance production of homoserine compared to the non-transformed host microorganism.

6. The modified microorganism according to claim 5, wherein the enhanced production of homoserine comprises overexpressing one or more additional enzymes selected from the group consisting of aspartate kinase, aspartate semialdehyde dehydrogenase and homoserine dehydrogenase, wherein the overexpression of said one or more enzymes being realized by expressing the enzymes from a multicopy plasmid.

7. The modified microorganism of claim 4, wherein the modified microorganism is a bacterium, a yeast, or a fungus.

8. The modified microorganism of claim 4 wherein
the expression of at least of one the enzymatic activities chosen among phosphoenolpyruvate carboxylase, phosphoenolpyruvate carboxykinase, isocitrate lyase, pyruvate carboxylase, and hexose symporter permease is increased, or at least one of the enzymatic activities chosen among lactate dehydrogenase, alcohol dehydrogenase, acetate kinase, phosphate acetyltransferase, pyruvate oxidase, isocitrate lyase, fumarase, 2-oxoglutarate dehydrogenase, pyruvate kinase, malic enzyme, phosphoglucose isomerase, phosphoenolpyruvate carboxylase, phosphoenolpyruvate carboxykinase, pyruvate-formate lyase, succinic semialdehyde dehydrogenase, sugar-transporting phosphotransferase, ketohydroxyglutarate aldolase, homoserine-O-succinyl transferase, homoserine kinase, homoserine efflux transporter, diaminopimelate decarboxylase, and/or methylglyoxal synthase is decreased.

9. The modified microorganism according to claim 7, the modified microorganism being *Escherichia coli*, which
overexpresses at least one of the genes chosen among ppc (phosphoenol pyruvate carboxylase), pck, aceA, galP, asd, thrA, metL, lysC all *E coli*; pycA from *L lactis*, and/or has at least one of the genes deleted chosen among IdhA, adhE, ackA, pta, poxB, focA, pflB, sad, gabABC, sfcA, maeB, ppc, pykA, pykF, mgsA, sucAB, ptsI, ptsG, pgi, fumABCaldA, HdD, icIR, metA, thrB, lysA, eda, rthA, rthB, and rthC.

10. A method of production of 2,4-DHB comprising the steps of
culturing the modified microorganism of claim 4 in an appropriate culture medium,
recovering 2,4-DHB from the culture medium.

11. The method of claim 10 wherein the 2,4-DHB is further purified.

12. The method of claim 1, wherein
the enzyme having homoserine transaminase activity either
is encoded by the sequence set forth in SEQ ID NO: 59, SEQ ID NO: 61, SEQ ID NO: 63, SEQ ID NO: 65, SEQ ID NO: 67 or SEQ ID NO: 69, or
is selected from SEQ ID NO: 60, SEQ ID NO: 62, SEQ ID NO: 64, SEQ ID NO: 66, SEQ ID NO: 68 or SEQ ID NO: 70 or is selected from any sequence sharing a sequence identity of at least 95% with SEQ ID NO: 60, SEQ ID NO: 62, SEQ ID NO: 64, SEQ ID NO: 66, SEQ ID NO: 68 or SEQ ID NO: 70, and the enzyme having OHB reductase activity is selected from the group consisting of (D)-lactate dehydrogenase from *Escherichia coli* (SEQ ID NO: 4), (L)-lactate dehydrogenase from *Lactococcus lactis* (SEQ ID NO: 6), the two isoforms of (L)-lactate dehydrogenase from Oryctalagus *cuniculus* (SEQ ID NO: 12 and SEQ ID NO: 14), (L)-lactate dehydrogenase from *Geobacillus stearothermophilus* (SEQ ID NO: 10), (L)-lactate dehydrogenase from *Bacillus subtilis* (SEQ ID NO: 8), (L)-malate dehydrogenase from *Escherichia coli* (SEQ ID NO: 2), branched chain (D)-2-hydroxyacid dehydrogenase from *Lactococcus lactis*, and dehydrogenases having an amino acid sequence sharing a sequence identity of at least 95% with at least one of said sequences.

13. The method of claim 12, wherein any amino acid substitutions are conservative amino acid substitutions in which each substituted amino acid is replaced by another biologically similar amino acid.

14. The method of claim 1, wherein
the enzyme having homoserine transaminase activity is selected from SEQ ID NO: 60, SEQ ID NO: 62, SEQ ID NO: 64, SEQ ID NO: 66, SEQ ID NO: 68 or SEQ ID NO: 70 or is selected from any sequence sharing a sequence identity of at least 98% with SEQ ID NO: 60, SEQ ID NO: 62, SEQ ID NO: 64, SEQ ID NO: 66, SEQ ID NO: 68 or SEQ ID NO: 70, and the enzyme having OHB reductase activity is selected from the group consisting of (D)-lactate dehydrogenase from *Escherichia coli* (SEQ ID NO: 4), (L)-lactate dehydrogenase from *Lactococcus lactis* (SEQ ID NO: 6), the two isoforms of (L)-lactate dehydrogenase from Oryctalagus *cuniculus* (SEQ ID NO: 12 and SEQ ID NO: 14), (L)-lactate dehydrogenase from *Geobacillus stearothermophilus* (SEQ ID NO: 10), (L)-lactate dehydrogenase from *Bacillus subtilis* (SEQ ID NO: 8), (L)-malate dehydrogenase from *Escherichia coli* (SEQ ID NO: 2), branched chain (D)-2-hydroxyacid dehydrogenase from *Lactococcus lactis*, dehydrogenases having an amino acid sequence sharing a sequence identity of at least 98% with at least one of said sequences.

15. The method of claim 14, wherein any amino acid substitutions are conservative amino acid substitutions in which each substituted amino acid is replaced by another biologically similar amino acid.

16. The method of claim 1, wherein
the enzyme having homoserine transaminase activity either
is encoded by the sequence set forth in SEQ ID NO: 59, SEQ ID NO: 61, SEQ ID NO: 63, SEQ ID NO: 65, SEQ ID NO: 67 or SEQ ID NO: 69, or
is selected from SEQ ID NO: 60, SEQ ID NO: 62, SEQ ID NO: 64, SEQ ID NO: 66, SEQ ID NO: 68 or SEQ ID NO: 70, and the enzyme having OHB reductase activity is selected from the group consisting of (D)-lactate dehydrogenase from *Escherichia coli* (SEQ ID NO: 4), (L)-lactate dehydrogenase from *Lactococcus lactis* (SEQ ID NO: 6), the two isoforms of (L)-lactate dehydrogenase from Oryctalagus *cuniculus* (SEQ ID NO: 12 and SEQ ID NO: 14), (L)-lactate dehydrogenase from *Geobacillus stearothermophilus* (SEQ ID NO: 10), (L)-lactate dehydrogenase from *Bacillus subtilis* (SEQ ID NO: 8), and (L)-malate dehydrogenase from *Escherichia coli* (SEQ ID NO: 2).

17. The method of claim 1, wherein the enzyme having homoserine transaminase activity is selected from the group consisting of SEQ ID NO: 60, SEQ ID NO: 62, SEQ ID NO: 64, SEQ ID NO: 66, SEQ ID NO: 68 or SEQ ID NO: 70, and the enzyme having OHB reductase activity is selected from the group consisting of (D)-lactate dehydrogenase from *Escherichia coli* (SEQ ID NO: 4), (L)-lactate dehydrogenase from *Lactococcus lactis* (SEQ ID NO: 6), the two isoforms of (L)-lactate dehydrogenase from Oryctalagus *cuniculus* (SEQ ID NO: 12 and SEQ ID NO: 14), (L)-lactate dehydrogenase from *Geobacillus stearothermophilus* (SEQ ID NO: 10), (L)-lactate dehydrogenase from *Bacillus subtilis* (SEQ ID NO: 8), and (L)-malate dehydrogenase from *Escherichia coli* (SEQ ID NO: 2).

* * * * *

UNITED STATES PATENT AND TRADEMARK OFFICE
CERTIFICATE OF CORRECTION

PATENT NO. : 10,570,422 B2
APPLICATION NO. : 14/414331
DATED : February 25, 2020
INVENTOR(S) : Thomas Walther et al.

It is certified that error appears in the above-identified patent and that said Letters Patent is hereby corrected as shown below:

In the Claims

In Claim 1 (Column 196, Line 66), change:
"primary amino acid group"
To:
--primary amino group--

In Claim 2 (Column 197, Line 32), change:
"A112"
To:
--I12--

Signed and Sealed this
First Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 288

<210> SEQ ID NO 1
<211> LENGTH: 939
<212> TYPE: DNA
<213> ORGANISM: Escherichia coli

<400> SEQUENCE: 1

```
atgaaagtcg cagtcctcgg cgctgctggc ggtattggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg tttttctggt     180
gaagatgcga ctccggcgct ggaaggcgca gatgtcgttc ttatctctgc aggcgtagcg     240
cgtaaaccgg gtatggatcg ttccgacctg tttaacgtta acgccggcat cgtgaaaaac     300
ctggtacagc aagttgcgaa aacctgcccg aaagcgtgca ttggtattat cactaacccg     360
gttaacacca cagttgcaat tgctgctgaa gtgctgaaaa aagccggtgt ttatgacaaa     420
```

-continued

```
aacaaactgt tcggcgttac cacgctggat atcattcgtt ccaacacctt tgttgcggaa    480
ctgaaaggca acagccagg cgaagttgaa gtgccggtta ttggcggtca ctctggtgtt    540
accattctgc cgctgctgtc acaggttcct ggcgttagtt ttaccgagca ggaagtggct    600
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt    720
gcactgcagg gcgaacaagg cgttgtcgaa tgtgcctacg ttgaaggcga cggtcagtac    780 gcccgttct  tctctcaacc gctgctgctg gtaaaaacg  gcgtggaaga gcgtaaatct    840
atcggtaccc tgagcgcatt tgaacagaac gcgctggaag gtatgctgga tacgctgaag    900
aaagatatcg ccctgggcga agagttcgtt aataagtaa                          939
```

<210> SEQ ID NO 2
<211> LENGTH: 312
<212> TYPE: PRT
<213> ORGANISM: Escherichia coli

<400> SEQUENCE: 2

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
                20                  25                  30

Tyr Asp Ile Ala Pro Val Thr Pro Gly Val Ala Val Asp Leu Ser His
            35                  40                  45

Ile Pro Thr Ala Val Lys Ile Lys Gly Phe Ser Gly Glu Asp Ala Thr
        50                  55                  60

Pro Ala Leu Glu Gly Ala Asp Val Val Leu Ile Ser Ala Gly Val Ala
65                  70                  75                  80

Arg Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
                100                 105                 110

Cys Ile Gly Ile Ile Thr Asn Pro Val Asn Thr Thr Val Ala Ile Ala
            115                 120                 125

Ala Glu Val Leu Lys Lys Ala Gly Val Tyr Asp Lys Asn Lys Leu Phe
        130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
        275                 280                 285
```

Gln Asn Ala Leu Glu Gly Met Leu Asp Thr Leu Lys Lys Asp Ile Ala
    290                 295                 300

Leu Gly Glu Glu Phe Val Asn Lys
305                 310

<210> SEQ ID NO 3
<211> LENGTH: 990
<212> TYPE: DNA
<213> ORGANISM: Escherichia coli

<400> SEQUENCE: 3

```
atgaaactcg ccgtttatag cacaaaacag tacgacaaga agtacctgca acaggtgaac    60
gagtcctttg gctttgagct ggaattttt gactttctgc tgacggaaaa aaccgctaaa    120
actgccaatg gctgcgaagc ggtatgtatt ttcgtaaacg atgacggcag ccgcccggtg   180
ctggaagagc tgaaaaagca cggcgttaaa tatatcgccc tgcgctgtgc cggtttcaat   240
aacgtcgacc ttgacgcggc aaaagaactg gggctgaaag tagtccgtgt tccagcctat   300
gatccagagg ccgttgctga cacgccatc ggtatgatga tgacgctgaa ccgccgtatt   360
caccgcgcgt atcagcgtac ccgtgatgct aacttctctc tggaaggtct gaccggcttt   420
actatgtatg caaaacggc aggcgttatc ggtaccggta aaatcggtgt ggcgatgctg   480
cgcattctga aaggttttgg tatgcgtctg ctggcgttcg atccgtatcc aagtgcagcg   540
gcgctggaac tcggtgtgga gtatgtcgat ctgccaaccc tgttctctga atcagacgtt   600
atctctctgc actgcccgct gacaccggaa aactatcatc tgttgaacga agccgccttc   660
gaacagatga aaaatggcgt gatgatcgtc aataccagtc gcggtgcatt gattgattct   720
caggcagcaa ttgaagcgct gaaaaatcag aaaattggtt cgttgggtat ggacgtgtat   780
gagaacgaac gcgatctatt ctttgaagat aaatccaacg acgtgatcca ggatgacgta   840
ttccgtcgcc tgtctgcctg ccacaacgtg ctgtttaccg ggcaccaggc attcctgaca   900
gcagaagctc tgaccagtat ttctcagact acgctgcaaa acttaagcaa tctggaaaaa   960
ggcgaaacct gcccgaacga actggtttaa                                    990
```

<210> SEQ ID NO 4
<211> LENGTH: 329
<212> TYPE: PRT
<213> ORGANISM: Escherichia coli

<400> SEQUENCE: 4

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
                20                  25                  30

Leu Leu Thr Glu Lys Thr Ala Lys Thr Ala Asn Gly Cys Glu Ala Val
            35                  40                  45

Cys Ile Phe Val Asn Asp Asp Gly Ser Arg Pro Val Leu Glu Glu Leu
        50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg

```
                   115                 120                 125
Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325

<210> SEQ ID NO 5
<211> LENGTH: 978
<212> TYPE: DNA
<213> ORGANISM: Lactococcus lactis

<400> SEQUENCE: 5
atggctgata acaacgtaa aaaagttatc cttgtaggtg acggtgctgt aggttcatca      60
tacgcttttg ctcttgtaaa ccaagggatt gcacaagaat taggaattgt tgaccttttt     120
aaagaaaaaa ctcaaggaga tgcagaagac ctttctcatg ccttggcatt tacttcacct    180
aaaaagattt actctgcaga ctactctgat gcaagcgacg ctgacctcgt agtcttgact    240
tctggtgctc cacaaaaacc aggtgaaact cgtcttgacc ttgttgaaaa aaatcttcgt    300
atcactaaag atgttgtcac taaaattgtt gcttcaggtt caaggaat cttccttgtt      360 gctgctaacc cagttgatat cttgacatac gctacttgga aattctcagg tttccctaaa    420
aaccgcgttg taggttcagg tacttcactt gatactgcac gtttccgtca agcattggca    480
gaaaaagttg atgttgacgc tcgttcaatc cacgcataca tcatgggtga acacggtgac    540
tcagaatttg ccgtttggtc acacgctaac gttgctggtg ttaaattgga caatggttc    600 caagaaaatg actaccttaa cgaagctgaa atcgttgaat gtttgaatc tgtacgtgat    660 gctgcttact caatcatcgc taaaaaaggt gcaacattct atggtgtcgc tgtagctctt    720
gctcgtatta ctaaagcaat tcttgatgat gaacatgcag tacttccagt atcagtattc    780
caagatggac aatatggcgt aagcgactgc taccttggtc aaccagctgt agttggtgct    840
gaaggtgttg ttaacccaat ccacattcca ttgaatgatg ctgaaatgca aaaaatggaa    900
```

```
gcttctggtg ctcaattgaa agcaatcatt gacgaagctt tgctaaaga agaatttgct    960 tctgcagtta aaactaa                                                  978
```

<210> SEQ ID NO 6
<211> LENGTH: 325
<212> TYPE: PRT
<213> ORGANISM: Lactococcus lactis

<400> SEQUENCE: 6

```
Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
            20                  25                  30

Glu Leu Gly Ile Val Asp Leu Phe Lys Glu Lys Thr Gln Gly Asp Ala
        35                  40                  45

Glu Asp Leu Ser His Ala Leu Ala Phe Thr Ser Pro Lys Lys Ile Tyr
    50                  55                  60

Ser Ala Asp Tyr Ser Asp Ala Ser Asp Ala Asp Leu Val Val Leu Thr
65                  70                  75                  80

Ser Gly Ala Pro Gln Lys Pro Gly Glu Thr Arg Leu Asp Leu Val Glu
                85                  90                  95

Lys Asn Leu Arg Ile Thr Lys Asp Val Val Thr Lys Ile Val Ala Ser
            100                 105                 110

Gly Phe Lys Gly Ile Phe Leu Val Ala Ala Asn Pro Val Asp Ile Leu
        115                 120                 125

Thr Tyr Ala Thr Trp Lys Phe Ser Gly Phe Pro Lys Asn Arg Val Val
    130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
        195                 200                 205

Ala Glu Ile Val Glu Leu Phe Glu Ser Val Arg Asp Ala Ala Tyr Ser
    210                 215                 220

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp His Ala Val Leu Pro
                245                 250                 255

Val Ser Val Phe Gln Asp Gly Gln Tyr Gly Val Ser Asp Cys Tyr Leu
            260                 265                 270

Gly Gln Pro Ala Val Val Gly Ala Glu Gly Val Val Asn Pro Ile His
        275                 280                 285

Ile Pro Leu Asn Asp Ala Glu Met Gln Lys Met Glu Ala Ser Gly Ala
    290                 295                 300

Gln Leu Lys Ala Ile Ile Asp Glu Ala Phe Ala Lys Glu Glu Phe Ala
305                 310                 315                 320

Ser Ala Val Lys Asn
                325
```

<210> SEQ ID NO 7
<211> LENGTH: 966
<212> TYPE: DNA

<213> ORGANISM: Bacillus subtilis

<400> SEQUENCE: 7

```
atgatgaaca acatgtaaa taaagtagct ttaatcggag cgggttttgt tggaagcagt        60
tatgcatttg cgttaattaa ccaaggaatc acagatgagc ttgtggtcat tgatgtaaat      120
aaagaaaaag caatgggcga tgtgatggat ttaaaccacg gaaaggcgtt tgcgccacaa      180
ccggtcaaaa catcttacgg aacatatgaa gactgcaagg atgctgatat tgtctgcatt      240
tgcgccggag caaaccaaaa acctggtgag acacgccttg aattagtaga aagaacttg       300
aagattttca aaggcatcgt tagtgaagtc atggcgagcg gatttgacgg cattttctta      360
gtcgcgacaa atccggttga tatcctgact tacgcaacat ggaaattcag cggcctgcca      420
aaagagcggg tgattggaag cggcacaaca cttgattctg cgagattccg tttcatgctg      480
agcgaatact ttggcgcagc gcctcaaaac gtacacgcgc atattatcgg agagcacggc      540
gacacagagc ttcctgtttg gagccacgcg aatgtcggcg tgtgccggt cagtgaactc       600
gttgagaaaa acgatgcgta caaacaagag gagctggacc aaattgtaga tgatgtgaaa      660
aacgcagctt accatatcat tgagaaaaaa ggcgcgactt attatggggt tgcgatgagt      720
cttgctcgca ttacaaaagc cattcttcat aatgaaaaca gcatattaac tgtcagcaca      780
tatttggacg ggcaatacgg tgcagatgac gtgtacatcg gtgtgccggc tgtcgtgaat      840
cgcggaggga tcgcaggtat cactgagctg aacttaaatg agaaagaaaa agaacagttc      900
cttcacagcg ccggcgtcct taaaaacatt ttaaaacctc attttgcaga caaaaagtc      960
aactaa                                                                  966
```

<210> SEQ ID NO 8
<211> LENGTH: 321
<212> TYPE: PRT
<213> ORGANISM: Bacillus subtilis

<400> SEQUENCE: 8

```
Met Met Asn Lys His Val Asn Lys Val Ala Leu Ile Gly Ala Gly Phe
1               5                   10                  15

Val Gly Ser Ser Tyr Ala Phe Ala Leu Ile Asn Gln Gly Ile Thr Asp
            20                  25                  30

Glu Leu Val Val Ile Asp Val Asn Lys Glu Lys Ala Met Gly Asp Val
        35                  40                  45

Met Asp Leu Asn His Gly Lys Ala Phe Ala Pro Gln Pro Val Lys Thr
    50                  55                  60

Ser Tyr Gly Thr Tyr Glu Asp Cys Lys Asp Ala Asp Ile Val Cys Ile
65                  70                  75                  80

Cys Ala Gly Ala Asn Gln Lys Pro Gly Glu Thr Arg Leu Glu Leu Val
                85                  90                  95

Glu Lys Asn Leu Lys Ile Phe Lys Gly Ile Val Ser Glu Val Met Ala
            100                 105                 110

Ser Gly Phe Asp Gly Ile Phe Leu Val Ala Thr Asn Pro Val Asp Ile
        115                 120                 125

Leu Thr Tyr Ala Thr Trp Lys Phe Ser Gly Leu Pro Lys Glu Arg Val
    130                 135                 140

Ile Gly Ser Gly Thr Thr Leu Asp Ser Ala Arg Phe Arg Phe Met Leu
145                 150                 155                 160

Ser Glu Tyr Phe Gly Ala Ala Pro Gln Asn Val His Ala His Ile Ile
                165                 170                 175
```

Gly Glu His Gly Asp Thr Glu Leu Pro Val Trp Ser His Ala Asn Val
            180                 185                 190

Gly Gly Val Pro Val Ser Glu Leu Val Glu Lys Asn Asp Ala Tyr Lys
        195                 200                 205

Gln Glu Glu Leu Asp Gln Ile Val Asp Asp Val Lys Asn Ala Ala Tyr
    210                 215                 220

His Ile Ile Glu Lys Lys Gly Ala Thr Tyr Tyr Gly Val Ala Met Ser
225                 230                 235                 240

Leu Ala Arg Ile Thr Lys Ala Ile Leu His Asn Glu Asn Ser Ile Leu
                245                 250                 255

Thr Val Ser Thr Tyr Leu Asp Gly Gln Tyr Gly Ala Asp Asp Val Tyr
            260                 265                 270

Ile Gly Val Pro Ala Val Val Asn Arg Gly Gly Ile Ala Gly Ile Thr
        275                 280                 285

Glu Leu Asn Leu Asn Glu Lys Glu Lys Glu Gln Phe Leu His Ser Ala
    290                 295                 300

Gly Val Leu Lys Asn Ile Leu Lys Pro His Phe Ala Glu Gln Lys Val
305                 310                 315                 320

Asn

<210> SEQ ID NO 9
<211> LENGTH: 954
<212> TYPE: DNA
<213> ORGANISM: Geobacillus sterarothermophillus

<400> SEQUENCE: 9
atgaagaaca atggtggagc gcgtgttgtg gtaattggcg cgggttttgt gggtgccagc        60
tatgttttcg cgttaatgaa ccaaggtatt gcagacgaga ttgtcctgat tgacgcgaat       120
gaatccaaag cgattgggga cgccatggat ttcaaccacg gtaaagtgtt tgctccgaaa       180
ccggtcgata tctggcatgg cgattacgac gattgtcgcg atgccgatct ggtggtcatc       240
tgcgctggtg caaaccagaa acccggtgaa actcgtctgg atcttgttga caagaacatt       300
gccatctttc ggtctattgt cgaaagcgtg atggcaagtg ggtttcaggg actgtttctg       360
gttgccacca atccggtaga catcctgacg tatgctacct ggaaattcag cggcttaccg       420
catgaacgtg ttatcggcag tggtaccatt cttgatacgg cacgttttcg cttcctgttg       480
ggagagtact tctccgttgc ccctcagaat gtgcatgcct acatcattgg ggaacatggc       540
gataccgaat tgccagtgtg gtcgcaagcg tatattggtg taatgccgat tcgcaaactg       600
gtggaatcga aaggcgaaga agcccagaaa gacttggaac gcatctttgt caacgtacgc       660
gatgcagcgt atcagatcat cgagaaaaaa ggtgcgacct attacggcat cgcaatgggc       720
ttagctcgtg taactcgggc tattctgcac aacgagaacg cgattctcac agtgtcagcg       780
tatctcgatg ggctgtatgg cgaacgcgat gtgtacattg gcgttccagc cgtcatcaat       840
cgcaatggca ttcgtgaggt gattgaaatc gaactgaacg atgacgagaa gaatcgcttc       900
catcactctg cggctacact gaaaagcgtt ctcgcacgtg cgtttacgcg ctaa             954

<210> SEQ ID NO 10
<211> LENGTH: 317
<212> TYPE: PRT
<213> ORGANISM: Geobacillus sterarothermophillus

<400> SEQUENCE: 10

Met Lys Asn Asn Gly Gly Ala Arg Val Val Val Ile Gly Ala Gly Phe
1               5                   10                  15

```
Val Gly Ala Ser Tyr Val Phe Ala Leu Met Asn Gln Gly Ile Ala Asp
            20                  25                  30

Glu Ile Val Leu Ile Asp Ala Asn Glu Ser Lys Ala Ile Gly Asp Ala
            35                  40                  45

Met Asp Phe Asn His Gly Lys Val Phe Ala Pro Lys Pro Val Asp Ile
 50                  55                  60

Trp His Gly Asp Tyr Asp Asp Cys Arg Asp Ala Asp Leu Val Val Ile
 65                  70                  75                  80

Cys Ala Gly Ala Asn Gln Lys Pro Gly Glu Thr Arg Leu Asp Leu Val
                 85                  90                  95

Asp Lys Asn Ile Ala Ile Phe Arg Ser Ile Val Glu Ser Val Met Ala
                100                 105                 110

Ser Gly Phe Gln Gly Leu Phe Leu Val Ala Thr Asn Pro Val Asp Ile
            115                 120                 125

Leu Thr Tyr Ala Thr Trp Lys Phe Ser Gly Leu Pro His Glu Arg Val
130                 135                 140

Ile Gly Ser Gly Thr Ile Leu Asp Thr Ala Arg Phe Arg Phe Leu Leu
145                 150                 155                 160

Gly Glu Tyr Phe Ser Val Ala Pro Gln Asn Val His Ala Tyr Ile Ile
                165                 170                 175

Gly Glu His Gly Asp Thr Glu Leu Pro Val Trp Ser Gln Ala Tyr Ile
            180                 185                 190

Gly Val Met Pro Ile Arg Lys Leu Val Glu Ser Lys Gly Glu Glu Ala
            195                 200                 205

Gln Lys Asp Leu Glu Arg Ile Phe Val Asn Val Arg Asp Ala Ala Tyr
            210                 215                 220

Gln Ile Ile Glu Lys Lys Gly Ala Thr Tyr Tyr Gly Ile Ala Met Gly
225                 230                 235                 240

Leu Ala Arg Val Thr Arg Ala Ile Leu His Asn Glu Asn Ala Ile Leu
                245                 250                 255

Thr Val Ser Ala Tyr Leu Asp Gly Leu Tyr Gly Glu Arg Asp Val Tyr
            260                 265                 270

Ile Gly Val Pro Ala Val Ile Asn Arg Asn Gly Ile Arg Glu Val Ile
            275                 280                 285

Glu Ile Glu Leu Asn Asp Asp Glu Lys Asn Arg Phe His His Ser Ala
290                 295                 300

Ala Thr Leu Lys Ser Val Leu Ala Arg Ala Phe Thr Arg
305                 310                 315
```

<210> SEQ ID NO 11
<211> LENGTH: 999
<212> TYPE: DNA
<213> ORGANISM: Oryctolagus cuniculus

<400> SEQUENCE: 11

| | | |
|---|---|---|
| atggcggcgt tgaaagacca actgattcat aaccttttaa agaggaaca tgtgccgcag | 60 |
| aacaaaatta ccgttgtagg cgtaggtgca gttggtatgg cctgtgccat agcatcctg | 120 |
| atgaaagact ggcggatga acttgctctg gtcgatgtaa tggaggataa actgaaaggc | 180 |
| gaaatgatgg acttgcagca tgggtcgctg tttcttcgca cacccaagat cgtaagcggc | 240 |
| aaagattact ccgtgactgc aaattccaaa ttggtcatca ttaccgccgg agcacgccag | 300 |
| caagaaggtg aaagccgcct gaacctggtg caacggaacg tcaacatttt caaatttatc | 360 |
| attccgaacg tggtgaaata ctctccacac tgcaaactcc tcgttgttag taaccctgtt | 420 |

```
gacatcctga cgtatgttgc ctggaaaatt agcggcttcc cgaagaatcg cgtaattggc    480
tcaggatgca atctggattc ggcgcgtttt cgctatctga tgggcgaacg tttaggtgtt    540
catgcactgt catgccacgg gtggattctg ggtgaacatg gcgatagttc tgtgcctgtg    600
tggtctggca tgaatgtggc tggtgtgtca ctgaaaacgt tacacccaga acttggcact    660
gacgcggata agagcagtg gaaacaggta cacaaacagg tggtcgatag cgcgtatgag      720
gtcatcaaac tgaaaggtta caccacatgg gccattgggc tgagtgtcgc cgatctggct    780
gagagcatta tgaagaatct ccgtcgtgtt catccgatct ccacgatgct caaaggtctg    840
tatgggatca agaggacgt tttcttaagt gtgccgtgtg tcctgggtca gaatggcatt     900
tcggatgtgg tcaaggtgac cttaacctcg gaagaagaag cgcacctgaa gagagcgcg    960 gataccttgt ggggaatcca gaaagaactg caatttttaa    999
```

<210> SEQ ID NO 12
<211> LENGTH: 332
<212> TYPE: PRT
<213> ORGANISM: Oryctolagus cuniculus

<400> SEQUENCE: 12

```
Met Ala Ala Leu Lys Asp Gln Leu Ile His Asn Leu Leu Lys Glu
1               5                   10                  15

His Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Met Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Ala Leu Ser Cys His Gly Trp Ile Leu Gly Glu
            180                 185                 190

His Gly Asp Ser Ser Val Pro Val Trp Ser Gly Met Asn Val Ala Gly
        195                 200                 205

Val Ser Leu Lys Thr Leu His Pro Glu Leu Gly Thr Asp Ala Asp Lys
    210                 215                 220

Glu Gln Trp Lys Gln Val His Lys Gln Val Val Asp Ser Ala Tyr Glu
225                 230                 235                 240

Val Ile Lys Leu Lys Gly Tyr Thr Thr Trp Ala Ile Gly Leu Ser Val
                245                 250                 255

Ala Asp Leu Ala Glu Ser Ile Met Lys Asn Leu Arg Arg Val His Pro
            260                 265                 270
```

Ile Ser Thr Met Leu Lys Gly Leu Tyr Gly Ile Lys Glu Asp Val Phe
            275                 280                 285

Leu Ser Val Pro Cys Val Leu Gly Gln Asn Gly Ile Ser Asp Val Val
        290                 295                 300

Lys Val Thr Leu Thr Ser Glu Glu Glu Ala His Leu Lys Lys Ser Ala
305                 310                 315                 320

Asp Thr Leu Trp Gly Ile Gln Lys Glu Leu Gln Phe
            325                 330

<210> SEQ ID NO 13
<211> LENGTH: 1014
<212> TYPE: DNA
<213> ORGANISM: Oryctolagus cuniculus

<400> SEQUENCE: 13
atggcaacgc tgaaagagaa attgatcgca cctgtcgccg ataacgaagc ggctgttccg      60
aacaacaaaa ttaccgtagt aggcgtcggt caagtaggca tggcgtgtgc gatttccatt     120
ctcggcaaaa gtttagcgga cgaactggca cttgtcgatg tcttggaaga taaactgaaa     180
ggtgaaatga tggatttaca gcatggttcg ctgtttctcc agacacccaa aattgtggcg     240
gataaagatt acagtgtgac tgcgaacagc aagatcgtag ttgtcaccgc cggagtccgt     300
caacaggaag gtgaatcacg cctgaacttg gtgcaacgca atgtgaatgt gttcaaattc     360
atcatcccgc agattgttaa gtatagcccg aactgcatca tcattgtcgt cagcaaccct     420
gagtgtctgg ttgacatcct gacgtacgtt acctggaaac tctccggact gccgaaacac     480
cgcgtaattg gctcgggttg caatctggac agcgctcgtt ttcggtatct tatggccgag     540
aaattaggta ttcacccatc tagttgtcat ggatggattc tgggtgaaca tggcgatagc     600
tctgtggcag tatggtctgg cgttaacgtt gcgggtgtgt cgttgcaaga actgaatccg     660
gagatgggga ccgataatga tagcgaaaat tggaaagagg tgcacaaaat ggtggtggaa     720
agcgcctatg aagtgattaa gctgaaaggg tacaccaact gggcaattgg cttatcagtt     780
gcggatctta tcgagtccat gctgaagaat ctgtcacgca ttcatccggt ttccacaatg     840
gtgaaaggca tgtatgggat cgaaaacgaa gtgtttctgt ctttaccatg catcctgaat     900
gctcgtggcc tcacttcggt gattaatcag aagctgaaag atgacgaagt tgcccagctg     960
aagaaaagtg ccgatacgct gtgggacatt cagaaagacc tgaaagacct ttaa          1014

<210> SEQ ID NO 14
<211> LENGTH: 337
<212> TYPE: PRT
<213> ORGANISM: Oryctolagus cuniculus

<400> SEQUENCE: 14

Met Ala Thr Leu Lys Glu Lys Leu Ile Ala Pro Val Ala Asp Asn Glu
1               5                   10                  15

Ala Ala Val Pro Asn Asn Lys Ile Thr Val Val Gly Val Gly Gln Val
            20                  25                  30

Gly Met Ala Cys Ala Ile Ser Ile Leu Gly Lys Ser Leu Ala Asp Glu
        35                  40                  45

Leu Ala Leu Val Asp Val Leu Glu Asp Lys Leu Lys Gly Glu Met Met
    50                  55                  60

Asp Leu Gln His Gly Ser Leu Phe Leu Gln Thr Pro Lys Ile Val Ala
65                  70                  75                  80

Asp Lys Asp Tyr Ser Val Thr Ala Asn Ser Lys Ile Val Val Val Thr 85                  90                  95
Ala Gly Val Arg Gln Gln Glu Gly Glu Ser Arg Leu Asn Leu Val Gln
                    100                 105                 110

Arg Asn Val Asn Val Phe Lys Phe Ile Ile Pro Gln Ile Val Lys Tyr
            115                 120                 125

Ser Pro Asn Cys Ile Ile Ile Val Val Ser Asn Pro Glu Cys Leu Val
        130                 135                 140

Asp Ile Leu Thr Tyr Val Thr Trp Lys Leu Ser Gly Leu Pro Lys His
145                 150                 155                 160

Arg Val Ile Gly Ser Gly Cys Asn Leu Asp Ser Ala Arg Phe Arg Tyr
                165                 170                 175

Leu Met Ala Glu Lys Leu Gly Ile His Pro Ser Ser Cys His Gly Trp
            180                 185                 190

Ile Leu Gly Glu His Gly Asp Ser Ser Val Ala Val Trp Ser Gly Val
        195                 200                 205

Asn Val Ala Gly Val Ser Leu Gln Glu Leu Asn Pro Glu Met Gly Thr
    210                 215                 220

Asp Asn Asp Ser Glu Asn Trp Lys Glu Val His Lys Met Val Val Glu
225                 230                 235                 240

Ser Ala Tyr Glu Val Ile Lys Leu Lys Gly Tyr Thr Asn Trp Ala Ile
                245                 250                 255

Gly Leu Ser Val Ala Asp Leu Ile Glu Ser Met Leu Lys Asn Leu Ser
            260                 265                 270

Arg Ile His Pro Val Ser Thr Met Val Lys Gly Met Tyr Gly Ile Glu
        275                 280                 285

Asn Glu Val Phe Leu Ser Leu Pro Cys Ile Leu Asn Ala Arg Gly Leu
    290                 295                 300

Thr Ser Val Ile Asn Gln Lys Leu Lys Asp Asp Glu Val Ala Gln Leu
305                 310                 315                 320

Lys Lys Ser Ala Asp Thr Leu Trp Asp Ile Gln Lys Asp Leu Lys Asp
                325                 330                 335

Leu

<210> SEQ ID NO 15
<211> LENGTH: 27
<212> TYPE: DNA
<213> ORGANISM: Artificial Sequence
<220> FEATURE:
<223> OTHER INFORMATION: Primer for amplification

<400> SEQUENCE: 15
tataatcata tgaaagtcgc agtcctc                                    27

<210> SEQ ID NO 16
<211> LENGTH: 30
<212> TYPE: DNA
<213> ORGANISM: Artificial Sequence
<220> FEATURE:
<223> OTHER INFORMATION: Primer for amplification

<400> SEQUENCE: 16
tataatggat ccttacttat taacgaactc                                 30

<210> SEQ ID NO 17
<211> LENGTH: 33
<212> TYPE: DNA
<213> ORGANISM: Artificial Sequence
<220> FEATURE:

<223> OTHER INFORMATION: Primer for amplification

<400> SEQUENCE: 17
tataatcata tggctgataa acaacgtaaa aaa                                33

<210> SEQ ID NO 18
<211> LENGTH: 36
<212> TYPE: DNA
<213> ORGANISM: Artificial Sequence
<220> FEATURE:
<223> OTHER INFORMATION: Primer for amplification

<400> SEQUENCE: 18
tataatggat ccttagtttt taactgcaga agcaaa                             36

<210> SEQ ID NO 19
<211> LENGTH: 38
<212> TYPE: DNA
<213> ORGANISM: Artificial Sequence
<220> FEATURE:
<223> OTHER INFORMATION: Primer for amplification

<400> SEQUENCE: 19
tataatgcta gcatgatgaa caaacatgta aataaagt                           38

<210> SEQ ID NO 20
<211> LENGTH: 30
<212> TYPE: DNA
<213> ORGANISM: Artificial Sequence
<220> FEATURE:
<223> OTHER INFORMATION: Primer for amplification

<400> SEQUENCE: 20
tataatggat ccttagttga cttttttgttc                                   30

<210> SEQ ID NO 21
<211> LENGTH: 30
<212> TYPE: DNA
<213> ORGANISM: Artificial Sequence
<220> FEATURE:
<223> OTHER INFORMATION: Primer for amplification

<400> SEQUENCE: 21
tataatgcta gcatggcggc gttgaaagac                                    30

<210> SEQ ID NO 22
<211> LENGTH: 30
<212> TYPE: DNA
<213> ORGANISM: Artificial Sequence
<220> FEATURE:
<223> OTHER INFORMATION: Primer for amplification

<400> SEQUENCE: 22
attatagaat tcttaaaatt gcagttcttt                                    30

<210> SEQ ID NO 23
<211> LENGTH: 29
<212> TYPE: DNA
<213> ORGANISM: Artificial Sequence
<220> FEATURE:
<223> OTHER INFORMATION: Primer for amplification

<400> SEQUENCE: 23
tataatcata tgagaattac aattgccgg                                     29

```
<210> SEQ ID NO 24
<211> LENGTH: 41
<212> TYPE: DNA
<213> ORGANISM: Artificial Sequence
<220> FEATURE:
<223> OTHER INFORMATION: Primer for amplification

<400> SEQUENCE: 24
tataatggat ccttatttg cttttaataa ctcttctttg c                  41

<210> SEQ ID NO 25
<211> LENGTH: 29
<212> TYPE: DNA
<213> ORGANISM: Artificial Sequence
<220> FEATURE:
<223> OTHER INFORMATION: Primer for amplification

<400> SEQUENCE: 25
tataatcata tgaaactcgc cgtttatag                               29

<210> SEQ ID NO 26
<211> LENGTH: 30
<212> TYPE: DNA
<213> ORGANISM: Artificial Sequence
<220> FEATURE:
<223> OTHER INFORMATION: Primer for amplification

<400> SEQUENCE: 26
tataatggat ccttaaacca gttcgttcgg                              30

<210> SEQ ID NO 27
<211> LENGTH: 45
<212> TYPE: DNA
<213> ORGANISM: Artificial Sequence
<220> FEATURE:
<223> OTHER INFORMATION: Primer for amplification
<220> FEATURE:
<221> NAME/KEY: misc_feature
<222> LOCATION: (22)..(23)
<223> OTHER INFORMATION: n is a, c, g, or t

<400> SEQUENCE: 27
gtcttgactt ctggtgctcc annkaaacca ggtgaaacgc gtctt             45

<210> SEQ ID NO 28
<211> LENGTH: 45
<212> TYPE: DNA
<213> ORGANISM: Artificial Sequence
<220> FEATURE:
<223> OTHER INFORMATION: Primer for amplification
<220> FEATURE:
<221> NAME/KEY: misc_feature
<222> LOCATION: (23)..(24)
<223> OTHER INFORMATION: n is a, c, g, or t

<400> SEQUENCE: 28
aagacgcgtt tcacctggtt tmnntggagc accagaagtc aagac             45

<210> SEQ ID NO 29
<211> LENGTH: 978
<212> TYPE: DNA
<213> ORGANISM: Lactococcus lactis

<400> SEQUENCE: 29
atggctgata acaacgtaa aaaagttatc cttgtaggtg acggtgctgt aggttcatca    60
tacgcttttg ctcttgtaaa ccaagggatt gcacaagaat taggaattgt tgacctttt    120
```

```
aaagaaaaaa ctcaaggaga tgcagaagac ctttctcatg ccttggcatt tacttcacct    180
aaaaagattt actctgcaga ctactctgat gcaagcgacg ctgacctcgt agtcttgacg    240
tctggtgctc caaataaacc aggtgaaact cgtcttgacc ttgttgaaaa aaatcttcgt    300
atcactaaag atgttgtcac taaaattgtt gcttcaggtt tcaaaggaat cttccttgtt    360
gctgctaacc cagttgatat cttgacatac gctacttgga aattctcagg tttccctaaa    420
aaccgcgttg taggttcagg tacttcactt gatactgcac gtttccgtca agcattggca    480
gaaaaagttg atgttgacgc tcgttcaatc cacgcataca tcatgggtga acacggtgac    540
tcagaatttg ccgtttggtc acacgctaac gttgctggtg ttaaattgga acaatggttc    600
caagaaaatg actaccttaa cgaagctgaa atcgttgaat gtttgaatc tgtacgtgat    660 gctgcttact caatcatcgc taaaaaaggt gcaacattct atggtgtcgc tgtagctctt    720
gctcgtatta ctaaagcaat tcttgatgat gaacatgcag tacttccagt atcagtattc    780
caagatggac aatatggcgt aagcgactgc taccttggtc aaccagctgt agttggtgct    840
gaaggtgttg ttaacccaat ccacattcca ttgaatgatg ctgaaatgca aaaaatggaa    900
gcttctggtg ctcaattgaa agcaatcatt gacgaagctt ttgctaaaga gaatttgct    960 tctgcagtta aaaactaa                                                  978
```

<210> SEQ ID NO 30
<211> LENGTH: 325
<212> TYPE: PRT
<213> ORGANISM: Lactococcus lactis

<400> SEQUENCE: 30

```
Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
            20                  25                  30

Glu Leu Gly Ile Val Asp Leu Phe Lys Glu Lys Thr Gln Gly Asp Ala
        35                  40                  45

Glu Asp Leu Ser His Ala Leu Ala Phe Thr Ser Pro Lys Lys Ile Tyr
    50                  55                  60

Ser Ala Asp Tyr Ser Asp Ala Ser Asp Ala Asp Leu Val Val Leu Thr
65                  70                  75                  80

Ser Gly Ala Pro Asn Lys Pro Gly Glu Thr Arg Leu Asp Leu Val Glu
                85                  90                  95

Lys Asn Leu Arg Ile Thr Lys Asp Val Val Thr Lys Ile Val Ala Ser
            100                 105                 110

Gly Phe Lys Gly Ile Phe Leu Val Ala Ala Asn Pro Val Asp Ile Leu
        115                 120                 125

Thr Tyr Ala Thr Trp Lys Phe Ser Gly Phe Pro Lys Asn Arg Val Val
    130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
        195                 200                 205

Ala Glu Ile Val Glu Leu Phe Glu Ser Val Arg Asp Ala Ala Tyr Ser
    210                 215                 220
```

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
            245                 250                 255

Val Ser Val Phe Gln Asp Gly Gln Tyr Gly Val Ser Asp Cys Tyr Leu
        260                 265                 270

Gly Gln Pro Ala Val Gly Ala Glu Gly Val Asn Pro Ile His
    275                 280                 285

Ile Pro Leu Asn Asp Ala Glu Met Gln Lys Met Glu Ala Ser Gly Ala
    290                 295                 300

Gln Leu Lys Ala Ile Ile Asp Glu Ala Phe Ala Lys Glu Glu Phe Ala
305                 310                 315                 320

Ser Ala Val Lys Asn
            325

<210> SEQ ID NO 31
<211> LENGTH: 978
<212> TYPE: DNA
<213> ORGANISM: Lactococcus lactis

<400> SEQUENCE: 31
atggctgata acaacgtaa aaaagttatc cttgtaggtg acggtgctgt aggttcatca      60
tacgcttttg ctcttgtaaa ccaagggatt gcacaagaat taggaattgt tgacctttt     120 aaagaaaaaa ctcaaggaga tgcagaagac ctttctcatg ccttggcatt tacttcacct    180
aaaaagattt actctgcaga ctactctgat gcaagcgacg ctgacctcgt agtcttgacg    240
tctggtgctc caaataaacc aggtgaaact cgtcttgacc ttgttgaaaa aaatcttcgt    300
atcactaaag atgttgtcac taaaattgtt gcttcaggtt tcaaaggaat cttccttgtt    360
gctgctaacc cagttgatat cttgacatac gctacttgga aattctcagg tttccctaaa    420
aaccgcgttg taggttcagg tacttcactt gatactgcac gtttccgtca agcattggca    480
gaaaaagttg atgttgacgc tcgttcaatc cacgcataca tcatgggtga aacggtgac    540 tcagaatttg ccgtttggtc acacgctaac gttgctggtg ttaaattgga caatggttc    600 caagaaaatg actaccttaa cgaagctgaa atcgttgaat tgtttgaatc tgtacgtgat    660
gctgcttact cgatcgtcgc taaaaaaggt gcaacattct atggtgtcgc tgtagctctt    720
gctcgtatta ctaaagcaat tcttgatgat gaacatgcag tacttccagt atcagtattc    780
caagatggac aatatggcgt aagcgactgc taccttggtc aaccagctgt agttggtgct    840
gaaggtgttg ttaacccaat ccacattcca ttgaatgatg ctgaaatgca aaaaatggaa    900
gcttctggtg ctcaattgaa agcaatcatt gacgaagctt ttgctaaaga gaatttgct    960 tctgcagtta aaaactaa                                                 978

<210> SEQ ID NO 32
<211> LENGTH: 325
<212> TYPE: PRT
<213> ORGANISM: Lactococcus lactis

<400> SEQUENCE: 32

Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
            20                  25                  30

Glu Leu Gly Ile Val Asp Leu Phe Lys Glu Lys Thr Gln Gly Asp Ala

```
                35                  40                  45
Glu Asp Leu Ser His Ala Leu Ala Phe Thr Ser Pro Lys Lys Ile Tyr
 50                  55                  60
Ser Ala Asp Tyr Ser Asp Ala Ser Asp Ala Asp Leu Val Val Leu Thr
 65                  70                  75                  80
Ser Gly Ala Pro Asn Lys Pro Gly Glu Thr Arg Leu Asp Leu Val Glu
                 85                  90                  95
Lys Asn Leu Arg Ile Thr Lys Asp Val Val Thr Lys Ile Val Ala Ser
            100                 105                 110
Gly Phe Lys Gly Ile Phe Leu Val Ala Ala Asn Pro Val Asp Ile Leu
        115                 120                 125
Thr Tyr Ala Thr Trp Lys Phe Ser Gly Phe Pro Lys Asn Arg Val Val
    130                 135                 140
Gly Ser Gly Thr Ser Leu Asp Thr Ala Arg Phe Arg Gln Ala Leu Ala
145                 150                 155                 160
Glu Lys Val Asp Val Asp Ala Arg Ser Ile His Ala Tyr Ile Met Gly
                165                 170                 175
Glu His Gly Asp Ser Glu Phe Ala Val Trp Ser His Ala Asn Val Ala
            180                 185                 190
Gly Val Lys Leu Glu Gln Trp Phe Gln Glu Asn Asp Tyr Leu Asn Glu
        195                 200                 205
Ala Glu Ile Val Glu Leu Phe Glu Ser Val Arg Asp Ala Ala Tyr Ser
    210                 215                 220
Ile Val Ala Lys Lys Gly Ala Thr Phe Tyr Gly Val Ala Val Ala Leu
225                 230                 235                 240
Ala Arg Ile Thr Lys Ala Ile Leu Asp Asp Glu His Ala Val Leu Pro
                245                 250                 255
Val Ser Val Phe Gln Asp Gly Gln Tyr Gly Val Ser Asp Cys Tyr Leu
            260                 265                 270
Gly Gln Pro Ala Val Val Gly Ala Glu Gly Val Val Asn Pro Ile His
        275                 280                 285
Ile Pro Leu Asn Asp Ala Glu Met Gln Lys Met Glu Ala Ser Gly Ala
    290                 295                 300
Gln Leu Lys Ala Ile Ile Asp Glu Ala Phe Ala Lys Glu Glu Phe Ala
305                 310                 315                 320
Ser Ala Val Lys Asn
                325

<210> SEQ ID NO 33
<211> LENGTH: 43
<212> TYPE: DNA
<213> ORGANISM: Artificial Sequence
<220> FEATURE:
<223> OTHER INFORMATION: Primer for amplification
<220> FEATURE:
<221> NAME/KEY: misc_feature
<222> LOCATION: (21)..(22)
<223> OTHER INFORMATION: n is a, c, g, or t

<400> SEQUENCE: 33
ttatctctgc aggcgtagcg nnkaaacccg ggatggatcg ttc          43

<210> SEQ ID NO 34
<211> LENGTH: 43
<212> TYPE: DNA
<213> ORGANISM: Artificial Sequence
<220> FEATURE:
<223> OTHER INFORMATION: Primer for amplification
```

<220> FEATURE:
<221> NAME/KEY: misc_feature
<222> LOCATION: (22)..(23)
<223> OTHER INFORMATION: n is a, c, g, or t

<400> SEQUENCE: 34
gaacgatcca tcccgggttt mnncgctacg cctgcagaga taa                43

<210> SEQ ID NO 35
<211> LENGTH: 50
<212> TYPE: DNA
<213> ORGANISM: Artificial Sequence
<220> FEATURE:
<223> OTHER INFORMATION: Primer for amplification

<400> SEQUENCE: 35
ttatctctgc aggcgtagcg gctaaaccgg gtgaggatcg ttccgacctg          50

<210> SEQ ID NO 36
<211> LENGTH: 50
<212> TYPE: DNA
<213> ORGANISM: Artificial Sequence
<220> FEATURE:
<223> OTHER INFORMATION: Primer for amplification

<400> SEQUENCE: 36
caggtcggaa cgatcctcac ccggtttagc cgctacgcct gcagagataa          50

<210> SEQ ID NO 37
<211> LENGTH: 50
<212> TYPE: DNA
<213> ORGANISM: Artificial Sequence
<220> FEATURE:
<223> OTHER INFORMATION: Primer for amplification

<400> SEQUENCE: 37
ttatctctgc aggcgtagcg gctaaaccgg gtcaggatcg ttccgacctg          50

<210> SEQ ID NO 38
<211> LENGTH: 50
<212> TYPE: DNA
<213> ORGANISM: Artificial Sequence
<220> FEATURE:
<223> OTHER INFORMATION: Primer for amplification

<400> SEQUENCE: 38
caggtcggaa cgatcctgac ccggtttagc cgctacgcct gcagagataa          50

<210> SEQ ID NO 39
<211> LENGTH: 46
<212> TYPE: DNA
<213> ORGANISM: Artificial Sequence
<220> FEATURE:
<223> OTHER INFORMATION: Primer for amplification

<400> SEQUENCE: 39
gtcgcagtcc tcggcgccgc tggcggtgtc ggccaggcgc ttgcac             46

<210> SEQ ID NO 40
<211> LENGTH: 46
<212> TYPE: DNA
<213> ORGANISM: Artificial Sequence
<220> FEATURE:
<223> OTHER INFORMATION: Primer for amplification

<400> SEQUENCE: 40
gtgcaagcgc ctggccgaca ccgccagcgg cgccgaggac tgcgac        46

<210> SEQ ID NO 41
<211> LENGTH: 45
<212> TYPE: DNA
<213> ORGANISM: Artificial Sequence
<220> FEATURE:
<223> OTHER INFORMATION: Primer for amplification

<400> SEQUENCE: 41
ccggttattg gcggccactc tgatgttacc attctgccgc tgctg        45

<210> SEQ ID NO 42
<211> LENGTH: 45
<212> TYPE: DNA
<213> ORGANISM: Artificial Sequence
<220> FEATURE:
<223> OTHER INFORMATION: Primer for amplification

<400> SEQUENCE: 42
cagcagcggc agaatggtaa catcagagtg gccgccaata accgg        45

<210> SEQ ID NO 43
<211> LENGTH: 39
<212> TYPE: DNA
<213> ORGANISM: Artificial Sequence
<220> FEATURE:
<223> OTHER INFORMATION: Primer for amplification

<400> SEQUENCE: 43
ggcgtagcgg ctaaaccggg tatgtctcgt tccgacctg        39

<210> SEQ ID NO 44
<211> LENGTH: 39
<212> TYPE: DNA
<213> ORGANISM: Artificial Sequence
<220> FEATURE:
<223> OTHER INFORMATION: Primer for amplification

<400> SEQUENCE: 44
caggtcggaa cgagacatac ccggtttagc cgctacgcc        39

<210> SEQ ID NO 45
<211> LENGTH: 37
<212> TYPE: DNA
<213> ORGANISM: Artificial Sequence
<220> FEATURE:
<223> OTHER INFORMATION: Primer for amplification

<400> SEQUENCE: 45
acggatccag aacgccggct atgaagtggt tgaagcg        37

<210> SEQ ID NO 46
<211> LENGTH: 37
<212> TYPE: DNA
<213> ORGANISM: Artificial Sequence
<220> FEATURE:
<223> OTHER INFORMATION: Primer for amplification

<400> SEQUENCE: 46
cgcttcaacc acttcatagc cggcgttctg gatccgt        37

<210> SEQ ID NO 47
<211> LENGTH: 37
<212> TYPE: DNA
<213> ORGANISM: Artificial Sequence
<220> FEATURE:
<223> OTHER INFORMATION: Primer for amplification

<400> SEQUENCE: 47
tataatgcta gcatgaccac gaagaaagct gattaca                37

<210> SEQ ID NO 48
<211> LENGTH: 35
<212> TYPE: DNA
<213> ORGANISM: Artificial Sequence
<220> FEATURE:
<223> OTHER INFORMATION: Primer for amplification

<400> SEQUENCE: 48
tataatggat ccttattgat taacttgatc taacc                35

<210> SEQ ID NO 49
<211> LENGTH: 31
<212> TYPE: DNA
<213> ORGANISM: Artificial Sequence
<220> FEATURE:
<223> OTHER INFORMATION: Primer for amplification

<400> SEQUENCE: 49
tataatgcta gcgtgtttca aaaagttgac g                31

<210> SEQ ID NO 50
<211> LENGTH: 31
<212> TYPE: DNA
<213> ORGANISM: Artificial Sequence
<220> FEATURE:
<223> OTHER INFORMATION: Primer for amplification

<400> SEQUENCE: 50
tataatggat ccttacatca ccgcagcaaa c                31

<210> SEQ ID NO 51
<211> LENGTH: 32
<212> TYPE: DNA
<213> ORGANISM: Artificial Sequence
<220> FEATURE:
<223> OTHER INFORMATION: Primer for amplification

<400> SEQUENCE: 51
tataatgcta gcatgtttga gaacattacc gc                32

<210> SEQ ID NO 52
<211> LENGTH: 32
<212> TYPE: DNA
<213> ORGANISM: Artificial Sequence
<220> FEATURE:
<223> OTHER INFORMATION: Primer for amplification

<400> SEQUENCE: 52
tataatggat ccttacagca ctgccacaat cg                32

<210> SEQ ID NO 53
<211> LENGTH: 41
<212> TYPE: DNA
<213> ORGANISM: Artificial Sequence
<220> FEATURE:
<223> OTHER INFORMATION: Primer for amplification

<400> SEQUENCE: 53
tataatgcta gcatggattt attaaaaaaa tttaaccctaa a                41

<210> SEQ ID NO 54
<211> LENGTH: 37
<212> TYPE: DNA
<213> ORGANISM: Artificial Sequence
<220> FEATURE:
<223> OTHER INFORMATION: Primer for amplification

<400> SEQUENCE: 54
tataatggat cctcagccac gttttttagt cacataa                37

<210> SEQ ID NO 55
<211> LENGTH: 32
<212> TYPE: DNA
<213> ORGANISM: Artificial Sequence
<220> FEATURE:
<223> OTHER INFORMATION: Primer for amplification

<400> SEQUENCE: 55
tataatgcta gcatggcaat taatttagac tg                     32

<210> SEQ ID NO 56
<211> LENGTH: 32
<212> TYPE: DNA
<213> ORGANISM: Artificial Sequence
<220> FEATURE:
<223> OTHER INFORMATION: Primer for amplification

<400> SEQUENCE: 56
tataatggat ccttaatcaa ctttaactat cc                     32

<210> SEQ ID NO 57
<211> LENGTH: 38
<212> TYPE: DNA
<213> ORGANISM: Artificial Sequence
<220> FEATURE:
<223> OTHER INFORMATION: Primer for amplification

<400> SEQUENCE: 57
tataatcata tgatcatgac tttacctgaa tcaaaaga               38

<210> SEQ ID NO 58
<211> LENGTH: 37
<212> TYPE: DNA
<213> ORGANISM: Artificial Sequence
<220> FEATURE:
<223> OTHER INFORMATION: Primer for amplification

<400> SEQUENCE: 58
tataatggat ccctatttgg aaataccaaa ttcttcg                37

<210> SEQ ID NO 59
<211> LENGTH: 930
<212> TYPE: DNA
<213> ORGANISM: Escherichia coli

<400> SEQUENCE: 59
atgaccacga agaaagctga ttacatttgg ttcaatgggg agatggttcg ctgggaagac      60
gcgaaggtgc atgtgatgtc gcacgcgctg cactatggca cttcggtttt tgaaggcatc     120
cgttgctacg actcgcacaa aggaccggtt gtattccgcc atcgtgagca tatgcagcgt     180
ctgcatgact ccgccaaaat ctatcgcttc ccggtttcgc agagcattga tgagctgatg     240
gaagcttgtc gtgacgtgat ccgcaaaaac aatctcacca cgcgcctata tccgtccgctg    300 atcttcgtcg gtgatgttgg catgggagta aacccgccag cgggatactc aaccgacgtg    360

```
attatcgctg ctttcccgtg gggagcgtat ctgggcgcag aagcgctgga gcaggggatc    420
gatgcgatgg tttcctcctg gaaccgcgca gcaccaaaca ccatcccgac ggcggcaaaa    480
gccggtggta actacctctc ttccctgctg gtgggtagcg aagcgcgccg ccacggttat    540
caggaaggta tcgcgctgga tgtgaacggt tatatctctg aaggcgcagg cgaaaacctg    600
tttgaagtga agatggtgt gctgttcacc ccaccgttca cctcctccgc gctgccgggt    660
attacccgtg atgccatcat caaactggcg aaagagctgg gaattgaagt acgtgagcag    720
gtgctgtcgc gcgaatccct gtacctggcg gatgaagtgt ttatgtccgg tacggcggca    780
gaaatcacgc cagtgcgcag cgtagacggt attcaggttg gcgaaggccg ttgtggcccg    840
gttaccaaac gcattcagca agccttcttc ggcctcttca ctggcgaaac cgaagataaa    900
tggggctggt tagatcaagt taatcaataa                                     930
```

<210> SEQ ID NO 60
<211> LENGTH: 309
<212> TYPE: PRT
<213> ORGANISM: Escherichia coli

<400> SEQUENCE: 60

```
Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
        35                  40                  45

Pro Val Val Phe Arg His Arg Glu His Met Gln Arg Leu His Asp Ser
    50                  55                  60

Ala Lys Ile Tyr Arg Phe Pro Val Ser Gln Ser Ile Asp Glu Leu Met
65                  70                  75                  80

Glu Ala Cys Arg Asp Val Ile Arg Lys Asn Asn Leu Thr Ser Ala Tyr
                85                  90                  95

Ile Arg Pro Leu Ile Phe Val Gly Asp Val Gly Met Gly Val Asn Pro
            100                 105                 110

Pro Ala Gly Tyr Ser Thr Asp Val Ile Ala Ala Phe Pro Trp Gly
        115                 120                 125

Ala Tyr Leu Gly Ala Glu Ala Leu Glu Gln Gly Ile Asp Ala Met Val
    130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
            180                 185                 190

Ser Glu Gly Ala Gly Glu Asn Leu Phe Glu Val Lys Asp Gly Val Leu
        195                 200                 205

Phe Thr Pro Pro Phe Thr Ser Ser Ala Leu Pro Gly Ile Thr Arg Asp
    210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270
```

Val Gly Glu Gly Arg Cys Gly Pro Val Thr Lys Arg Ile Gln Gln Ala
    275                 280                 285

Phe Phe Gly Leu Phe Thr Gly Glu Thr Glu Asp Lys Trp Gly Trp Leu
    290                 295                 300

Asp Gln Val Asn Gln
305

<210> SEQ ID NO 61
<211> LENGTH: 1194
<212> TYPE: DNA
<213> ORGANISM: Escherichia coli

<400> SEQUENCE: 61
gtgtttcaaa aagttgacgc ctacgctggc gacccgattc ttacgcttat ggagcgtttt      60
aaagaagacc ctcgcagcga caaagtgaat ttaagtatcg gtctgtacta caacgaagac     120
ggaattattc cacaactgca agccgtggcg gaggcggaag cgcgcctgaa tgcgcagcct     180
catggcgctt cgctttattt accgatggaa gggcttaact gctatcgcca tgccattgcg     240
ccgctgctgt ttggtgcgga ccatccggta ctgaaacaac agcgcgtagc aaccattcaa     300
acccttggcg gctccgggc attgaaagtg gcgcgcgatt cctgaaacg ctacttcccg      360 gaatcaggcg tctgggtcag cgatcctacc tgggaaaacc acgtagcaat attcgccggg     420
gctggattcg aagtgagtac ttaccctg tatgacgaag cgactaacgg cgtgcgcttt       480
aatgacctgt tggcgacgct gaaaacatta cctgcccgca gtattgtgtt gctgcatcca     540
tgttgccaca acccaacggg tgccgatctc actaatgatc agtgggatgc ggtgattgaa     600
attctcaaag cccgcgagct tattccattc ctcgatattg cctatcaagg atttggtgcc     660
ggtatggaag aggatgccta cgctattcgc gccattgcca cgctggatt accccgctctg     720 gtgagcaatt cgttctcgaa attttctcc ctttacggcg agcgcgtcgg cggactttct     780
gttatgtgtg aagatgccga agccgctggc cgcgtactgg ggcaattgaa agcaacagtt     840
cgccgcaact actccagccc gccgaatttt ggtgcgcagg tggtggctgc agtgctgaat     900
gacgaggcat tgaaagccag ctggctggcg gaagtagaag agatgcgtac tcgcattctg     960
gcaatgcgtc aggaattggt gaaggtatta agcacagaga tgccagaacg caatttcgat    1020
tatctgctta atcagcgcgg catgttcagt tataccggtt taagtgccgc tcaggttgac    1080
cgactacgtg aagaatttgg tgtctatctc atcgccagcg gtcgcatgtg tgtcgccggg    1140
ttaaatacgg caaatgtaca acgtgtggca aaggcgtttg ctgcggtgat gtaa          1194

<210> SEQ ID NO 62
<211> LENGTH: 397
<212> TYPE: PRT
<213> ORGANISM: Escherichia coli

<400> SEQUENCE: 62

Val Phe Gln Lys Val Asp Ala Tyr Ala Gly Asp Pro Ile Leu Thr Leu
1               5                   10                  15

Met Glu Arg Phe Lys Glu Asp Pro Arg Ser Asp Lys Val Asn Leu Ser
            20                  25                  30

Ile Gly Leu Tyr Tyr Asn Glu Asp Gly Ile Ile Pro Gln Leu Gln Ala
        35                  40                  45

Val Ala Glu Ala Glu Ala Arg Leu Asn Ala Gln Pro His Gly Ala Ser
    50                  55                  60

Leu Tyr Leu Pro Met Glu Gly Leu Asn Cys Tyr Arg His Ala Ile Ala

```
            65                  70                  75                  80
Pro Leu Leu Phe Gly Ala Asp His Pro Val Leu Lys Gln Gln Arg Val
                    85                  90                  95
Ala Thr Ile Gln Thr Leu Gly Gly Ser Gly Ala Leu Lys Val Gly Ala
                100                 105                 110
Asp Phe Leu Lys Arg Tyr Phe Pro Glu Ser Gly Val Trp Val Ser Asp
                115                 120                 125
Pro Thr Trp Glu Asn His Val Ala Ile Phe Ala Gly Ala Gly Phe Glu
                130                 135                 140
Val Ser Thr Tyr Pro Trp Tyr Asp Glu Ala Thr Asn Gly Val Arg Phe
145                 150                 155                 160
Asn Asp Leu Leu Ala Thr Leu Lys Thr Leu Pro Ala Arg Ser Ile Val
                165                 170                 175
Leu Leu His Pro Cys Cys His Asn Pro Thr Gly Ala Asp Leu Thr Asn
                180                 185                 190
Asp Gln Trp Asp Ala Val Ile Glu Ile Leu Lys Ala Arg Glu Leu Ile
                195                 200                 205
Pro Phe Leu Asp Ile Ala Tyr Gln Gly Phe Gly Ala Gly Met Glu Glu
                210                 215                 220
Asp Ala Tyr Ala Ile Arg Ala Ile Ala Ser Ala Gly Leu Pro Ala Leu
225                 230                 235                 240
Val Ser Asn Ser Phe Ser Lys Ile Phe Ser Leu Tyr Gly Glu Arg Val
                245                 250                 255
Gly Gly Leu Ser Val Met Cys Glu Asp Ala Glu Ala Ala Gly Arg Val
                260                 265                 270
Leu Gly Gln Leu Lys Ala Thr Val Arg Arg Asn Tyr Ser Ser Pro Pro
                275                 280                 285
Asn Phe Gly Ala Gln Val Val Ala Ala Val Leu Asn Asp Glu Ala Leu
                290                 295                 300
Lys Ala Ser Trp Leu Ala Glu Val Glu Glu Met Arg Thr Arg Ile Leu
305                 310                 315                 320
Ala Met Arg Gln Glu Leu Val Lys Val Leu Ser Thr Glu Met Pro Glu
                325                 330                 335
Arg Asn Phe Asp Tyr Leu Leu Asn Gln Arg Gly Met Phe Ser Tyr Thr
                340                 345                 350
Gly Leu Ser Ala Ala Gln Val Asp Arg Leu Arg Glu Glu Phe Gly Val
                355                 360                 365
Tyr Leu Ile Ala Ser Gly Arg Met Cys Val Ala Gly Leu Asn Thr Ala
                370                 375                 380
Asn Val Gln Arg Val Ala Lys Ala Phe Ala Ala Val Met
385                 390                 395

<210> SEQ ID NO 63
<211> LENGTH: 1191
<212> TYPE: DNA
<213> ORGANISM: Escherichia coli

<400> SEQUENCE: 63
atgtttgaga acattaccgc cgctcctgcc gacccgattc tgggcctggc cgatctgttt      60
cgtgccgatg aacgtcccgg caaaattaac ctcgggattg gtgtctataa agatgagacg     120
ggcaaaaccc cggtactgac cagcgtgaaa aaggctgaac agtatctgct cgaaaatgaa     180
accaccaaaa attcctcgg cattgacggc atccctgaat tggtcgctg cactcaggaa      240 ctgctgtttg gtaaaggtag cgccctgatc aatgacaaac gtgctcgcac ggcacagact     300
```

```
ccgggggca ctggcgcact acgcgtggct gccgatttcc tggcaaaaaa taccagcgtt    360
aagcgtgtgt gggtgagcaa cccaagctgg ccgaaccata agagcgtctt taactctgca    420
ggtctggaag ttcgtgaata cgcttattat gatgcggaaa atcacactct tgacttcgat    480
gcactgatta acagcctgaa tgaagctcag gctggcgacg tagtgctgtt ccatggctgc    540
tgccataacc caaccggtat cgaccctacg ctggaacaat ggcaaacact ggcacaactc    600
tccgttgaga aaggctggtt accgctgttt gacttcgctt accagggttt tgcccgtggt    660
ctggaagaag atgctgaagg actgcgcgct ttcgcggcta tgcataaaga gctgattgtt    720
gccagttcct actctaaaaa ctttggcctg tacaacgagc gtgttggcgc ttgtactctg    780
gttgctgccg acagtgaaac cgttgatcgc gcattcagcc aaatgaaagc ggcgattcgc    840
gctaactact ctaacccacc agcacacggc gcttctgttg ttgccaccat cctgagcaac    900
gatgcgttac gtgcgatttg gaacaagag ctgactgata tgcgccagcg tattcagcgt    960
atgcgtcagt tgttcgtcaa tacgctgcag gaaaaaggcg caaaccgcga cttcagcttt    1020
atcatcaaac agaacggcat gttctccttc agtggcctga caaagaaca agtgctgcgt    1080 ctgcgcgaag agtttggcgt atatgcggtt gcttctggtc gcgtaaatgt ggccgggatg    1140
acaccagata acatggctcc gctgtgcgaa gcgattgtgg cagtgctgta a             1191
```

<210> SEQ ID NO 64
<211> LENGTH: 396
<212> TYPE: PRT
<213> ORGANISM: Escherichia coli

<400> SEQUENCE: 64

```
Met Phe Glu Asn Ile Thr Ala Ala Pro Ala Asp Pro Ile Leu Gly Leu
  1               5                  10                  15

Ala Asp Leu Phe Arg Ala Asp Glu Arg Pro Gly Lys Ile Asn Leu Gly
                 20                  25                  30

Ile Gly Val Tyr Lys Asp Glu Thr Gly Lys Thr Pro Val Leu Thr Ser
             35                  40                  45

Val Lys Lys Ala Glu Gln Tyr Leu Leu Glu Asn Glu Thr Thr Lys Asn
         50                  55                  60

Tyr Leu Gly Ile Asp Gly Ile Pro Glu Phe Gly Arg Cys Thr Gln Glu
 65                  70                  75                  80

Leu Leu Phe Gly Lys Gly Ser Ala Leu Ile Asn Asp Lys Arg Ala Arg
                 85                  90                  95

Thr Ala Gln Thr Pro Gly Gly Thr Gly Ala Leu Arg Val Ala Ala Asp
            100                 105                 110

Phe Leu Ala Lys Asn Thr Ser Val Lys Arg Val Trp Val Ser Asn Pro
        115                 120                 125

Ser Trp Pro Asn His Lys Ser Val Phe Asn Ser Ala Gly Leu Glu Val
    130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
            180                 185                 190

Gln Trp Gln Thr Leu Ala Gln Leu Ser Val Glu Lys Gly Trp Leu Pro
        195                 200                 205

Leu Phe Asp Phe Ala Tyr Gln Gly Phe Ala Arg Gly Leu Glu Glu Asp
```

```
                    210                 215                 220
Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                    245                 250                 255

Ala Cys Thr Leu Val Ala Ala Asp Ser Glu Thr Val Asp Arg Ala Phe
                260                 265                 270

Ser Gln Met Lys Ala Ala Ile Arg Ala Asn Tyr Ser Asn Pro Pro Ala
            275                 280                 285

His Gly Ala Ser Val Val Ala Thr Ile Leu Ser Asn Asp Ala Leu Arg
        290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Lys Gly Ala Asn Arg
                    325                 330                 335

Asp Phe Ser Phe Ile Ile Lys Gln Asn Gly Met Phe Ser Phe Ser Gly
                340                 345                 350

Leu Thr Lys Glu Gln Val Leu Arg Leu Arg Glu Glu Phe Gly Val Tyr
            355                 360                 365

Ala Val Ala Ser Gly Arg Val Asn Val Ala Gly Met Thr Pro Asp Asn
        370                 375                 380

Met Ala Pro Leu Cys Glu Ala Ile Val Ala Val Leu
385                 390                 395

<210> SEQ ID NO 65
<211> LENGTH: 1176
<212> TYPE: DNA
<213> ORGANISM: Lactococcus lactis

<400> SEQUENCE: 65
atggatttat taaaaaaatt taaccctaat ttagataaaa ttgaaatttc attgattcgt      60
cagtttgacc aacaggtttc atctattcct gatgttatta agttgacttt gggagaacct     120
gatttttata cgcctgagca tgttaaacaa gcagggattg tggcgattga aaataatcaa     180
agtcattata ctggaatggc tggtttacta gaactacgtc aggcagctag tgaatttatg     240
aataaaaaat atggtttatc ttatgcagca gaagatgaaa ttttagttac tgttggagta     300
acggaagcca tttctagtgt tttgttatca attttggttg ctggtgatga agttttgatt     360
cccgcgcctg catatcctgg ttatgagcca ttaattacgc ttgctggcgg ttctttggtt     420
gaaattgata caagagctaa tgattttgtt cttacgcctg agatgcttga acaagcgatt     480
gtcgagcgtg agggaaaagt taaggccgtt attttgaatt atccagcaaa tcctacaggg     540
gtaacttata tcgggggca aattaaggct ttagctgaag ttttgaaaaa gcatgaagta     600
tttgtgattg ctgatgaagt ttattctgaa ctaaattata ctgaccaacc gcatgtgtca     660
attgctgaat atgcacctga gcaaacaatc gttcttaatg gttatcaaaa tcgcatgcg      720 atgactggtt ggcggattgg attaatcttt gcagcgcgtg aattagtggc acagattatt     780
aagactcacc aatatttggt gacttcggct tcaactcagt cacagtttgc agcgattgaa     840
gctttgaaaa atggtgctta tgatgctctt ccgatgaaaa agaatatct taaacgtcgt     900 gattatatta ttgaaaagat gtcagacctt ggtttcaaaa ttattgaacc agatggagct     960
ttctacattt ttgcaaaaat tccagctgat ttagaacaag attcattcaa atttgctgtg    1020
gattttgcaa aagaaaatgc agttgccatt attcctggta tcgcttttgg tcagtacggt    1080
```

```
gaaggatttg tccgcttatc ttatgcggct tcaatggata tgattgagca agcaatggca    1140
agattgacgg attatgtgac taaaaaacgt ggctga                              1176
```

<210> SEQ ID NO 66
<211> LENGTH: 391
<212> TYPE: PRT
<213> ORGANISM: Lactococcus lactis

<400> SEQUENCE: 66

```
Met Asp Leu Leu Lys Lys Phe Asn Pro Asn Leu Asp Lys Ile Glu Ile
1               5                   10                  15

Ser Leu Ile Arg Gln Phe Asp Gln Gln Val Ser Ser Ile Pro Asp Val
            20                  25                  30

Ile Lys Leu Thr Leu Gly Glu Pro Asp Phe Tyr Thr Pro Glu His Val
        35                  40                  45

Lys Gln Ala Gly Ile Val Ala Ile Glu Asn Asn Gln Ser His Tyr Thr
    50                  55                  60

Gly Met Ala Gly Leu Leu Glu Leu Arg Gln Ala Ala Ser Glu Phe Met
65                  70                  75                  80

Asn Lys Lys Tyr Gly Leu Ser Tyr Ala Ala Glu Asp Glu Ile Leu Val
                85                  90                  95

Thr Val Gly Val Thr Glu Ala Ile Ser Ser Val Leu Leu Ser Ile Leu
            100                 105                 110

Val Ala Gly Asp Glu Val Leu Ile Pro Ala Pro Ala Tyr Pro Gly Tyr
        115                 120                 125

Glu Pro Leu Ile Thr Leu Ala Gly Gly Ser Leu Val Glu Ile Asp Thr
    130                 135                 140

Arg Ala Asn Asp Phe Val Leu Thr Pro Glu Met Leu Glu Gln Ala Ile
145                 150                 155                 160

Val Glu Arg Glu Gly Lys Val Lys Ala Val Ile Leu Asn Tyr Pro Ala
                165                 170                 175

Asn Pro Thr Gly Val Thr Tyr Asn Arg Gly Gln Ile Lys Ala Leu Ala
            180                 185                 190

Glu Val Leu Lys Lys His Glu Val Phe Val Ile Ala Asp Glu Val Tyr
        195                 200                 205

Ser Glu Leu Asn Tyr Thr Asp Gln Pro His Val Ser Ile Ala Glu Tyr
    210                 215                 220

Ala Pro Glu Gln Thr Ile Val Leu Asn Gly Leu Ser Lys Ser His Ala
225                 230                 235                 240

Met Thr Gly Trp Arg Ile Gly Leu Ile Phe Ala Ala Arg Glu Leu Val
                245                 250                 255

Ala Gln Ile Ile Lys Thr His Gln Tyr Leu Val Thr Ser Ala Ser Thr
            260                 265                 270

Gln Ser Gln Phe Ala Ala Ile Glu Ala Leu Lys Asn Gly Ala Tyr Asp
        275                 280                 285

Ala Leu Pro Met Lys Lys Glu Tyr Leu Lys Arg Arg Asp Tyr Ile Ile
    290                 295                 300

Glu Lys Met Ser Asp Leu Gly Phe Lys Ile Ile Glu Pro Asp Gly Ala
305                 310                 315                 320

Phe Tyr Ile Phe Ala Lys Ile Pro Ala Asp Leu Glu Gln Asp Ser Phe
                325                 330                 335

Lys Phe Ala Val Asp Phe Ala Lys Glu Asn Ala Val Ala Ile Ile Pro
            340                 345                 350

Gly Ile Ala Phe Gly Gln Tyr Gly Glu Gly Phe Val Arg Leu Ser Tyr
```

```
              355                 360                 365
Ala Ala Ser Met Asp Met Ile Glu Gln Ala Met Ala Arg Leu Thr Asp
    370                 375                 380

Tyr Val Thr Lys Lys Arg Gly
385                 390
```

<210> SEQ ID NO 67
<211> LENGTH: 1023
<212> TYPE: DNA
<213> ORGANISM: Lactococcus lactis

<400> SEQUENCE: 67

```
atggcaatta atttagactg ggaaaattta ggattcagct atcggaactt accttttcgt      60
tatatcgctc gttttaaaga tggaaaatgg agtgctggag aactaacagg agataatcaa     120
cttcatatta gtgaatcatc acctgctttg cattatggtc aacaaggttt tgaaggatta     180
aaagcctatc gaacaaagga tggttcaatc caacttttcc gtcctgacca aaatgctgct     240
cgtttgcaaa atacggcgcg tcgactttgc atggcagaag ttccaactga atgtttatt     300
gatgcagtta acaagtggt gaaagcaaac gaagattttg tgcctcctta cggaacgggt     360
gcaacgctct atctccgtcc acttttgatt ggggttggtg acgttattgg ggtgaaacct     420
gctgatgaat atattttcac cgttttgct atgccggttg gttcttattt taaaggcgga     480
ttggctcctt caaatttgt aatttcaaga gattatgata gggcagctcc acttggtaca     540
ggtggtgcca agttggagg aaattatgca gcttctttac aagcagaagt tggtgccaaa     600
gcttcaggct atgcagatgc aatttatctt gacccaagca cacatactaa aattgaagaa     660
gtcggggcag caaatttctt tggaattaca gccgataatg aatttatcac accattgagt     720
ccatcaatct taccttcaat tactaaatat tctcttcttt atttagctga acatcgtttg     780
ggactcaaag cgattgaggg tgaagtttat gccaaagatt taggtaaatt tgttgaagca     840
ggagcttgtg gcacagcggc aattatctct ccaattggtc gtattgacga tggagaagat     900
tcttacattt tccattcaga aacagaagta ggaccaacgg ttaaacgttt atatgatgag     960
ttggttggca ttcagtttgg tgatgttgaa gcaccagaag ctggatagt aaagttgat     1020
taa                                                                  1023
```

<210> SEQ ID NO 68
<211> LENGTH: 340
<212> TYPE: PRT
<213> ORGANISM: Lactococcus lactis

<400> SEQUENCE: 68

```
Met Ala Ile Asn Leu Asp Trp Glu Asn Leu Gly Phe Ser Tyr Arg Asn
1               5                   10                  15

Leu Pro Phe Arg Tyr Ile Ala Arg Phe Lys Asp Gly Lys Trp Ser Ala
            20                  25                  30

Gly Glu Leu Thr Gly Asp Asn Gln Leu His Ile Ser Glu Ser Ser Pro
        35                  40                  45

Ala Leu His Tyr Gly Gln Gln Gly Phe Glu Gly Leu Lys Ala Tyr Arg
    50                  55                  60

Thr Lys Asp Gly Ser Ile Gln Leu Phe Arg Pro Asp Gln Asn Ala Ala
65                  70                  75                  80

Arg Leu Gln Asn Thr Ala Arg Arg Leu Cys Met Ala Glu Val Pro Thr
                85                  90                  95

Glu Met Phe Ile Asp Ala Val Lys Gln Val Val Lys Ala Asn Glu Asp
```

|     |     |     |     | 100 |     |     |     | 105 |     |     |     | 110 |     |     |
| --- | --- | --- | --- | --- | --- | --- | --- | --- | --- | --- | --- | --- | --- | --- |
| Phe | Val | Pro | Pro | Tyr | Gly | Thr | Gly | Ala | Thr | Leu | Tyr | Leu | Arg | Pro | Leu |

Phe Val Pro Pro Tyr Gly Thr Gly Ala Thr Leu Tyr Leu Arg Pro Leu
100             105                 110

Leu Ile Gly Val Gly Asp Val Ile Gly Val Lys Pro Ala Asp Glu Tyr
    115                 120                 125

Ile Phe Thr Val Phe Ala Met Pro Val Gly Ser Tyr Phe Lys Gly Gly
130             135                 140

Leu Ala Pro Ser Lys Phe Val Ile Ser Arg Asp Tyr Asp Arg Ala Ala
145             150                 155                 160

Pro Leu Gly Thr Gly Gly Ala Lys Val Gly Gly Asn Tyr Ala Ala Ser
    165                 170                 175

Leu Gln Ala Glu Val Gly Ala Lys Ala Ser Gly Tyr Ala Asp Ala Ile
    180                 185                 190

Tyr Leu Asp Pro Ser Thr His Thr Lys Ile Glu Val Gly Ala Ala
    195                 200                 205

Asn Phe Phe Gly Ile Thr Ala Asp Asn Glu Phe Ile Thr Pro Leu Ser
225             210                 215                 220

Pro Ser Ile Leu Pro Ser Ile Thr Lys Tyr Ser Leu Leu Tyr Leu Ala
225             230                 235                 240

Glu His Arg Leu Gly Leu Lys Ala Ile Glu Gly Glu Val Tyr Ala Lys
                245                 250                 255

Asp Leu Gly Lys Phe Val Glu Ala Gly Ala Cys Gly Thr Ala Ala Ile
    260                 265                 270

Ile Ser Pro Ile Gly Arg Ile Asp Asp Gly Glu Asp Ser Tyr Ile Phe
    275                 280                 285

His Ser Glu Thr Glu Val Gly Pro Thr Val Lys Arg Leu Tyr Asp Glu
305             290                 295                 300

Leu Val Gly Ile Gln Phe Gly Asp Val Glu Ala Pro Glu Gly Trp Ile
                310                 315                 320

Val Lys Val Asp
        325                 330                 335

340

<210> SEQ ID NO 69
<211> LENGTH: 1503
<212> TYPE: DNA
<213> ORGANISM: Saccharomyces cerevisiae

<400> SEQUENCE: 69

```
atgactttac ctgaatcaaa agacttttct tacttgtttt cggatgaaac caatgctcgt      60
aaaccatccc cattgaaaac ctgcatccat cttttccaag atcctaacat tatctttttg     120
ggtggtggcc tgccattaaa agattatttc ccatgggata atctatctgt agattcaccc     180
aagcctcctt ttccccaggg tattggagct ccaattgacg agcagaattg cataaaatac     240
accgtcaaca aagattacgc tgataaaagt gccaatcctt ccaacgatat tcctttgtca     300
agagctttgc aatacgggtt cagtgctggt caacctgaac tattaaactt cattagagat     360
cataccaaga ttatccacga tttgaagtat aaggactggg acgttttagc cactgcaggt     420
aacacaaatg cctgggaatc tactttaaga gtcttttgta accgaggtga tgtcatctta     480
gttgaggcac attctttttc ctcttcattg gcttctgcag aggctcaagg tgtcattacc     540
ttccccgtgc caattgacgc tgatggtatc attcctgaaa aattagctaa agtcatggaa     600
aactggacac ctggtgctcc taaaccaaag ttgttataca ctattccaac gggccaaaat     660
ccaactggta cttccattgc agaccataga aggaggcaa tttacaagat cgctcaaaag     720
```

```
tacgacttcc taattgtgga agatgaacct tattatttct tacaaatgaa tccctacatc    780
aaagacttga aggaaagaga gaaggcacaa agttctccaa agcaggacca tgacgaattt    840
ttgaagtcct tggcaaacac tttcctttcc tggatacag aaggccgtgt tattagaatg    900 gattccttt caaagtttt ggccccaggg acaagattgg gttggattac tggttcatcc    960
aaaatcttga agccttactt gagtttgcat gaaatgacga ttcaagcccc agcaggtttt   1020
acacaagttt tggtcaacgc tacgctatcc aggtggggtc aaaagggtta cttggactgg   1080
ttgcttggcc tgcgtcatga atacactttg aaacgtgact gtgccatcga tgcccttta   1140 aagtatctac cacaatctga tgctttcgtg atcaatcctc caattgcagg tatgttttc   1200 accgtgaaca ttgacgcatc tgtccaccct gagtttaaaa caaaatacaa ctcagaccct   1260
taccagctag aacagagtct ttaccacaaa gtggttgaac gtggtgtttt agtggttccc   1320
ggttcttggt tcaagagtga gggtgagacg gaacctcctc aacccgctga atctaaagaa   1380
gtcagtaatc caaacataat tttcttcaga ggtacctatg cagctgtctc tcctgagaaa   1440
ctgactgaag gtctgaagag attaggtgat actttatacg aagaatttgg tatttccaaa   1500
tag                                                                 1503
```

<210> SEQ ID NO 70
<211> LENGTH: 500
<212> TYPE: PRT
<213> ORGANISM: Saccharomyces cerevisiae

<400> SEQUENCE: 70

```
Met Thr Leu Pro Glu Ser Lys Asp Phe Ser Tyr Leu Phe Ser Asp Glu
1               5                   10                  15

Thr Asn Ala Arg Lys Pro Ser Pro Leu Lys Thr Cys Ile His Leu Phe
            20                  25                  30

Gln Asp Pro Asn Ile Ile Phe Leu Gly Gly Gly Leu Pro Leu Lys Asp
        35                  40                  45

Tyr Phe Pro Trp Asp Asn Leu Ser Val Asp Ser Pro Lys Pro Pro Phe
    50                  55                  60

Pro Gln Gly Ile Gly Ala Pro Ile Asp Glu Gln Asn Cys Ile Lys Tyr
65                  70                  75                  80

Thr Val Asn Lys Asp Tyr Ala Asp Lys Ser Ala Asn Pro Ser Asn Asp
                85                  90                  95

Ile Pro Leu Ser Arg Ala Leu Gln Tyr Gly Phe Ser Ala Gly Gln Pro
            100                 105                 110

Glu Leu Leu Asn Phe Ile Arg Asp His Thr Lys Ile Ile His Asp Leu
        115                 120                 125

Lys Tyr Lys Asp Trp Asp Val Leu Ala Thr Ala Gly Asn Thr Asn Ala
    130                 135                 140

Trp Glu Ser Thr Leu Arg Val Phe Cys Asn Arg Gly Asp Val Ile Leu
145                 150                 155                 160

Val Glu Ala His Ser Phe Ser Ser Leu Ala Ser Ala Glu Ala Gln
                165                 170                 175

Gly Val Ile Thr Phe Pro Val Pro Ile Asp Ala Asp Gly Ile Ile Pro
            180                 185                 190

Glu Lys Leu Ala Lys Val Met Glu Asn Trp Thr Pro Gly Ala Pro Lys
        195                 200                 205

Pro Lys Leu Leu Tyr Thr Ile Pro Thr Gly Gln Asn Pro Thr Gly Thr
    210                 215                 220

Ser Ile Ala Asp His Arg Lys Glu Ala Ile Tyr Lys Ile Ala Gln Lys
```

```
            225                 230                 235                 240
Tyr Asp Phe Leu Ile Val Glu Asp Glu Pro Tyr Tyr Phe Leu Gln Met
                245                 250                 255

Asn Pro Tyr Ile Lys Asp Leu Lys Glu Arg Glu Lys Ala Gln Ser Ser
                260                 265                 270

Pro Lys Gln Asp His Asp Glu Phe Leu Lys Ser Leu Ala Asn Thr Phe
                275                 280                 285

Leu Ser Leu Asp Thr Glu Gly Arg Val Ile Arg Met Asp Ser Phe Ser
290                 295                 300

Lys Val Leu Ala Pro Gly Thr Arg Leu Gly Trp Ile Thr Gly Ser Ser
305                 310                 315                 320

Lys Ile Leu Lys Pro Tyr Leu Ser Leu His Glu Met Thr Ile Gln Ala
                325                 330                 335

Pro Ala Gly Phe Thr Gln Val Leu Val Asn Ala Thr Leu Ser Arg Trp
                340                 345                 350

Gly Gln Lys Gly Tyr Leu Asp Trp Leu Leu Gly Leu Arg His Glu Tyr
                355                 360                 365

Thr Leu Lys Arg Asp Cys Ala Ile Asp Ala Leu Tyr Lys Tyr Leu Pro
370                 375                 380

Gln Ser Asp Ala Phe Val Ile Asn Pro Pro Ile Ala Gly Met Phe Phe
385                 390                 395                 400

Thr Val Asn Ile Asp Ala Ser Val His Pro Glu Phe Lys Thr Lys Tyr
                405                 410                 415

Asn Ser Asp Pro Tyr Gln Leu Glu Gln Ser Leu Tyr His Lys Val Val
                420                 425                 430

Glu Arg Gly Val Leu Val Pro Gly Ser Trp Phe Lys Ser Glu Gly
                435                 440                 445

Glu Thr Glu Pro Pro Gln Pro Ala Glu Ser Lys Glu Val Ser Asn Pro
                450                 455                 460

Asn Ile Ile Phe Phe Arg Gly Thr Tyr Ala Ala Val Ser Pro Glu Lys
465                 470                 475                 480

Leu Thr Glu Gly Leu Lys Arg Leu Gly Asp Thr Leu Tyr Glu Glu Phe
                485                 490                 495

Gly Ile Ser Lys
            500

<210> SEQ ID NO 71
<211> LENGTH: 33
<212> TYPE: DNA
<213> ORGANISM: Artificial Sequence
<220> FEATURE:
<223> OTHER INFORMATION: Primer for amplification

<400> SEQUENCE: 71
cacgaggtac atatgtctga aattgttgtc tcc                               33

<210> SEQ ID NO 72
<211> LENGTH: 29
<212> TYPE: DNA
<213> ORGANISM: Artificial Sequence
<220> FEATURE:
<223> OTHER INFORMATION: Primer for amplification

<400> SEQUENCE: 72
cttccagggg atccagtatt tactcaaac                                    29

<210> SEQ ID NO 73
```

<211> LENGTH: 1350
<212> TYPE: DNA
<213> ORGANISM: Artificial Sequence
<220> FEATURE:
<223> OTHER INFORMATION: Primer for amplification

<400> SEQUENCE: 73

| | |
|---|---|
| atgtctgaaa ttgttgtctc caaatttggc ggtaccagcg tagctgattt tgacgccatg | 60 |
| aaccgcagcg ctgatattgt gcttctgat gccaacgtgc gtttagttgt cctctcggct | 120 |
| tctgctggta tcactaatct gctggtcgct ttagctgaag gactggaacc tggcgagcga | 180 |
| ttcgaaaaac tcgacgctat ccgcaacatc cagtttgcca ttctggaacg tctgcgttac | 240 |
| ccgaacgtta tccgtgaaga gattgaacgt ctgctggaga acattactgt tctggcagaa | 300 |
| gcggcggcgc tggcaacgtc tccggcgctg acagatgagc tggtcagcca cggcgagctg | 360 |
| atgtcgaccc tgctgtttgt tgagatcctg cgcgaacgcg atgttcaggc acagtggttt | 420 |
| gatgtacgta aagtgatgcg taccaacgac cgatttggtc gtgcagagcc agatatagcc | 480 |
| gcgctggcgg aactggccgc gctgcagctg ctcccacgtc tcaatgaagg cttagtgatc | 540 |
| acccagggat ttatcggtag cgaaaataaa ggtcgtacaa cgacgcttgg ccgtggaggc | 600 |
| agcgattata cggcagcctt gctggcggag gctttcacacg catctcgtgt tgatatctgg | 660 |
| accgacgtcc cgggcatcta caccaccgat ccacgcgtag tttccgcagc aaaacgcatt | 720 |
| gatgaaatcg cgtttgccga agcggcagag atggcaactt tggtgcaaa agtactgcat | 780 |
| ccggcaacgt tgctacccgc agtacgcagc gatatcccgg tctttgtcgg ctccagcaaa | 840 |
| gacccacgcg caggtggtac gctggtgtgc aataaaactg aaaatccgcc gctgttccgc | 900 |
| gctctggcgc ttcgtcgcaa tcagactctg ctcactttgc acagcctgaa tatgctgcat | 960 |
| tctcgcggtt tcctcgcgga agttttcggc atcctcgcgc ggcataatat ttcggtagac | 1020 |
| ttaatcacca cgtcagaagt gagcgtggca ttaacccttg ataccaccgg ttcaacctcc | 1080 |
| actggcgata cgttgctgac gcaatctctg ctgatggagc tttccgcact gtgtcgggtg | 1140 |
| gaggtggaag aaggtctggc gctggtcgcg ttgattggca atgacctgtc aaaagcctgc | 1200 |
| ggcgttggca agaggtatt cggcgtactg gaaccgttca acattcgcat gatttgttat | 1260 |
| ggcgcatcca gccataacct gtgcttcctg gtgcccggcg aagatgccga gcaggtggtg | 1320 |
| caaaaactgc atagtaattt gtttgagtaa | 1350 |

<210> SEQ ID NO 74
<211> LENGTH: 34
<212> TYPE: DNA
<213> ORGANISM: Artificial Sequence
<220> FEATURE:
<223> OTHER INFORMATION: Primer for amplification

<400> SEQUENCE: 74

| | |
|---|---|
| gcgtttgccg aagcggcaaa gatggccact tttg | 34 |

<210> SEQ ID NO 75
<211> LENGTH: 34
<212> TYPE: DNA
<213> ORGANISM: Artificial Sequence
<220> FEATURE:
<223> OTHER INFORMATION: Primer for amplification

<400> SEQUENCE: 75

| | |
|---|---|
| caaaagtggc catctttgcc gcttcggcaa acgc | 34 |

-continued

```
<210> SEQ ID NO 76
<211> LENGTH: 35
<212> TYPE: DNA
<213> ORGANISM: Artificial Sequence
<220> FEATURE:
<223> OTHER INFORMATION: Primer for amplification

<400> SEQUENCE: 76
tataatgcta gcatgaaaaa tgttggtttt atcgg                               35

<210> SEQ ID NO 77
<211> LENGTH: 31
<212> TYPE: DNA
<213> ORGANISM: Artificial Sequence
<220> FEATURE:
<223> OTHER INFORMATION: Primer for amplification

<400> SEQUENCE: 77
tataatggat ccttacgcca gttgacgaag c                                   31

<210> SEQ ID NO 78
<211> LENGTH: 31
<212> TYPE: DNA
<213> ORGANISM: Artificial Sequence
<220> FEATURE:
<223> OTHER INFORMATION: Primer for amplification

<400> SEQUENCE: 78
tataatcata tgagcactaa agttgttaat g                                   31

<210> SEQ ID NO 79
<211> LENGTH: 31
<212> TYPE: DNA
<213> ORGANISM: Artificial Sequence
<220> FEATURE:
<223> OTHER INFORMATION: Primer for amplification

<400> SEQUENCE: 79
tataatggat ccctaaagtc tttgagcaat c                                   31

<210> SEQ ID NO 80
<211> LENGTH: 42
<212> TYPE: DNA
<213> ORGANISM: Artificial Sequence
<220> FEATURE:
<223> OTHER INFORMATION: Primer for amplification

<400> SEQUENCE: 80
tataaggatc cgtttaactt taagaaggag ataccatg gg                         42

<210> SEQ ID NO 81
<211> LENGTH: 29
<212> TYPE: DNA
<213> ORGANISM: Artificial Sequence
<220> FEATURE:
<223> OTHER INFORMATION: Primer for amplification

<400> SEQUENCE: 81
tataagaatt cttacgccag ttgacgaag                                      29

<210> SEQ ID NO 82
<211> LENGTH: 36
<212> TYPE: DNA
<213> ORGANISM: Artificial Sequence
<220> FEATURE:
<223> OTHER INFORMATION: Primer for amplification
```

```
<400> SEQUENCE: 82
tataagcggc cgcgtttaac tttaagaagg agatat                              36

<210> SEQ ID NO 83
<211> LENGTH: 31
<212> TYPE: DNA
<213> ORGANISM: Artificial Sequence
<220> FEATURE:
<223> OTHER INFORMATION: Primer for amplification

<400> SEQUENCE: 83
tataaactcg agcctaaagt ctttgagcaa t                                   31

<210> SEQ ID NO 84
<211> LENGTH: 29
<212> TYPE: DNA
<213> ORGANISM: Artificial Sequence
<220> FEATURE:
<223> OTHER INFORMATION: Primer for amplification

<400> SEQUENCE: 84 tataagatc ttagaaataa ttttgttta                                       29

<210> SEQ ID NO 85
<211> LENGTH: 29
<212> TYPE: DNA
<213> ORGANISM: Artificial Sequence
<220> FEATURE:
<223> OTHER INFORMATION: Primer for amplification

<400> SEQUENCE: 85
tataatctag actaaagtct tgagcaat                                       29

<210> SEQ ID NO 86
<211> LENGTH: 28
<212> TYPE: DNA
<213> ORGANISM: Artificial Sequence
<220> FEATURE:
<223> OTHER INFORMATION: Primer for amplification

<400> SEQUENCE: 86
tataatcata tgcgagtgtt gaagttcg                                       28

<210> SEQ ID NO 87
<211> LENGTH: 30
<212> TYPE: DNA
<213> ORGANISM: Artificial Sequence
<220> FEATURE:
<223> OTHER INFORMATION: Primer for amplification

<400> SEQUENCE: 87
tataatggat cctcagactc ctaacttcca                                     30

<210> SEQ ID NO 88
<211> LENGTH: 2463
<212> TYPE: DNA
<213> ORGANISM: Escherichia coli

<400> SEQUENCE: 88
atgcgagtgt tgaagttcgg cggtacatca gtggcaaatg cagaacgttt tctgcgtgtt    60
gccgatattc tggaaagcaa tgccaggcag gggcaggtgg ccaccgtcct ctctgccccc    120
gccaaaatca ccaaccacct ggtggcgatg attgaaaaaa ccattagcgg ccaggatgct    180
ttacccaata tcagcgatgc cgaacgtatt tttgccgaac ttttgacggg actcgccgcc    240
```

```
gcccagccgg ggttcccgct ggcgcaattg aaaactttcg tcgatcagga atttgcccaa    300
ataaaacatg tcctgcatgg cattagtttg ttggggcagt gcccggatag catcaacgct    360
gcgctgattt gccgtggcga gaaaatgtcg atcgccatta tggccggcgt attagaagcg    420
cgcggtcaca acgttactgt tatcgatccg gtcgaaaaac tgctggcagt ggggcattac    480
ctcgaatcta ccgtcgatat tgctgagtcc acccgccgta ttgcggcaag ccgcattccg    540
gctgatcaca tggtgctgat ggcaggtttc accgccggta tgaaaaagg cgaactggtg     600 gtgcttggac gcaacggttc cgactactct gctgcggtgc tggctgcctg tttacgcgcc    660
gattgttgcg agatttggac ggacgttgac ggggtctata cctgcgaccc gcgtcaggtg    720
cccgatgcga ggttgttgaa gtcgatgtcc taccaggaag cgatggagct ttcctacttc    780
ggcgctaaag ttcttcaccc ccgcaccatt accccccatcg cccagttcca gatcccttgc   840
ctgattaaaa ataccggaaa tcctcaagca ccaggtacgc tcattggtgc cagccgtgat   900
gaagacgaat taccggtcaa gggcatttcc aatctgaata acatggcaat gttcagcgtt   960
tctggtccgg ggatgaaagg gatggtcggc atggcggcgc gcgtctttgc agcgatgtca  1020
cgcgcccgta tttccgtggt gctgattacg caatcatctt ccgaatacag catcagtttc  1080
tgcgttccac aaagcgactg tgtgcgagct gaacgggcaa tgcaggaaga gttctacctg  1140
gaactgaaag aaggcttact ggagccgctg gcagtgacgg aacggctggc cattatctcg  1200
gtggtaggtg atggtatgcg caccttgcgt gggatctcgg cgaaattctt tgccgcactg  1260
gcccgcgcca atatcaacat tgtcgccatt gctcagggat cttctgaacg ctcaatctct  1320
gtcgtggtaa ataacgatga tgcgaccact ggcgtgcgcg ttactcatca gatgctgttc  1380
aataccgatc aggttatcga agtgtttgtg attggcgtcg gtggcgttgg cggtgcgctg  1440
ctggagcaac tgaagcgtca gcaaagctgg ctgaagaata acatatcga cttacgtgtc  1500 tgcggtgttg ccaactcgaa ggctctgctc accaatgtac atggccttaa tctggaaaac  1560
tggcaggaag aactggcgca agccaaagag ccgtttaatc tcgggcgctt aattcgcctc  1620
gtgaaagaat atcatctgct gaacccggtc attgttgact gcacttccag ccaggcagtg  1680
gcggatcaat atgccgactt cctgcgcgaa ggtttccacg ttgtcacgcc gaacaaaaag  1740
gccaacacct cgtcgatgga ttactaccat cagttgcgtt atgcggcgga aaaatcgcgg  1800
cgtaaattcc tctatgacac caacgttggg gctggattac cggttattga gaacctgcaa  1860
aatctgctca atgcaggtga tgaattgatg aagttctccg gcattctttc tggttcgctt  1920
tcttatatct tcggcaagtt agacgaaggc atgagtttct ccgaggcgac cacgctggcg  1980
cgggaaatgg gttataccga accggacccg cgagatgatc tttctggtat ggatgtggcg  2040
cgtaaactat tgattctcgc tcgtgaaacg ggacgtgaac tggagctggc ggatattgaa  2100
attgaacctg tgctgcccgc agagtttaac gccgagggtg atgttgccgc ttttatggcg  2160
aatctgtcac aactcgacga tctctttgcc gcgcgcgtgg cgaaggcccg tgatgaagga  2220
aaagttttgc gctatgttgg caatattgat gaagatggcg tctgccgcgt gaagattgcc  2280
gaagtggatg gtaatgatcc gctgttcaaa gtgaaaaatg gcgaaaacgc cctggccttc  2340
tatagccact attatcagcc gctgccgttg gtactgcgcg atatggtgc gggcaatgac  2400 gttacagctg ccggtgtctt tgctgatctg ctacgtaccc tctcatggaa gttaggagtc  2460
tga                                                                2463
```

<210> SEQ ID NO 89

```
<211> LENGTH: 820
<212> TYPE: PRT
<213> ORGANISM: Escherichia coli

<400> SEQUENCE: 89

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285

Gln Ala Pro Gly Thr Leu Ile Gly Ala Ser Arg Asp Glu Asp Glu Leu
290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
370                 375                 380

Gly Leu Leu Glu Pro Leu Ala Val Thr Glu Arg Leu Ala Ile Ile Ser
```

```
                385                 390                 395                 400
Val Val Gly Asp Gly Met Arg Thr Leu Arg Gly Ile Ser Ala Lys Phe
                    405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Asn Asn Asp Asp Ala
            435                 440                 445

Thr Thr Gly Val Arg Val Thr His Gln Met Leu Phe Asn Thr Asp Gln
        450                 455                 460

Val Ile Glu Val Phe Val Ile Gly Val Gly Val Gly Gly Ala Leu
465                 470                 475                 480

Leu Glu Gln Leu Lys Arg Gln Gln Ser Trp Leu Lys Asn Lys His Ile
            485                 490                 495

Asp Leu Arg Val Cys Gly Val Ala Asn Ser Lys Ala Leu Leu Thr Asn
                500                 505                 510

Val His Gly Leu Asn Leu Glu Asn Trp Gln Glu Glu Leu Ala Gln Ala
            515                 520                 525

Lys Glu Pro Phe Asn Leu Gly Arg Leu Ile Arg Leu Val Lys Glu Tyr
        530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
        595                 600                 605

Val Gly Ala Gly Leu Pro Val Ile Glu Asn Leu Gln Asn Leu Leu Asn
        610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
        675                 680                 685

Glu Thr Gly Arg Glu Leu Glu Leu Ala Asp Ile Glu Ile Glu Pro Val
        690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
                725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
        755                 760                 765

Phe Lys Val Lys Asn Gly Glu Asn Ala Leu Ala Phe Tyr Ser His Tyr
        770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
                805                 810                 815
```

Lys Leu Gly Val
          820

<210> SEQ ID NO 90
<211> LENGTH: 29
<212> TYPE: DNA
<213> ORGANISM: Artificial Sequence
<220> FEATURE:
<223> OTHER INFORMATION: Primer for amplification

<400> SEQUENCE: 90
tgtctcgagc ccgtatttc gtggtgctg                                    29

<210> SEQ ID NO 91
<211> LENGTH: 29
<212> TYPE: DNA
<213> ORGANISM: Artificial Sequence
<220> FEATURE:
<223> OTHER INFORMATION: Primer for amplification

<400> SEQUENCE: 91
cagcaccacg aaaatacggg ctcgagaca                                   29

<210> SEQ ID NO 92
<211> LENGTH: 2463
<212> TYPE: DNA
<213> ORGANISM: Artificial Sequence
<220> FEATURE:
<223> OTHER INFORMATION: plasmid

<400> SEQUENCE: 92
atgcgagtgt tgaagttcgg cggtacatca gtggcaaatg cagaacgttt tctgcgtgtt      60
gccgatattc tggaaagcaa tgccaggcag gggcaggtgg ccaccgtcct ctctgccccc     120
gccaaaatca ccaaccacct ggtggcgatg attgaaaaaa ccattagcgg ccaggatgct     180
ttacccaata tcagcgatgc cgaacgtatt tttgccgaac ttttgacggg actcgccgcc     240
gcccagccgg ggttcccgct ggcgcaattg aaaactttcg tcgatcagga atttgcccaa     300
ataaaacatg tcctgcatgg cattagtttg ttggggcagt gcccggatag catcaacgct     360
gcgctgattt gccgtggcga aaaatgtcg atcgccatta tggccggcgt attagaagcg     420
cgcggtcaca cgttactgt tatcgatccg gtcgaaaaac tgctggcagt ggggcattac     480
ctcgaatcta ccgtcgatat tgctgagtcc accgccgta ttgcggcaag ccgcattccg     540
gctgatcaca tggtgctgat ggcaggtttc accgccggta atgaaaaagg cgaactggtg     600
gtgcttggac gcaacggttc cgactactct gctgcggtgc tggctgcctg tttacgcgcc     660
gattgttgcg agatttggac ggacgttgac ggggtctata cctgcgaccc cgtcaggtg     720 cccgatgcga ggttgttgaa gtcgatgtcc taccaggaag cgatggagct ttcctacttc     780
ggcgctaaag ttcttcaccc ccgcaccatt accccatcg cccagttcca gatcccttgc     840
ctgattaaaa ataccggaaa tcctcaagca ccaggtacgc tcattggtgc cagccgtgat     900
gaagacgaat accggtcaa gggcatttcc aatctgaata acatggcaat gttcagcgtt     960
tctggtccgg ggatgaaagg gatggtcggc atggcgcgc cgtctttgc agcgatgtct    1020 cgagcccgta ttttcgtggt gctgattacg caatcatctt ccgaatacag catcagtttc    1080
tgcgttccac aaagcgactg tgtgcgagct gaacgggcaa tgcaggaaga gttctacctg    1140
gaactgaaag aaggcttact ggagccgctg gcagtgacga acggctggc cattatctcg    1200 gtggtaggtg atggtatgcg caccttgcgt gggatctcgg cgaaattctt tgccgcactg    1260

```
gcccgcgcca atatcaacat tgtcgccatt gctcagggat cttctgaacg ctcaatctct    1320
gtcgtggtaa ataacgatga tgcgaccact ggcgtgcgcg ttactcatca gatgctgttc    1380
aataccgatc aggttatcga agtgtttgtg attggcgtcg gtggcgttgg cggtgcgctg    1440
ctggagcaac tgaagcgtca gcaaagctgg ctgaagaata acatatcga cttacgtgtc    1500 tgcggtgttg ccaactcgaa ggctctgctc accaatgtac atggccttaa tctggaaaac    1560
tggcaggaag aactggcgca agccaaagag ccgtttaatc tcgggcgctt aattcgcctc    1620
gtgaaagaat atcatctgct gaacccggtc attgttgact gcacttccag ccaggcagtg    1680
gcggatcaat atgccgactt cctgcgcgaa ggtttccacg ttgtcacgcc gaacaaaaag    1740
gccaacacct cgtcgatgga ttactaccat cagttgcgtt atgcggcgga aaaatcgcgg    1800
cgtaaattcc tctatgacac caacgttggg gctggattac cggttattga gaacctgcaa    1860
aatctgctca atgcaggtga tgaattgatg aagttctccg gcattctttc tggttcgctt    1920
tcttatatct tcggcaagtt agacgaaggc atgagtttct ccgaggcgac cacgctggcg    1980
cgggaaatgg gttataccga accggacccg cgagatgatc tttctggtat ggatgtggcg    2040
cgtaaactat tgattctcgc tcgtgaaacg ggacgtgaac tggagctggc ggatattgaa    2100
attgaacctg tgctgcccgc agagtttaac gccgagggtg atgttgccgc tttatggcg    2160 aatctgtcac aactcgacga tctctttgcc gcgcgcgtgg cgaaggcccg tgatgaagga    2220
aaagttttgc gctatgttgg caatattgat gaagatggcg tctgccgcgt gaagattgcc    2280
gaagtggatg gtaatgatcc gctgttcaaa gtgaaaaatg cgaaaacgc cctggccttc    2340 tatagccact attatcagcc gctgccgttg gtactgcgcg gatatggtgc gggcaatgac    2400
gttacagctg ccggtgtctt tgctgatctg ctacgtaccc tctcatggaa gttaggagtc    2460
tga                                                                 2463
```

<210> SEQ ID NO 93
<211> LENGTH: 60
<212> TYPE: DNA
<213> ORGANISM: Artificial Sequence
<220> FEATURE:
<223> OTHER INFORMATION: Primer for amplification

<400> SEQUENCE: 93

```
tataatgagc tcgtttaact ttaagaagga gatataccat gcgagtgttg aagttcggcg    60
```

<210> SEQ ID NO 94
<211> LENGTH: 30
<212> TYPE: DNA
<213> ORGANISM: Artificial Sequence
<220> FEATURE:
<223> OTHER INFORMATION: Primer for amplification

<400> SEQUENCE: 94

```
tataatcccg ggtcagactc ctaacttcca                                     30
```

<210> SEQ ID NO 95
<211> LENGTH: 62
<212> TYPE: DNA
<213> ORGANISM: Artificial Sequence
<220> FEATURE:
<223> OTHER INFORMATION: Primer for amplification

<400> SEQUENCE: 95

```
tataatcccg gggtttaact ttaagaagga gatataccat gaaaaatgtt ggttttatcg    60
```

<210> SEQ ID NO 96
<211> LENGTH: 30
<212> TYPE: DNA
<213> ORGANISM: Artificial Sequence
<220> FEATURE:
<223> OTHER INFORMATION: Primer for amplification

<400> SEQUENCE: 96

```
tataatggat ccttacgcca gttgacgaag                               30
```

<210> SEQ ID NO 97
<211> LENGTH: 1080
<212> TYPE: DNA
<213> ORGANISM: Artificial Sequence
<220> FEATURE:
<223> OTHER INFORMATION: plasmid

<400> SEQUENCE: 97

```
atgagcacta aagttgttaa tgttgccgtt atcggtgccg gtgttgttgg ttcagctttc    60
ttggatcaat tgttagccat gaagtctacc attacttaca atctagttct tttggctgaa   120
gctgagcgtt ctttaatctc caaggacttt tctccattaa atgttggttc tgattggaag   180
gctgctttag cagcctccac tactaaaacg ttgcctttgg atgatttaat tgctcatttg   240
aagacttcac ctaagccagt cattttggtt gataacactt ccagcgctta cattgctggt   300
ttttacacta gtttgtcga aatggtatt ccattgcta ctccaaacaa gaaggccttt   360
tcctctgatt tggctacctg gaaggctctt ttctcaaata gccaactaa cggttttgtc   420
tatcatgaag ctaccgtcgg tgctggtttg cctatcatca gtttcttaag agaaattatt   480
caaaccggtg acgaagttga aaaaattgaa ggtatcttct ctggtactct atcttatatt   540
ttcaacgagt tctccactag tcaagctaac gacgtcaaat tctctgatgt tgtcaaagtt   600
gctaaaaaat tgggttatac tgaaccagat ccaagagatg atttgaatgg ttggatgtt   660
gctagaaagg ttaccattgt tggtaggata tctggtgtgg aagttgaatc tccaacttcc   720
ttccctgtcc agtctttgat tccaaaacca ttggaatctg tcaagtctgc tgatgaattc   780
ttggaaaaat tatctgatta cgataaagat ttgactcaat gaagaagga agctgccact   840
gaaaataagg tattgagatt cattggtaaa gtcgatgttg ccaccaaatc tgtgtctgta   900
ggaattgaaa agtacgatta ctcacaccca ttcgcatcat tgaagggatc agataacgtt   960
atttccatca agactaagcg ttacaccaat cctgttgtca ttcaaggtgc cggtgccggt  1020
gctgccgtta ctgccgctgg tgttttgggt gatgttatca agattgctca aagactttag  1080
```

<210> SEQ ID NO 98
<211> LENGTH: 1104
<212> TYPE: DNA
<213> ORGANISM: Artificial Sequence
<220> FEATURE:
<223> OTHER INFORMATION: Primer for amplification

<400> SEQUENCE: 98

```
atgaaaaatg ttggttttat cggctggcgc ggtatggtcg gctccgttct catgcaacgc    60
atggttgaag agcgcgactt cgacgccatt cgccctgtct tcttttctac ttctcagctt   120
ggccaggctg cgccgtcttt tggcggaacc actggcacac ttcaggatgc ctttgatctg   180
gaggcgctaa aggccctcga tatcattgtg acctgtcagg gcggcgatta taccaacgaa   240
atctatccaa agcttcgtga aagcggatgg caaggttact ggattgacgc agcatcgtct  300
```

```
ctgcgcatga aagatgacgc catcatcatt cttgaccccg tcaatcagga cgtcattacc    360
gacggattaa ataatggcat caggacttt t gttggcggta actgtaccgt aagcctgatg    420
ttgatgtcgt tgggtggttt attcgccaat gatcttgttg attgggtgtc cgttgcaacc    480
taccaggccg cttccggcgg tggtgcgcga catatgcgtg agttattaac ccagatgggc    540
catctgtatg ccatgtggc agatgaactc gcgaccccgt cctctgctat tctcgatatc    600
gaacgcaaag tcacaacctt aacccgtagc ggtgagctgc cggtggataa ctttggcgtg    660
ccgctggcgg gtagcctgat tccgtggatc gacaaacagc tcgataacgg tcagagccgc    720
gaagagtgga agggcaggc ggaaaccaac aagatcctca acacatcttc cgtaattccg    780
gtagatggtt tatgtgtgcg tgtcggggca ttgcgctgcc acagccaggc attcactatt    840
aaattgaaaa aagatgtgtc tattccgacc gtggaagaac tgctggctgc gcacaatccg    900
tgggcgaaag tcgttccgaa cgatcgggaa atcactatgc gtgagctaac cccagctgcc    960
gttaccggca cgctgaccac gccggtaggc cgcctgcgta agctgaatat gggaccagag   1020
ttcctgtcag ccttttaccgt gggcgaccag ctgctgtggg gggccgcgga gccgctgcgt   1080
cggatgcttc gtcaactggc gtaa                                          1104

<210> SEQ ID NO 99
<211> LENGTH: 37
<212> TYPE: DNA
<213> ORGANISM: Artificial Sequence
<220> FEATURE:
<223> OTHER INFORMATION: Primer for amplification

<400> SEQUENCE: 99
cgtgatgctg cttactcgat cgtcgctaaa aaaggtg                             37

<210> SEQ ID NO 100
<211> LENGTH: 37
<212> TYPE: DNA
<213> ORGANISM: Artificial Sequence
<220> FEATURE:
<223> OTHER INFORMATION: Primer for amplification

<400> SEQUENCE: 100
cacctttttt agcgacgatc gagtaagcag catcacg                             37

<210> SEQ ID NO 101
<211> LENGTH: 939
<212> TYPE: DNA
<213> ORGANISM: Escherichia coli

<400> SEQUENCE: 101
atgaaagtcg cagtcctcgg cgctgctggc ggtattggcc aggcgcttgc actactgtta     60
aaaacccaac tgccttcagg ttcagaactc tctctgtatg atatcgctcc agtgactccc    120
ggtgtggctg tcgatctgag ccatatccct actgctgtga aaatcaaagg ttttttctggt    180 gaagatgcga ctccggcgct ggaaggcgca gatgtcgttc ttatctctgc aggcgtagcg    240
gctaaacccg ggatggatcg ttccgacctg tttaacgtta cgccggcat cgtgaaaaac    300 ctggtacagc aagttgcgaa aacctgcccg aaagcgtgca ttggtattat cactaacccg    360
gttaacacca cagttgcaat tgctgctgaa gtgctgaaaa agccggtgt ttatgacaaa    420 aacaaactgt tcggcgttac cacgctggat atcattcgtt ccaacacctt tgttgcggaa    480
ctgaaaggca aacagccagg cgaagttgaa gtgccggtta ttggcggtca ctctggtgtt    540
```

```
accattctgc cgctgctgtc acaggttcct ggcgttagtt ttaccgagca ggaagtggct    600
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt    720
gcactgcagg gcgaacaagg cgttgtcgaa tgtgcctacg ttgaaggcga cggtcagtac    780
gcccgtttct tctctcaacc gctgctgctg ggtaaaaacg gcgtggaaga gcgtaaatct    840
atcggtaccc tgagcgcatt tgaacagaac gcgctggaag gtatgctgga tacgctgaag    900
aaagatatcg ccctgggcga agagttcgtt aataagtaa                          939
```

```
<210> SEQ ID NO 102
<211> LENGTH: 317
<212> TYPE: PRT
<213> ORGANISM: Escherichia coli

<400> SEQUENCE: 102

Met Asp His Arg Ala Met Lys Val Ala Val Leu Gly Ala Ala Gly Gly
1               5                   10                  15

Ile Gly Gln Ala Leu Ala Leu Leu Lys Thr Gln Leu Pro Ser Gly
            20                  25                  30

Ser Glu Leu Ser Leu Tyr Asp Ile Ala Pro Val Thr Pro Gly Val Ala
        35                  40                  45

Val Asp Leu Ser His Ile Pro Thr Ala Val Lys Ile Lys Gly Phe Ser
50                  55                  60

Gly Glu Asp Ala Thr Pro Ala Leu Glu Gly Ala Asp Val Val Leu Ile
65                  70                  75                  80

Ser Ala Gly Val Ala Ala Lys Pro Gly Met Asp Arg Ser Asp Leu Phe
                85                  90                  95

Asn Val Asn Ala Gly Ile Val Lys Asn Leu Val Gln Gln Val Ala Lys
            100                 105                 110

Thr Cys Pro Lys Ala Cys Ile Gly Ile Ile Thr Asn Pro Val Asn Thr
        115                 120                 125

Thr Val Ala Ile Ala Ala Glu Val Leu Lys Lys Ala Gly Val Tyr Asp
    130                 135                 140

Lys Asn Lys Leu Phe Gly Val Thr Thr Leu Asp Ile Ile Arg Ser Asn
145                 150                 155                 160

Thr Phe Val Ala Glu Leu Lys Gly Lys Gln Pro Gly Glu Val Glu Val
                165                 170                 175

Pro Val Ile Gly Gly His Ser Gly Val Thr Ile Leu Pro Leu Leu Ser
            180                 185                 190

Gln Val Pro Gly Val Ser Phe Thr Glu Gln Glu Val Ala Asp Leu Thr
        195                 200                 205

Lys Arg Ile Gln Asn Ala Gly Thr Glu Val Val Glu Ala Lys Ala Gly
    210                 215                 220

Gly Gly Ser Ala Thr Leu Ser Met Gly Gln Ala Ala Ala Arg Phe Gly
225                 230                 235                 240

Leu Ser Leu Val Arg Ala Leu Gln Gly Glu Gln Gly Val Val Glu Cys
                245                 250                 255

Ala Tyr Val Glu Gly Asp Gly Gln Tyr Ala Arg Phe Phe Ser Gln Pro
            260                 265                 270

Leu Leu Leu Gly Lys Asn Gly Val Glu Glu Arg Lys Ser Ile Gly Thr
        275                 280                 285

Leu Ser Ala Phe Glu Gln Asn Ala Leu Glu Gly Met Leu Asp Thr Leu
    290                 295                 300
```

Lys Lys Asp Ile Ala Leu Gly Glu Glu Phe Val Asn Lys
305                 310                 315

<210> SEQ ID NO 103
<211> LENGTH: 939
<212> TYPE: DNA
<213> ORGANISM: Escherichia coli

<400> SEQUENCE: 103

| | |
|---|---|
| atgaaagtcg cagtcctcgg cgctgctggc ggtattggcc aggcgcttgc actactgtta | 60 |
| aaaacccaac tgccttcagg ttcagaactc tctctgtatg atatcgctcc agtgactccc | 120 |
| ggtgtggctg tcgatctgag ccatatccct actgctgtga aaatcaaagg ttttctggt | 180 |
| gaagatgcga ctccggcgct ggaaggcgca gatgtcgttc ttatctctgc aggcgtagcg | 240 |
| gctaaaccgg tcaggatcg ttccgacctg tttaacgtta acgccggcat cgtgaaaaac | 300 |
| ctggtacagc aagttgcgaa acctgcccg aaagcgtgca ttggtattat cactaacccg | 360 |
| gttaacacca cagttgcaat tgctgctgaa gtgctgaaaa agccggtgt ttatgacaaa | 420 |
| aacaaactgt tcggcgttac cacgctggat atcattcgtt ccaacacctt tgttgcggaa | 480 |
| ctgaaaggca acagccagg cgaagttgaa gtgccggtta ttggcggtca ctctggtgtt | 540 |
| accattctgc cgctgctgtc acaggttcct ggcgttagtt ttaccgagca ggaagtggct | 600 |
| gatctgacca aacgcatcca gaacgcgggt actgaagtgg ttgaagcgaa ggccggtggc | 660 |
| gggtctgcaa ccctgtctat gggccaggca gctgcacgtt ttggtctgtc tctggttcgt | 720 |
| gcactgcagg cgaacaagg cgttgtcgaa tgtgcctacg ttgaaggcga cggtcagtac | 780 |
| gcccgtttct tctctcaacc gctgctgctg gtaaaaacg gcgtggaaga gcgtaaatct | 840 |
| atcggtaccc tgagcgcatt tgaacagaac gcgctggaag gtatgctgga tacgctgaag | 900 |
| aaagatatcg ccctgggcga agagttcgtt aataagtaa | 939 |

<210> SEQ ID NO 104
<211> LENGTH: 312
<212> TYPE: PRT
<213> ORGANISM: Escherichia coli

<400> SEQUENCE: 104

Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
                20                  25                  30

Tyr Asp Ile Ala Pro Val Thr Pro Gly Val Ala Val Asp Leu Ser His
            35                  40                  45

Ile Pro Thr Ala Val Lys Ile Lys Gly Phe Ser Gly Glu Asp Ala Thr
        50                  55                  60

Pro Ala Leu Glu Gly Ala Asp Val Val Leu Ile Ser Ala Gly Val Ala
65                  70                  75                  80

Ala Lys Pro Gly Gln Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu

```
                145                 150                 155                 160
Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
                180                 185                 190

Ser Phe Thr Glu Gln Glu Val Ala Asp Leu Thr Lys Arg Ile Gln Asn
                195                 200                 205

Ala Gly Thr Glu Val Val Glu Ala Lys Ala Gly Gly Ser Ala Thr
                210                 215                 220

Leu Ser Met Gly Gln Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
                260                 265                 270

Asn Gly Val Glu Glu Arg Lys Ser Ile Gly Thr Leu Ser Ala Phe Glu
                275                 280                 285

Gln Asn Ala Leu Glu Gly Met Leu Asp Thr Leu Lys Lys Asp Ile Ala
                290                 295                 300

Leu Gly Glu Glu Phe Val Asn Lys
305                 310
```

```
<210> SEQ ID NO 105
<211> LENGTH: 939
<212> TYPE: DNA
<213> ORGANISM: Escherichia coli

<400> SEQUENCE: 105
```

| | | | | | |
|---|---|---|---|---|---|
| atgaaagtcg | cagtcctcgg | cgctgctggc | ggtattggcc | aggcgcttgc | actactgtta | 60 |
| aaacccaac | tgccttcagg | ttcagaactc | tctctgtatg | atatcgctcc | agtgactccc | 120 |
| ggtgtggctg | tcgatctgag | ccatatccct | actgctgtga | aaatcaaagg | ttttctggt | 180 |
| gaagatgcga | ctccggcgct | ggaaggcgca | gatgtcgttc | ttatctctgc | aggcgtagcg | 240 |
| gctaaaccgg | gtgaggatcg | ttccgacctg | tttaacgtta | acgccggcat | cgtgaaaaac | 300 |
| ctggtacagc | aagttgcgaa | acctgcccg | aaagcgtgca | ttggtattat | cactaacccg | 360 |
| gttaacacca | cagttgcaat | tgctgctgaa | gtgctgaaaa | agccggtgt | ttatgacaaa | 420 |
| aacaaactgt | tcggcgttac | cacgctggat | atcattcgtt | ccaacacctt | tgttgcggaa | 480 |
| ctgaaaggca | acagccagg | cgaagttgaa | gtgccggtta | ttggcggtca | ctctggtgtt | 540 |
| accattctgc | cgctgctgtc | acaggttcct | ggcgttagtt | ttaccgagca | ggaagtggct | 600 |
| gatctgacca | aacgcatcca | gaacgcgggt | actgaagtgg | ttgaagcgaa | ggccggtggc | 660 |
| gggtctgcaa | ccctgtctat | gggccaggca | gctgcacgtt | ttggtctgtc | tctggttcgt | 720 |
| gcactgcagg | gcgaacaagg | cgttgtcgaa | tgtgcctacg | ttgaaggcga | cggtcagtac | 780 |
| gcccgtttct | tctctcaacc | gctgctgctg | ggtaaaaacg | gcgtggaaga | gcgtaaatct | 840 |
| atcggtaccc | tgagcgcatt | tgaacagaac | gcgctggaag | gtatgctgga | tacgctgaag | 900 |
| aaagatatcg | ccctgggcga | agagttcgtt | aataagtaa | | | 939 |

```
<210> SEQ ID NO 106
<211> LENGTH: 312
<212> TYPE: PRT
<213> ORGANISM: Escherichia coli

<400> SEQUENCE: 106
```

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
            35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Glu Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
    290                 295                 300

Leu Gly Glu Glu Phe Val Asn Lys
305                 310

<210> SEQ ID NO 107
<211> LENGTH: 939
<212> TYPE: DNA
<213> ORGANISM: Escherichia coli

<400> SEQUENCE: 107
atgaaagtcg cagtcctcgg cgccgctggc ggtgtcggcc aggcgcttgc actactgtta    60 aaacccaac tgccttcagg ttcagaactc tctctgtatg atatcgctcc agtgactccc    120
ggtgtggctg tcgatctgag ccatatccct actgctgtga aaatcaaagg tttttctggt    180
gaagatgcga ctccggcgct ggaaggcgca gatgtcgttc ttatctctgc aggcgtagcg    240
gctaaaccgg gtcaggatcg ttccgacctg tttaacgtta acgccggcat cgtgaaaaac    300
```

```
ctggtacagc aagttgcgaa aacctgcccg aaagcgtgca ttggtattat cactaacccg    360
gttaacacca cagttgcaat tgctgctgaa gtgctgaaaa agccggtgt ttatgacaaa     420
aacaaactgt tcggcgttac cacgctggat atcattcgtt ccaacacctt tgttgcggaa    480
ctgaaaggca acagccagg cgaagttgaa gtgccggtta ttggcggtca ctctggtgtt     540
accattctgc cgctgctgtc acaggttcct ggcgttagtt ttaccgagca ggaagtggct    600
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt   720
gcactgcagg gcgaacaagg cgttgtcgaa tgtgcctacg ttgaaggcga cggtcagtac    780
gcccgtttct tctctcaacc gctgctgctg ggtaaaaacg gcgtggaaga gcgtaaatct    840
atcggtaccc tgagcgcatt tgaacagaac gcgctggaag gtatgctgga tacgctgaag    900
aaagatatcg ccctgggcga agagttcgtt aataagtaa                            939

<210> SEQ ID NO 108
<211> LENGTH: 312
<212> TYPE: PRT
<213> ORGANISM: Escherichia coli

<400> SEQUENCE: 108

Met Lys Val Ala Val Leu Gly Ala Ala Gly Gly Val Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Gln Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
```

```
              260                 265                 270
Asn Gly Val Glu Glu Arg Lys Ser Ile Gly Thr Leu Ser Ala Phe Glu
                275                 280                 285

Gln Asn Ala Leu Glu Gly Met Leu Asp Thr Leu Lys Lys Asp Ile Ala
        290                 295                 300

Leu Gly Glu Glu Phe Val Asn Lys
305                 310

<210> SEQ ID NO 109
<211> LENGTH: 939
<212> TYPE: DNA
<213> ORGANISM: Escherichia coli

<400> SEQUENCE: 109
atgaaagtcg cagtcctcgg cgccgctggc ggtgtcggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg ttttctggt     180 gaagatgcga ctccggcgct ggaaggcgca gatgtcgttc ttatctctgc aggcgtagcg     240
gctaaaccgg gtgaggatcg ttccgacctg tttaacgtta acgccggcat cgtgaaaaac     300
ctggtacagc aagttgcgaa acctgcccg aaagcgtgca ttggtattat cactaacccg     360
gttaacacca cagttgcaat tgctgctgaa gtgctgaaaa agccggtgt ttatgacaaa     420 aacaaactgt tcggcgttac cacgctggat atcattcgtt ccaacacctt tgttgcggaa     480
ctgaaaggca acagccagg cgaagttgaa gtgccggtta ttggcggtca ctctggtgtt     540
accattctgc cgctgctgtc acaggttcct ggcgttagtt ttaccgagca ggaagtggct     600
gatctgacca aacgcatcca gaacgcgggt actgaagtgg ttgaagcgaa ggccggtggc     660
gggtctgcaa ccctgtctat gggccaggca gctgcacgtt ttggtctgtc tctggttcgt     720
gcactgcagg gcgaacaagg cgttgtcgaa tgtgcctacg ttgaaggcga cggtcagtac     780 gcccgttct tctctcaacc gctgctgctg gtaaaaacg gcgtggaaga gcgtaaatct     840
atcggtaccc tgagcgcatt tgaacagaac gcgctggaag gtatgctgga tacgctgaag     900
aaagatatcg ccctgggcga agagttcgtt aataagtaa                            939

<210> SEQ ID NO 110
<211> LENGTH: 312
<212> TYPE: PRT
<213> ORGANISM: Escherichia coli

<400> SEQUENCE: 110

Met Lys Val Ala Val Leu Gly Ala Ala Gly Gly Val Gly Gln Ala Leu
1               5                   10                  15

Ala Leu Leu Leu Lys Thr Gln Leu Pro Ser Gly Ser Glu Leu Ser Leu
                20                  25                  30

Tyr Asp Ile Ala Pro Val Thr Pro Gly Val Ala Val Asp Leu Ser His
            35                  40                  45

Ile Pro Thr Ala Val Lys Ile Lys Gly Phe Ser Gly Glu Asp Ala Thr
        50                  55                  60

Pro Ala Leu Glu Gly Ala Asp Val Val Leu Ile Ser Ala Gly Val Ala
65                  70                  75                  80

Ala Lys Pro Gly Glu Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110
```

```
Cys Ile Gly Ile Ile Thr Asn Pro Val Asn Thr Thr Val Ala Ile Ala
            115                 120                 125

Ala Glu Val Leu Lys Lys Ala Gly Val Tyr Asp Lys Asn Lys Leu Phe
        130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Val Val Glu Cys Ala Tyr Val Glu Gly
                245                 250                 255

Asp Gly Gln Tyr Ala Arg Phe Phe Ser Gln Pro Leu Leu Gly Lys
            260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
    290                 295                 300

Leu Gly Glu Glu Phe Val Asn Lys
305                 310

<210> SEQ ID NO 111
<211> LENGTH: 939
<212> TYPE: DNA
<213> ORGANISM: Escherichia coli

<400> SEQUENCE: 111
atgaaagtcg cagtcctcgg cgctgctggg ggtattggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg ttttctggt     180 gaagatgcga ctccggcgct ggaaggcgca gatgtcgttc ttatctctgc aggcgtagcg     240
gctaaacccg ggatggatcg ttccgacctg tttaacgtta acgccggcat cgtgaaaaac     300
ctggtacagc aagttgcgaa acctgcccg aaagcgtgca ttggtattat cactaacccg     360
gttaacacca cagttgcaat tgctgctgaa gtgctgaaaa agccggtgt ttatgacaaa     420 aacaaactgt tcggcgttac cacgctggat atcattcgtt ccaacacctt tgttgcggaa     480
ctgaaaggca acagccagg cgaagttgaa gtgccggtta ttggcggcca ctctgatgtt     540
accattctgc cgctgctgtc acaggttcct ggcgttagtt ttaccgagca ggaagtggct     600
gatctgacca aacgcatcca gaacgcgggt actgaagtgg ttgaagcgaa ggccggtggc     660
gggtctgcaa ccctgtctat gggccaggca gctgcacgtt ttggtctgtc tctggttcgt     720
gcactgcagg gcgaacaagg cgttgtcgaa tgtgcctacg ttgaaggcga cggtcagtac     780
gcccgtttct tctctcaacc gctgctgctg gtaaaaacg cgtggaaga gcgtaaatct     840 atcggtaccc tgagcgcatt tgaacagaac gcgctggaag gtatgctgga tacgctgaag     900
aaagatatcg ccctgggcga agagttcgtt aataagtaa                            939
```

<210> SEQ ID NO 112
<211> LENGTH: 312
<212> TYPE: PRT
<213> ORGANISM: Escherichia coli

<400> SEQUENCE: 112

Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Asp Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
    290                 295                 300

Leu Gly Glu Glu Phe Val Asn Lys
305                 310

<210> SEQ ID NO 113
<211> LENGTH: 939
<212> TYPE: DNA
<213> ORGANISM: Escherichia coli

<400> SEQUENCE: 113
atgaaagtcg cagtcctcgg cgctgctggc ggtattggcc aggcgcttgc actactgtta      60

```
aaaacccaac tgccttcagg ttcagaactc tctctgtatg atatcgctcc agtgactccc      120
ggtgtggctg tcgatctgag ccatatccct actgctgtga aaatcaaagg ttttttctggt     180 gaagatgcga ctccggcgct ggaaggcgca gatgtcgttc ttatctctgc aggcgtagcg      240
gctaaacccg ggatgtctcg ttccgacctg tttaacgtta acgccggcat cgtgaaaaac      300
ctggtacagc aagttgcgaa aacctgcccg aaagcgtgca ttggtattat cactaacccg      360
gttaacacca cagttgcaat tgctgctgaa gtgctgaaaa agccggtgt ttatgacaaa       420 aacaaactgt tcggcgttac cacgctggat atcattcgtt ccaacacctt tgttgcggaa      480
ctgaaaggca acagccagg cgaagttgaa gtgccggtta ttggcggtca ctctggtgtt       540
accattctgc cgctgctgtc acaggttcct ggcgttagtt ttaccgagca ggaagtggct      600
gatctgacca aacgcatcca gaacgcgggt actgaagtgg ttgaagcgaa ggccggtggc     660
gggtctgcaa ccctgtctat gggccaggca gctgcacgtt ttggtctgtc tctggttcgt     720
gcactgcagg gcgaacaagg cgttgtcgaa tgtgcctacg ttgaaggcga cggtcagtac     780
gcccgtttct tctctcaacc gctgctgctg ggtaaaaacg gcgtggaaga gcgtaaatct     840
atcggtaccc tgagcgcatt tgaacagaac gcgctggaag gtatgctgga tacgctgaag     900
aaagatatcg ccctgggcga agagttcgtt aataagtaa                             939
```

<210> SEQ ID NO 114
<211> LENGTH: 312
<212> TYPE: PRT
<213> ORGANISM: Escherichia coli

<400> SEQUENCE: 114

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Met Ser Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Gly Ser Ala Thr
    210                 215                 220
```

Leu Ser Met Gly Gln Ala Ala Arg Phe Gly Leu Ser Leu Val Arg
225                 230                 235                 240

Ala Leu Gln Gly Glu Gln Gly Val Val Glu Cys Ala Tyr Val Glu Gly
            245                 250                 255

Asp Gly Gln Tyr Ala Arg Phe Phe Ser Gln Pro Leu Leu Gly Lys
        260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
        290                 295                 300

Leu Gly Glu Glu Phe Val Asn Lys
305                 310

<210> SEQ ID NO 115
<211> LENGTH: 939
<212> TYPE: DNA
<213> ORGANISM: Escherichia coli

<400> SEQUENCE: 115

```
atgaaagtcg cagtcctcgg cgctgctggc ggtgtcggcc aggcgcttgc actactgtta      60
aaacccaac tgccttcagg ttcagaactc tctctgtatg atatcgctcc agtgactccc      120
ggtgtggctg tcgatctgag ccatatccct actgctgtga aaatcaaagg ttttcctggt     180
gaagatgcga ctccggcgct ggaaggcgca gatgtcgttc ttatctctgc aggcgtagcg     240
gctaaacccg ggatggatcg ttccgacctg tttaacgtta acgccggcat cgtgaaaaac     300
ctggtacagc aagttgcgaa acctgcccg aaagcgtgca ttggtattat cactaacccg      360
gttaacacca cagttgcaat tgctgctgaa gtgctgaaaa agccggtgt ttatgacaaa      420
aacaaactgt tcggcgttac cacgctggat atcattcgtt ccaacacctt tgttgcggaa     480
ctgaaaggca acagccagg cgaagttgaa gtgccggtta ttggcggtca ctctggtgtt     540
accattctgc cgctgctgtc acaggttcct ggcgttagtt taccgagca ggaagtggct      600
gatctgacca aacgcatcca gaacgcgggt actgaagtgg ttgaagcgaa ggccggtggc     660
gggtctgcaa ccctgtctat gggccaggca gctgcacgtt ttggtctgtc tctggttcgt     720
gcactgcagg gcgaacaagg cgttgtcgaa tgtgcctacg ttgaaggcga cggtcagtac     780
gcccgtttct ctctcaacc gctgctgctg gtaaaaacg gcgtgaaga gcgtaaatct        840
atcggtaccc tgagcgcatt tgaacagaac gcgctggaag gtatgctgga tacgctgaag     900
aaagatatcg ccctgggcga agagttcgtt aataagtaa                            939
```

<210> SEQ ID NO 116
<211> LENGTH: 312
<212> TYPE: PRT
<213> ORGANISM: Escherichia coli

<400> SEQUENCE: 116

Met Lys Val Ala Val Leu Gly Ala Ala Gly Gly Val Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

```
Pro Ala Leu Glu Gly Ala Asp Val Val Leu Ile Ser Ala Gly Val Ala
 65                  70                  75                  80

Ala Lys Pro Gly Met Asp Arg Ser Asp Leu Phe Asn Val Asn Ala Gly
                 85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
            115                 120                 125

Ala Glu Val Leu Lys Lys Ala Gly Val Tyr Asp Lys Asn Lys Leu Phe
130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
            275                 280                 285

Gln Asn Ala Leu Glu Gly Met Leu Asp Thr Leu Lys Lys Asp Ile Ala
        290                 295                 300

Leu Gly Glu Glu Phe Val Asn Lys
305                 310

<210> SEQ ID NO 117
<211> LENGTH: 939
<212> TYPE: DNA
<213> ORGANISM: Escherichia coli

<400> SEQUENCE: 117
atgaaagtcg cagtcctcgg cgctgctggg ggtattggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg tttttctggt     180
gaagatgcga ctccggcgct ggaaggcgca gatgtcgttc ttatctctgc aggcgtagcg     240
gctaaacccg gatgtctcg ttccgacctg tttaacgtta acgccggcat cgtgaaaaac     300
ctggtacagc aagttgcgaa acctgcccg aaagcgtgca ttggtattat cactaacccg     360
gttaacacca cagttgcaat tgctgctgaa gtgctgaaaa agccggtgt ttatgacaaa     420 aacaaactgt tcggcgttac cacgctggat atcattcgtt ccaacacctt gttgcggaa      480 ctgaaaggca acagccagg cgaagttgaa gtgccggtta ttggcggcca ctctgatgtt     540
accattctgc cgctgctgtc acaggttcct ggcgttagtt ttaccgagca ggaagtggct     600
gatctgacca acgcatcca gaacgcgggt actgaagtgg ttgaagcgaa ggccggtggc     660
gggtctgcaa ccctgtctat gggccaggca gctgcacgtt ttggtctgtc tctggttcgt     720
```

```
gcactgcagg gcgaacaagg cgttgtcgaa tgtgcctacg ttgaaggcga cggtcagtac      780
gcccgtttct tctctcaacc gctgctgctg ggtaaaaacg gcgtggaaga gcgtaaatct      840
atcggtaccc tgagcgcatt tgaacagaac gcgctggaag gtatgctgga tacgctgaag      900
aaagatatcg ccctgggcga agagttcgtt aataagtaa                             939
```

<210> SEQ ID NO 118
<211> LENGTH: 312
<212> TYPE: PRT
<213> ORGANISM: Escherichia coli

<400> SEQUENCE: 118

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Ala Lys Pro Gly Met Ser Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Asp Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Gly Lys
            260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
    290                 295                 300

Leu Gly Glu Glu Phe Val Asn Lys
305                 310
```

<210> SEQ ID NO 119

```
<211> LENGTH: 36
<212> TYPE: DNA
<213> ORGANISM: Artificial Sequence
<220> FEATURE:
<223> OTHER INFORMATION: Primer for amplification

<400> SEQUENCE: 119
tataatcccg ggatgcgcgt taacaatggt ttgacc                              36

<210> SEQ ID NO 120
<211> LENGTH: 32
<212> TYPE: DNA
<213> ORGANISM: Artificial Sequence
<220> FEATURE:
<223> OTHER INFORMATION: Primer for amplification

<400> SEQUENCE: 120
tataattcta gattacagtt tcggaccagc cg                                  32

<210> SEQ ID NO 121
<211> LENGTH: 36
<212> TYPE: DNA
<213> ORGANISM: Artificial Sequence
<220> FEATURE:
<223> OTHER INFORMATION: Primer for amplification

<400> SEQUENCE: 121
tataatcccg ggatgcgcgt taacaatggt ttgacc                              36

<210> SEQ ID NO 122
<211> LENGTH: 32
<212> TYPE: DNA
<213> ORGANISM: Artificial Sequence
<220> FEATURE:
<223> OTHER INFORMATION: Primer for amplification

<400> SEQUENCE: 122
tataattcta gattacagtt tcggaccagc cg                                  32

<210> SEQ ID NO 123
<211> LENGTH: 30
<212> TYPE: DNA
<213> ORGANISM: Artificial Sequence
<220> FEATURE:
<223> OTHER INFORMATION: Primer for amplification

<400> SEQUENCE: 123
tataatcccg ggatgaacga acaatattcc                                     30

<210> SEQ ID NO 124
<211> LENGTH: 30
<212> TYPE: DNA
<213> ORGANISM: Artificial Sequence
<220> FEATURE:
<223> OTHER INFORMATION: Primer for amplification

<400> SEQUENCE: 124
tataattcta gattagccgg tattacgcat                                     30

<210> SEQ ID NO 125
<211> LENGTH: 36
<212> TYPE: DNA
<213> ORGANISM: Artificial Sequence
<220> FEATURE:
<223> OTHER INFORMATION: Primer for amplification

<400> SEQUENCE: 125
```

```
tataatcccg ggatgaaaac cgtacacaa caaatt                                       36
```

<210> SEQ ID NO 126
<211> LENGTH: 32
<212> TYPE: DNA
<213> ORGANISM: Artificial Sequence
<220> FEATURE:
<223> OTHER INFORMATION: Primer for amplification

<400> SEQUENCE: 126

```
tataattcta gattagaact gcgattcttc ag                                          32
```

<210> SEQ ID NO 127
<211> LENGTH: 36
<212> TYPE: DNA
<213> ORGANISM: Artificial Sequence
<220> FEATURE:
<223> OTHER INFORMATION: Primer for amplification

<400> SEQUENCE: 127

```
tataatcccg ggatgaaaaa actactcgtc gccaat                                      36
```

<210> SEQ ID NO 128
<211> LENGTH: 32
<212> TYPE: DNA
<213> ORGANISM: Artificial Sequence
<220> FEATURE:
<223> OTHER INFORMATION: Primer for amplification

<400> SEQUENCE: 128

```
tataattcta gattaattaa tttcgattaa ca                                          32
```

<210> SEQ ID NO 129
<211> LENGTH: 40
<212> TYPE: DNA
<213> ORGANISM: Artificial Sequence
<220> FEATURE:
<223> OTHER INFORMATION: Primer for amplification

<400> SEQUENCE: 129

```
tataatcccg ggatgcctga cgctaaaaaa cagggggcggt                                 40
```

<210> SEQ ID NO 130
<211> LENGTH: 33
<212> TYPE: DNA
<213> ORGANISM: Artificial Sequence
<220> FEATURE:
<223> OTHER INFORMATION: Primer for amplification

<400> SEQUENCE: 130

```
tataattcta gattaatcgt gagcgcctat ttc                                         33
```

<210> SEQ ID NO 131
<211> LENGTH: 88
<212> TYPE: DNA
<213> ORGANISM: Artificial Sequence
<220> FEATURE:
<223> OTHER INFORMATION: Primer for amplification

<400> SEQUENCE: 131

```
acaatttcac acaggaaaca gaattcgagc tcggtaccgt ttaactttaa gaaggagata           60
taccatgacc acgaagaaag ctgattac                                               88
```

<210> SEQ ID NO 132

<210> SEQ ID NO 132
<211> LENGTH: 78
<212> TYPE: DNA
<213> ORGANISM: Artificial Sequence
<220> FEATURE:
<223> OTHER INFORMATION: Primer for amplification

<400> SEQUENCE: 132

```
ggataacttt tttacgttgt ttatcagcca tggtatatct ccttcttaaa gttaaacgga      60
tccttattga ttaacttg                                                    78
```

<210> SEQ ID NO 133
<211> LENGTH: 69
<212> TYPE: DNA
<213> ORGANISM: Artificial Sequence
<220> FEATURE:
<223> OTHER INFORMATION: Primer for amplification

<400> SEQUENCE: 133

```
taatatggat ccgtttaact ttaagaagga gatataccat ggctgataaa caacgtaaaa      60
aagttatcc                                                              69
```

<210> SEQ ID NO 134
<211> LENGTH: 83
<212> TYPE: DNA
<213> ORGANISM: Artificial Sequence
<220> FEATURE:
<223> OTHER INFORMATION: Primer for amplification

<400> SEQUENCE: 134

```
caatgcggaa tattgttcgt tcatggtata tctccttctt aaagttaaac tctagattag      60
tttttaactg cagaagcaaa ttc                                              83
```

<210> SEQ ID NO 135
<211> LENGTH: 88
<212> TYPE: DNA
<213> ORGANISM: Artificial Sequence
<220> FEATURE:
<223> OTHER INFORMATION: Primer for amplification

<400> SEQUENCE: 135

```
acaatttcac acaggaaaca gaattcgagc tcggtaccgt ttaactttaa gaaggagata      60
taccatgacc acgaagaaag ctgattac                                         88
```

<210> SEQ ID NO 136
<211> LENGTH: 83
<212> TYPE: DNA
<213> ORGANISM: Artificial Sequence
<220> FEATURE:
<223> OTHER INFORMATION: Primer for amplification

<400> SEQUENCE: 136

```
caatgcggaa tattgttcgt tcatggtata tctccttctt aaagttaaac tctagattag      60
tttttaactg cagaagcaaa ttc                                              83
```

<210> SEQ ID NO 137
<211> LENGTH: 56
<212> TYPE: DNA
<213> ORGANISM: Artificial Sequence
<220> FEATURE:
<223> OTHER INFORMATION: Primer for amplification

<400> SEQUENCE: 137

```
gaaggttgcg cctacactaa gcatagttgt tgatgagtgt aggctggagc tgcttc          56
```

<210> SEQ ID NO 138
<211> LENGTH: 56
<212> TYPE: DNA
<213> ORGANISM: Artificial Sequence
<220> FEATURE:
<223> OTHER INFORMATION: Primer for amplification

<400> SEQUENCE: 138
ttaaaccagt tcgttcgggc aggtttcgcc tttttcatgg gaattagcca tggtcc        56

<210> SEQ ID NO 139
<211> LENGTH: 65
<212> TYPE: DNA
<213> ORGANISM: Artificial Sequence
<220> FEATURE:
<223> OTHER INFORMATION: Primer for amplification

<400> SEQUENCE: 139
atggctgtta ctaatgtcgc tgaacttaac gcactcgtag agcgtgtgta ggctggagct        60
gcttc        65

<210> SEQ ID NO 140
<211> LENGTH: 65
<212> TYPE: DNA
<213> ORGANISM: Artificial Sequence
<220> FEATURE:
<223> OTHER INFORMATION: Primer for amplification

<400> SEQUENCE: 140
ttaagcggat tttttcgctt ttttctcagc tttagccgga gcagccatat gaatatcctc        60
cttag        65

<210> SEQ ID NO 141
<211> LENGTH: 65
<212> TYPE: DNA
<213> ORGANISM: Artificial Sequence
<220> FEATURE:
<223> OTHER INFORMATION: Primer for amplification

<400> SEQUENCE: 141
atgtcgagta agttagtact ggttctgaac tgcggtagtt cttcagtgta ggctggagct        60
gcttc        65

<210> SEQ ID NO 142
<211> LENGTH: 65
<212> TYPE: DNA
<213> ORGANISM: Artificial Sequence
<220> FEATURE:
<223> OTHER INFORMATION: Primer for amplification

<400> SEQUENCE: 142
tcaggcagtc aggcggctcg cgtcttgcgc gataaccagt tcttccatat gaatatcctc        60
cttag        65

<210> SEQ ID NO 143
<211> LENGTH: 65
<212> TYPE: DNA
<213> ORGANISM: Artificial Sequence
<220> FEATURE:
<223> OTHER INFORMATION: Primer for amplification

<400> SEQUENCE: 143

```
ttactccgta tttgcataaa aaccatgcga gttacgggcc tataagtgta ggctggagct    60
gcttc                                                                65

<210> SEQ ID NO 144
<211> LENGTH: 65
<212> TYPE: DNA
<213> ORGANISM: Artificial Sequence
<220> FEATURE:
<223> OTHER INFORMATION: Primer for amplification

<400> SEQUENCE: 144
atagattgag tgaaggtacg agtaataacg tcctgctgct gttctcatat gaatatcctc    60
cttag                                                                65

<210> SEQ ID NO 145
<211> LENGTH: 65
<212> TYPE: DNA
<213> ORGANISM: Artificial Sequence
<220> FEATURE:
<223> OTHER INFORMATION: Primer for amplification

<400> SEQUENCE: 145
gtgtcccgta ttattatgct gatccctacc ggaaccagcg tcggtgtgta ggctggagct    60
gcttc                                                                65

<210> SEQ ID NO 146
<211> LENGTH: 65
<212> TYPE: DNA
<213> ORGANISM: Artificial Sequence
<220> FEATURE:
<223> OTHER INFORMATION: Primer for amplification

<400> SEQUENCE: 146
ttactgctgc tgtgcagact gaatcgcagt cagcgcgatg gtgtacatat gaatatcctc    60
cttag                                                                65

<210> SEQ ID NO 147
<211> LENGTH: 65
<212> TYPE: DNA
<213> ORGANISM: Artificial Sequence
<220> FEATURE:
<223> OTHER INFORMATION: Primer for amplification

<400> SEQUENCE: 147
atgaaacaaa cggttgcagc ttatatcgcc aaaacactcg aatcggtgta ggctggagct    60
gcttc                                                                65

<210> SEQ ID NO 148
<211> LENGTH: 65
<212> TYPE: DNA
<213> ORGANISM: Artificial Sequence
<220> FEATURE:
<223> OTHER INFORMATION: Primer for amplification

<400> SEQUENCE: 148
ttaccttagc cagtttgttt tcgccagttc gatcacttca tcacccatat gaatatcctc    60
cttag                                                                65

<210> SEQ ID NO 149
<211> LENGTH: 65
<212> TYPE: DNA
<213> ORGANISM: Artificial Sequence
```

<220> FEATURE:
<223> OTHER INFORMATION: Primer for amplification

<400> SEQUENCE: 149
atgaccatta ctccggcaac tcatgcaatt tcgataaatc ctgccgtgta ggctggagct    60
gcttc                                                                65

<210> SEQ ID NO 150
<211> LENGTH: 65
<212> TYPE: DNA
<213> ORGANISM: Artificial Sequence
<220> FEATURE:
<223> OTHER INFORMATION: Primer for amplification

<400> SEQUENCE: 150
tcagatccgg tctttccaca ccgtctggat attacagaat tcgtgcatat gaatatcctc    60
cttag                                                                65

<210> SEQ ID NO 151
<211> LENGTH: 65
<212> TYPE: DNA
<213> ORGANISM: Artificial Sequence
<220> FEATURE:
<223> OTHER INFORMATION: Primer for amplification

<400> SEQUENCE: 151
atgaaactta acgacagtaa cttattccgc cagcaggcgt tgattgtgta ggctggagct    60
gcttc                                                                65

<210> SEQ ID NO 152
<211> LENGTH: 65
<212> TYPE: DNA
<213> ORGANISM: Artificial Sequence
<220> FEATURE:
<223> OTHER INFORMATION: Primer for amplification

<400> SEQUENCE: 152
ttaaagaccg atgcacatat atttgatttc taagtaatct tcgatcatat gaatatcctc    60
cttag                                                                65

<210> SEQ ID NO 153
<211> LENGTH: 65
<212> TYPE: DNA
<213> ORGANISM: Artificial Sequence
<220> FEATURE:
<223> OTHER INFORMATION: Primer for amplification

<400> SEQUENCE: 153
atggaccaga agctgttaac ggatttccgc tcagaactac tcgatgtgta ggctggagct    60
gcttc                                                                65

<210> SEQ ID NO 154
<211> LENGTH: 65
<212> TYPE: DNA
<213> ORGANISM: Artificial Sequence
<220> FEATURE:
<223> OTHER INFORMATION: Primer for amplification

<400> SEQUENCE: 154
tcaggtgtgt ttaaagctgt tctgctgggc aataccctgc agtttcatat gaatatcctc    60
cttag                                                                65

<210> SEQ ID NO 155
<211> LENGTH: 65
<212> TYPE: DNA
<213> ORGANISM: Artificial Sequence
<220> FEATURE:
<223> OTHER INFORMATION: Primer for amplification

<400> SEQUENCE: 155
atggataaga agcaagtaac ggatttaagg tcggaactac tcgatgtgta ggctggagct    60
gcttc    65

<210> SEQ ID NO 156
<211> LENGTH: 65
<212> TYPE: DNA
<213> ORGANISM: Artificial Sequence
<220> FEATURE:
<223> OTHER INFORMATION: Primer for amplification

<400> SEQUENCE: 156
tcaggtatgt ttaaagctgt tctgttgggc aataccctgc agtttcatat gaatatcctc    60
cttag    65

<210> SEQ ID NO 157
<211> LENGTH: 65
<212> TYPE: DNA
<213> ORGANISM: Artificial Sequence
<220> FEATURE:
<223> OTHER INFORMATION: Primer for amplification

<400> SEQUENCE: 157
atggctacat cagtacagac aggtaaagct aagcagctca cattagtgta ggctggagct    60
gcttc    65

<210> SEQ ID NO 158
<211> LENGTH: 65
<212> TYPE: DNA
<213> ORGANISM: Artificial Sequence
<220> FEATURE:
<223> OTHER INFORMATION: Primer for amplification

<400> SEQUENCE: 158
ttagtgtttc ttgtcattca tcacaatata gtgtggtgaa cgtgccatat gaatatcctc    60
cttag    65

<210> SEQ ID NO 159
<211> LENGTH: 65
<212> TYPE: DNA
<213> ORGANISM: Artificial Sequence
<220> FEATURE:
<223> OTHER INFORMATION: Primer for amplification

<400> SEQUENCE: 159
atggaaccaa aaacaaaaaa acagcgttcg ctttatatcc cttacgtgta ggctggagct    60
gcttc    65

<210> SEQ ID NO 160
<211> LENGTH: 65
<212> TYPE: DNA
<213> ORGANISM: Artificial Sequence
<220> FEATURE:
<223> OTHER INFORMATION: Primer for amplification

<400> SEQUENCE: 160

```
ttagatggag gtacggcggt agtcgcggta ttcggcttgc cagaacatat gaatatcctc    60
cttag                                                                 65
```

<210> SEQ ID NO 161
<211> LENGTH: 65
<212> TYPE: DNA
<213> ORGANISM: Artificial Sequence
<220> FEATURE:
<223> OTHER INFORMATION: Primer for amplification

<400> SEQUENCE: 161

```
atggatgacc agttaaaaca aagtgcactt gatttccatg aatttgtgta ggctggagct    60
gcttc                                                                 65
```

<210> SEQ ID NO 162
<211> LENGTH: 65
<212> TYPE: DNA
<213> ORGANISM: Artificial Sequence
<220> FEATURE:
<223> OTHER INFORMATION: Primer for amplification

<400> SEQUENCE: 162

```
ttacagcggt tgggtttgcg cttctaccac ggccagcgcc accatcatat gaatatcctc    60
cttag                                                                 65
```

<210> SEQ ID NO 163
<211> LENGTH: 65
<212> TYPE: DNA
<213> ORGANISM: Artificial Sequence
<220> FEATURE:
<223> OTHER INFORMATION: Primer for amplification

<400> SEQUENCE: 163

```
atgaacgaac aatattccgc attgcgtagt aatgtcagta tgctcgtgta ggctggagct    60
gcttc                                                                 65
```

<210> SEQ ID NO 164
<211> LENGTH: 65
<212> TYPE: DNA
<213> ORGANISM: Artificial Sequence
<220> FEATURE:
<223> OTHER INFORMATION: Primer for amplification

<400> SEQUENCE: 164

```
ttagccggta ttacgcatac ctgccgcaat cccggcaata gtgaccatat gaatatcctc    60
cttag                                                                 65
```

<210> SEQ ID NO 165
<211> LENGTH: 65
<212> TYPE: DNA
<213> ORGANISM: Artificial Sequence
<220> FEATURE:
<223> OTHER INFORMATION: Primer for amplification

<400> SEQUENCE: 165

```
atgtccagaa ggcttcgcag aacaaaaatc gttaccacgt taggcgtgta ggctggagct    60
gcttc                                                                 65
```

<210> SEQ ID NO 166
<211> LENGTH: 65
<212> TYPE: DNA

```
<213> ORGANISM: Artificial Sequence
<220> FEATURE:
<223> OTHER INFORMATION: Primer for amplification

<400> SEQUENCE: 166
ttactctacc gttaaaatac gcgtggtatt agtagaaccc acggtcatat gaatatcctc    60
cttag                                                                65

<210> SEQ ID NO 167
<211> LENGTH: 65
<212> TYPE: DNA
<213> ORGANISM: Artificial Sequence
<220> FEATURE:
<223> OTHER INFORMATION: Primer for amplification

<400> SEQUENCE: 167
atgaaaaaga ccaaaattgt ttgcaccatc ggaccgaaaa ccgaagtgta ggctggagct    60
gcttc                                                                65

<210> SEQ ID NO 168
<211> LENGTH: 65
<212> TYPE: DNA
<213> ORGANISM: Artificial Sequence
<220> FEATURE:
<223> OTHER INFORMATION: Primer for amplification

<400> SEQUENCE: 168
ttacaggacg tgaacagatg cggtgttagt agtgccgctc ggtaccatat gaatatcctc    60
cttag                                                                65

<210> SEQ ID NO 169
<211> LENGTH: 65
<212> TYPE: DNA
<213> ORGANISM: Artificial Sequence
<220> FEATURE:
<223> OTHER INFORMATION: Primer for amplification

<400> SEQUENCE: 169
atggaactga cgactcgcac tttacctgcg cggaaacata ttgcggtgta ggctggagct    60
gcttc                                                                65

<210> SEQ ID NO 170
<211> LENGTH: 65
<212> TYPE: DNA
<213> ORGANISM: Artificial Sequence
<220> FEATURE:
<223> OTHER INFORMATION: Primer for amplification

<400> SEQUENCE: 170
ttacttcaga cggtccgcga gataacgctg ataatcgggg atcagcatat gaatatcctc    60
cttag                                                                65

<210> SEQ ID NO 171
<211> LENGTH: 65
<212> TYPE: DNA
<213> ORGANISM: Artificial Sequence
<220> FEATURE:
<223> OTHER INFORMATION: Primer for amplification

<400> SEQUENCE: 171
atggtcgcac ccattcccgc gaaacgcggc agaaacccg ccgttgtgta ggctggagct     60
gcttc                                                                65
```

<210> SEQ ID NO 172
<211> LENGTH: 65
<212> TYPE: DNA
<213> ORGANISM: Artificial Sequence
<220> FEATURE:
<223> OTHER INFORMATION: Primer for amplification

<400> SEQUENCE: 172
tcagcgcatt ccaccgtacg ccagcgtcac ttccttcgcc gctttcatat gaatatcctc    60
cttag                                                               65

<210> SEQ ID NO 173
<211> LENGTH: 65
<212> TYPE: DNA
<213> ORGANISM: Artificial Sequence
<220> FEATURE:
<223> OTHER INFORMATION: Primer for amplification

<400> SEQUENCE: 173
atggaaagta aagtagttgt tccggcacaa ggcaagaaga tcaccgtgta ggctggagct    60
gcttc                                                               65

<210> SEQ ID NO 174
<211> LENGTH: 65
<212> TYPE: DNA
<213> ORGANISM: Artificial Sequence
<220> FEATURE:
<223> OTHER INFORMATION: Primer for amplification

<400> SEQUENCE: 174
ttacatgttt tcgatgatcg cgtcaccaaa ctctgaacat ttcagcatat gaatatcctc    60
cttag                                                               65

<210> SEQ ID NO 175
<211> LENGTH: 65
<212> TYPE: DNA
<213> ORGANISM: Artificial Sequence
<220> FEATURE:
<223> OTHER INFORMATION: Primer for amplification

<400> SEQUENCE: 175
atgcagaaca gcgctttgaa agcctggttg gactcttctt acctcgtgta ggctggagct    60
gcttc                                                               65

<210> SEQ ID NO 176
<211> LENGTH: 65
<212> TYPE: DNA
<213> ORGANISM: Artificial Sequence
<220> FEATURE:
<223> OTHER INFORMATION: Primer for amplification

<400> SEQUENCE: 176
ttattcgacg ttcagcgcgt cattaaccag atcttgttgc tgtttcatat gaatatcctc    60
cttag                                                               65

<210> SEQ ID NO 177
<211> LENGTH: 65
<212> TYPE: DNA
<213> ORGANISM: Artificial Sequence
<220> FEATURE:
<223> OTHER INFORMATION: Primer for amplification

<400> SEQUENCE: 177
atgagtagcg tagatattct ggtccctgac ctgcctgaat ccgtagtgta ggctggagct    60
gcttc    65

<210> SEQ ID NO 178
<211> LENGTH: 65
<212> TYPE: DNA
<213> ORGANISM: Artificial Sequence
<220> FEATURE:
<223> OTHER INFORMATION: Primer for amplification

<400> SEQUENCE: 178
ctacacgtcc agcagcagac gcgtcggatc ttccagcaac tctttcatat gaatatcctc    60
cttag    65

<210> SEQ ID NO 179
<211> LENGTH: 65
<212> TYPE: DNA
<213> ORGANISM: Artificial Sequence
<220> FEATURE:
<223> OTHER INFORMATION: Primer for amplification

<400> SEQUENCE: 179
gtgcaaacct ttcaagccga tcttgccatt gtaggcgccg gtggcgtgta ggctggagct    60
gcttc    65

<210> SEQ ID NO 180
<211> LENGTH: 65
<212> TYPE: DNA
<213> ORGANISM: Artificial Sequence
<220> FEATURE:
<223> OTHER INFORMATION: Primer for amplification

<400> SEQUENCE: 180
tcagccattc gccttctcct tcttattggc tgcttccgcc ttatccatat gaatatcctc    60
cttag    65

<210> SEQ ID NO 181
<211> LENGTH: 65
<212> TYPE: DNA
<213> ORGANISM: Artificial Sequence
<220> FEATURE:
<223> OTHER INFORMATION: Primer for amplification

<400> SEQUENCE: 181
atggctgaga tgaaaaacct gaaaattgag gtggtgcgct ataacgtgta ggctggagct    60
gcttc    65

<210> SEQ ID NO 182
<211> LENGTH: 65
<212> TYPE: DNA
<213> ORGANISM: Artificial Sequence
<220> FEATURE:
<223> OTHER INFORMATION: Primer for amplification

<400> SEQUENCE: 182
ttagcgtggt ttcagggtcg cgataagaaa gtctttcgaa ctttccatat gaatatcctc    60
cttag    65

<210> SEQ ID NO 183
<211> LENGTH: 65

```
<212> TYPE: DNA
<213> ORGANISM: Artificial Sequence
<220> FEATURE:
<223> OTHER INFORMATION: Primer for amplification

<400> SEQUENCE: 183
atgacgacta aacgtaaacc gtatgtacgg ccaatgacgt ccaccgtgta ggctggagct    60
gcttc                                                                65

<210> SEQ ID NO 184
<211> LENGTH: 65
<212> TYPE: DNA
<213> ORGANISM: Artificial Sequence
<220> FEATURE:
<223> OTHER INFORMATION: Primer for amplification

<400> SEQUENCE: 184
ttaccagtac agggcaacaa acaggattac gatggtggca accaccatat gaatatcctc    60
cttag                                                                65

<210> SEQ ID NO 185
<211> LENGTH: 65
<212> TYPE: DNA
<213> ORGANISM: Artificial Sequence
<220> FEATURE:
<223> OTHER INFORMATION: Primer for amplification

<400> SEQUENCE: 185
atgattaatc caaatccaaa gcgttctgac gaaccggtat tctgggtgta ggctggagct    60
gcttc                                                                65

<210> SEQ ID NO 186
<211> LENGTH: 65
<212> TYPE: DNA
<213> ORGANISM: Artificial Sequence
<220> FEATURE:
<223> OTHER INFORMATION: Primer for amplification

<400> SEQUENCE: 186
ttagattgta acgacaccaa tcagcgtgac aactgtcagg atagccatat gaatatcctc    60
cttag                                                                65

<210> SEQ ID NO 187
<211> LENGTH: 65
<212> TYPE: DNA
<213> ORGANISM: Artificial Sequence
<220> FEATURE:
<223> OTHER INFORMATION: Primer for amplification

<400> SEQUENCE: 187
atgatttcag gcattttagc atccccgggt atcgctttcg gtaaagtgta ggctggagct    60
gcttc                                                                65

<210> SEQ ID NO 188
<211> LENGTH: 65
<212> TYPE: DNA
<213> ORGANISM: Artificial Sequence
<220> FEATURE:
<223> OTHER INFORMATION: Primer for amplification

<400> SEQUENCE: 188
ttagcagatt gttttttctt caatgaactt gttaaccagc gtcatcatat gaatatcctc    60
``` cttag                                                              65

<210> SEQ ID NO 189
<211> LENGTH: 65
<212> TYPE: DNA
<213> ORGANISM: Artificial Sequence
<220> FEATURE:
<223> OTHER INFORMATION: Primer for amplification

<400> SEQUENCE: 189
atgtttaaga atgcatttgc taacctgcaa aaggtcggta aatcggtgta ggctggagct    60
gcttc                                                              65

<210> SEQ ID NO 190
<211> LENGTH: 65
<212> TYPE: DNA
<213> ORGANISM: Artificial Sequence
<220> FEATURE:
<223> OTHER INFORMATION: Primer for amplification

<400> SEQUENCE: 190
ttagtggtta cggatgtact catccatctc ggttttcagg ttatccatat gaatatcctc    60
cttag                                                              65

<210> SEQ ID NO 191
<211> LENGTH: 65
<212> TYPE: DNA
<213> ORGANISM: Artificial Sequence
<220> FEATURE:
<223> OTHER INFORMATION: Primer for amplification

<400> SEQUENCE: 191
gtgaaaccag taacgttata cgatgtcgca gagtatgccg gtgtcgtgta ggctggagct    60
gcttc                                                              65

<210> SEQ ID NO 192
<211> LENGTH: 65
<212> TYPE: DNA
<213> ORGANISM: Artificial Sequence
<220> FEATURE:
<223> OTHER INFORMATION: Primer for amplification

<400> SEQUENCE: 192
tcactgcccg ctttccagtc gggaaacctg tcgtgccagc tgcatcatat gaatatcctc    60
cttag                                                              65

<210> SEQ ID NO 193
<211> LENGTH: 65
<212> TYPE: DNA
<213> ORGANISM: Artificial Sequence
<220> FEATURE:
<223> OTHER INFORMATION: Primer for amplification

<400> SEQUENCE: 193
atgattattt ccgcagccag cgattatcgc gccgcagcgc aacgcgtgta ggctggagct    60
gcttc                                                              65

<210> SEQ ID NO 194
<211> LENGTH: 65
<212> TYPE: DNA
<213> ORGANISM: Artificial Sequence
<220> FEATURE:
<223> OTHER INFORMATION: Primer for amplification -continued

<400> SEQUENCE: 194
ctatgccgca ttcccttcg ccatgggagc cagtgccgca ggcaacatat gaatatcctc     60
cttag                                                                65

<210> SEQ ID NO 195
<211> LENGTH: 65
<212> TYPE: DNA
<213> ORGANISM: Artificial Sequence
<220> FEATURE:
<223> OTHER INFORMATION: Primer for amplification

<400> SEQUENCE: 195
atgaaaaaca tcaatccaac gcagaccgct gcctggcagg cactagtgta ggctggagct     60
gcttc                                                                65

<210> SEQ ID NO 196
<211> LENGTH: 65
<212> TYPE: DNA
<213> ORGANISM: Artificial Sequence
<220> FEATURE:
<223> OTHER INFORMATION: Primer for amplification

<400> SEQUENCE: 196
ttaaccgcgc cacgctttat agcggttaat cagaccattg gtcgacatat gaatatcctc     60
cttag                                                                65

<210> SEQ ID NO 197
<211> LENGTH: 65
<212> TYPE: DNA
<213> ORGANISM: Artificial Sequence
<220> FEATURE:
<223> OTHER INFORMATION: Primer for amplification

<400> SEQUENCE: 197
atgccgattc gtgtgccgga cgagctaccc gccgtcaatt tcttggtgta ggctggagct     60
gcttc                                                                65

<210> SEQ ID NO 198
<211> LENGTH: 65
<212> TYPE: DNA
<213> ORGANISM: Artificial Sequence
<220> FEATURE:
<223> OTHER INFORMATION: Primer for amplification

<400> SEQUENCE: 198
ttaatccagc gttggattca tgtgccgtag atcgtatggc gtgatcatat gaatatcctc     60
cttag                                                                65

<210> SEQ ID NO 199
<211> LENGTH: 65
<212> TYPE: DNA
<213> ORGANISM: Artificial Sequence
<220> FEATURE:
<223> OTHER INFORMATION: Primer for amplification

<400> SEQUENCE: 199
atggttaaag tttatgcccc ggcttccagt gccaatatga gcgtcgtgta ggctggagct     60
gcttc                                                                65

<210> SEQ ID NO 200

```
<211> LENGTH: 65
<212> TYPE: DNA
<213> ORGANISM: Artificial Sequence
<220> FEATURE:
<223> OTHER INFORMATION: Primer for amplification

<400> SEQUENCE: 200 ttagtttttcc agtactcgtg cgcccgccgt atccagccgg caaatcatat gaatatcctc    60
cttag                                                                 65

<210> SEQ ID NO 201
<211> LENGTH: 65
<212> TYPE: DNA
<213> ORGANISM: Artificial Sequence
<220> FEATURE:
<223> OTHER INFORMATION: Primer for amplification

<400> SEQUENCE: 201
atgccacatt cactgttcag caccgatacc gatctcaccg ccgaagtgta ggctggagct    60
gcttc                                                                 65

<210> SEQ ID NO 202
<211> LENGTH: 65
<212> TYPE: DNA
<213> ORGANISM: Artificial Sequence
<220> FEATURE:
<223> OTHER INFORMATION: Primer for amplification

<400> SEQUENCE: 202
ttaaagcaat tccagcgcca gtaattcttc gatggtctgg cgacgcatat gaatatcctc    60
cttag                                                                 65

<210> SEQ ID NO 203
<211> LENGTH: 65
<212> TYPE: DNA
<213> ORGANISM: Artificial Sequence
<220> FEATURE:
<223> OTHER INFORMATION: Primer for amplification

<400> SEQUENCE: 203
atgaaaaact ggaaaacaag tgcagaatca atcctgacca ccggcgtgta ggctggagct    60
gcttc                                                                 65

<210> SEQ ID NO 204
<211> LENGTH: 65
<212> TYPE: DNA
<213> ORGANISM: Artificial Sequence
<220> FEATURE:
<223> OTHER INFORMATION: Primer for amplification

<400> SEQUENCE: 204
ctcgatcggg cattttgact tttacagctt agcgccttct acagccatat gaatatcctc    60
cttag                                                                 65

<210> SEQ ID NO 205
<211> LENGTH: 65
<212> TYPE: DNA
<213> ORGANISM: Artificial Sequence
<220> FEATURE:
<223> OTHER INFORMATION: Primer for amplification

<400> SEQUENCE: 205
atggctatcg acgaaaacaa acagaaagcg ttggcggcag cactggtgta ggctggagct    60
``` gcttc                                                              65

<210> SEQ ID NO 206
<211> LENGTH: 65
<212> TYPE: DNA
<213> ORGANISM: Artificial Sequence
<220> FEATURE:
<223> OTHER INFORMATION: Primer for amplification

<400> SEQUENCE: 206
ttaaaaatct tcgttagttt ctgctacgcc ttcgctatca tctaccatat gaatatcctc    60
cttag                                                              65

<210> SEQ ID NO 207
<211> LENGTH: 65
<212> TYPE: DNA
<213> ORGANISM: Artificial Sequence
<220> FEATURE:
<223> OTHER INFORMATION: Primer for amplification

<400> SEQUENCE: 207
atgaaaaatg ttggttttat cggctggcgc ggtatggtcg gctccgtgta ggctggagct    60
gcttc                                                              65

<210> SEQ ID NO 208
<211> LENGTH: 65
<212> TYPE: DNA
<213> ORGANISM: Artificial Sequence
<220> FEATURE:
<223> OTHER INFORMATION: Primer for amplification

<400> SEQUENCE: 208
ttacgccagt tgacgaagca tccgacgcag cggctccgcg gcccccatat gaatatcctc    60
cttag                                                              65

<210> SEQ ID NO 209
<211> LENGTH: 20
<212> TYPE: DNA
<213> ORGANISM: Artificial Sequence
<220> FEATURE:
<223> OTHER INFORMATION: Primer for amplification

<400> SEQUENCE: 209
cggtgccctg aatgaactgc                                              20

<210> SEQ ID NO 210
<211> LENGTH: 20
<212> TYPE: DNA
<213> ORGANISM: Artificial Sequence
<220> FEATURE:
<223> OTHER INFORMATION: Primer for amplification

<400> SEQUENCE: 210
cagtcatagc cgaatagcct                                              20

<210> SEQ ID NO 211
<211> LENGTH: 20
<212> TYPE: DNA
<213> ORGANISM: Artificial Sequence
<220> FEATURE:
<223> OTHER INFORMATION: Primer for amplification

<400> SEQUENCE: 211

-continued atacgtgtcc cgagcggtag                    20

<210> SEQ ID NO 212
<211> LENGTH: 20
<212> TYPE: DNA
<213> ORGANISM: Artificial Sequence
<220> FEATURE:
<223> OTHER INFORMATION: Primer for amplification

<400> SEQUENCE: 212
tacacatccc gccatcagca                    20

<210> SEQ ID NO 213
<211> LENGTH: 20
<212> TYPE: DNA
<213> ORGANISM: Artificial Sequence
<220> FEATURE:
<223> OTHER INFORMATION: Primer for amplification

<400> SEQUENCE: 213
gaagtaaacg ggaaaatcaa                    20

<210> SEQ ID NO 214
<211> LENGTH: 20
<212> TYPE: DNA
<213> ORGANISM: Artificial Sequence
<220> FEATURE:
<223> OTHER INFORMATION: Primer for amplification

<400> SEQUENCE: 214
agaagtggca taagaaaacg                    20

<210> SEQ ID NO 215
<211> LENGTH: 20
<212> TYPE: DNA
<213> ORGANISM: Artificial Sequence
<220> FEATURE:
<223> OTHER INFORMATION: Primer for amplification

<400> SEQUENCE: 215
ccattggctg aaaattacgc                    20

<210> SEQ ID NO 216
<211> LENGTH: 20
<212> TYPE: DNA
<213> ORGANISM: Artificial Sequence
<220> FEATURE:
<223> OTHER INFORMATION: Primer for amplification

<400> SEQUENCE: 216
gttccattgc acggatcacg                    20

<210> SEQ ID NO 217
<211> LENGTH: 20
<212> TYPE: DNA
<213> ORGANISM: Artificial Sequence
<220> FEATURE:
<223> OTHER INFORMATION: Primer for amplification

<400> SEQUENCE: 217
atgccgtaga agccgccagt                    20

<210> SEQ ID NO 218
<211> LENGTH: 20
<212> TYPE: DNA
<213> ORGANISM: Artificial Sequence
<220> FEATURE:
<223> OTHER INFORMATION: Primer for amplification

<400> SEQUENCE: 218
tgttggtgcg cagctcgaag                                               20

<210> SEQ ID NO 219
<211> LENGTH: 20
<212> TYPE: DNA
<213> ORGANISM: Artificial Sequence
<220> FEATURE:
<223> OTHER INFORMATION: Primer for amplification

<400> SEQUENCE: 219
gcaaatctgg tttcatcaac                                               20

<210> SEQ ID NO 220
<211> LENGTH: 20
<212> TYPE: DNA
<213> ORGANISM: Artificial Sequence
<220> FEATURE:
<223> OTHER INFORMATION: Primer for amplification

<400> SEQUENCE: 220
tcccttgcac aaaacaaagt                                               20

<210> SEQ ID NO 221
<211> LENGTH: 20
<212> TYPE: DNA
<213> ORGANISM: Artificial Sequence
<220> FEATURE:
<223> OTHER INFORMATION: Primer for amplification

<400> SEQUENCE: 221
ggatttggtt ctcgcataat                                               20

<210> SEQ ID NO 222
<211> LENGTH: 20
<212> TYPE: DNA
<213> ORGANISM: Artificial Sequence
<220> FEATURE:
<223> OTHER INFORMATION: Primer for amplification

<400> SEQUENCE: 222
agcattaacg gtagggtcgt                                               20

<210> SEQ ID NO 223
<211> LENGTH: 20
<212> TYPE: DNA
<213> ORGANISM: Artificial Sequence
<220> FEATURE:
<223> OTHER INFORMATION: Primer for amplification

<400> SEQUENCE: 223
gctgattctc gcgaataaac                                               20

<210> SEQ ID NO 224
<211> LENGTH: 20
<212> TYPE: DNA
<213> ORGANISM: Artificial Sequence
<220> FEATURE:
<223> OTHER INFORMATION: Primer for amplification

<400> SEQUENCE: 224
aaaaacgttc ttgcgcgtct                                               20

```
<210> SEQ ID NO 225
<211> LENGTH: 20
<212> TYPE: DNA
<213> ORGANISM: Artificial Sequence
<220> FEATURE:
<223> OTHER INFORMATION: Primer for amplification

<400> SEQUENCE: 225
tctgtttgtc accacccgc                                                    20

<210> SEQ ID NO 226
<211> LENGTH: 20
<212> TYPE: DNA
<213> ORGANISM: Artificial Sequence
<220> FEATURE:
<223> OTHER INFORMATION: Primer for amplification

<400> SEQUENCE: 226
aagccagcac ctggaagcag                                                   20

<210> SEQ ID NO 227
<211> LENGTH: 20
<212> TYPE: DNA
<213> ORGANISM: Artificial Sequence
<220> FEATURE:
<223> OTHER INFORMATION: Primer for amplification

<400> SEQUENCE: 227
aagagctgcc gcaggaggat                                                   20

<210> SEQ ID NO 228
<211> LENGTH: 20
<212> TYPE: DNA
<213> ORGANISM: Artificial Sequence
<220> FEATURE:
<223> OTHER INFORMATION: Primer for amplification

<400> SEQUENCE: 228
gccgccctct taagtcaaat                                                   20

<210> SEQ ID NO 229
<211> LENGTH: 20
<212> TYPE: DNA
<213> ORGANISM: Artificial Sequence
<220> FEATURE:
<223> OTHER INFORMATION: Primer for amplification

<400> SEQUENCE: 229
ggattttagc aatattcgct                                                   20

<210> SEQ ID NO 230
<211> LENGTH: 20
<212> TYPE: DNA
<213> ORGANISM: Artificial Sequence
<220> FEATURE:
<223> OTHER INFORMATION: Primer for amplification

<400> SEQUENCE: 230
cctaatagca ggaagaagac                                                   20

<210> SEQ ID NO 231
<211> LENGTH: 20
<212> TYPE: DNA
<213> ORGANISM: Artificial Sequence
<220> FEATURE:
<223> OTHER INFORMATION: Primer for amplification
```

<400> SEQUENCE: 231
gctgaactgt tgctggaaga                                            20

<210> SEQ ID NO 232
<211> LENGTH: 20
<212> TYPE: DNA
<213> ORGANISM: Artificial Sequence
<220> FEATURE:
<223> OTHER INFORMATION: Primer for amplification

<400> SEQUENCE: 232
ggcgtgcttt tacaactaca                                            20

<210> SEQ ID NO 233
<211> LENGTH: 20
<212> TYPE: DNA
<213> ORGANISM: Artificial Sequence
<220> FEATURE:
<223> OTHER INFORMATION: Primer for amplification

<400> SEQUENCE: 233
tagtaaataa cccaaccggc                                            20

<210> SEQ ID NO 234
<211> LENGTH: 20
<212> TYPE: DNA
<213> ORGANISM: Artificial Sequence
<220> FEATURE:
<223> OTHER INFORMATION: Primer for amplification

<400> SEQUENCE: 234
tcagtgagcg cagtgtttta                                            20

<210> SEQ ID NO 235
<211> LENGTH: 20
<212> TYPE: DNA
<213> ORGANISM: Artificial Sequence
<220> FEATURE:
<223> OTHER INFORMATION: Primer for amplification

<400> SEQUENCE: 235
attaatggtg agagtttgga                                            20

<210> SEQ ID NO 236
<211> LENGTH: 20
<212> TYPE: DNA
<213> ORGANISM: Artificial Sequence
<220> FEATURE:
<223> OTHER INFORMATION: Primer for amplification

<400> SEQUENCE: 236
tgcttttttt tattattcgc                                            20

<210> SEQ ID NO 237
<211> LENGTH: 20
<212> TYPE: DNA
<213> ORGANISM: Artificial Sequence
<220> FEATURE:
<223> OTHER INFORMATION: Primer for amplification

<400> SEQUENCE: 237
gctttataaa agacgacgaa                                            20

<210> SEQ ID NO 238

```
<211> LENGTH: 20
<212> TYPE: DNA
<213> ORGANISM: Artificial Sequence
<220> FEATURE:
<223> OTHER INFORMATION: Primer for amplification

<400> SEQUENCE: 238
gtaacgacaa ttccttaagg                                              20

<210> SEQ ID NO 239
<211> LENGTH: 20
<212> TYPE: DNA
<213> ORGANISM: Artificial Sequence
<220> FEATURE:
<223> OTHER INFORMATION: Primer for amplification

<400> SEQUENCE: 239
tttatatgcc catggtttct                                              20

<210> SEQ ID NO 240
<211> LENGTH: 20
<212> TYPE: DNA
<213> ORGANISM: Artificial Sequence
<220> FEATURE:
<223> OTHER INFORMATION: Primer for amplification

<400> SEQUENCE: 240
atctgttaga ggcggatgat                                              20

<210> SEQ ID NO 241
<211> LENGTH: 20
<212> TYPE: DNA
<213> ORGANISM: Artificial Sequence
<220> FEATURE:
<223> OTHER INFORMATION: Primer for amplification

<400> SEQUENCE: 241
ctggaacgtt aaatctttga                                              20

<210> SEQ ID NO 242
<211> LENGTH: 20
<212> TYPE: DNA
<213> ORGANISM: Artificial Sequence
<220> FEATURE:
<223> OTHER INFORMATION: Primer for amplification

<400> SEQUENCE: 242
ccagtttagt agctttcatt                                              20

<210> SEQ ID NO 243
<211> LENGTH: 25
<212> TYPE: DNA
<213> ORGANISM: Artificial Sequence
<220> FEATURE:
<223> OTHER INFORMATION: Primer for amplification

<400> SEQUENCE: 243
gatttgttca acattaactc atcgg                                        25

<210> SEQ ID NO 244
<211> LENGTH: 20
<212> TYPE: DNA
<213> ORGANISM: Artificial Sequence
<220> FEATURE:
<223> OTHER INFORMATION: Primer for amplification

<400> SEQUENCE: 244
```
tgcgattaac agacaccctt                                              20

<210> SEQ ID NO 245
<211> LENGTH: 20
<212> TYPE: DNA
<213> ORGANISM: Artificial Sequence
<220> FEATURE:
<223> OTHER INFORMATION: Primer for amplification

<400> SEQUENCE: 245
tctcaggtgc tcacagaaca                                              20

<210> SEQ ID NO 246
<211> LENGTH: 20
<212> TYPE: DNA
<213> ORGANISM: Artificial Sequence
<220> FEATURE:
<223> OTHER INFORMATION: Primer for amplification

<400> SEQUENCE: 246
tatggaagag gcgctactgc                                              20

<210> SEQ ID NO 247
<211> LENGTH: 20
<212> TYPE: DNA
<213> ORGANISM: Artificial Sequence
<220> FEATURE:
<223> OTHER INFORMATION: Primer for amplification

<400> SEQUENCE: 247
cgacctgctg cataaacacc                                              20

<210> SEQ ID NO 248
<211> LENGTH: 20
<212> TYPE: DNA
<213> ORGANISM: Artificial Sequence
<220> FEATURE:
<223> OTHER INFORMATION: Primer for amplification

<400> SEQUENCE: 248
tgaacgctaa ggtgattgca                                              20

<210> SEQ ID NO 249
<211> LENGTH: 20
<212> TYPE: DNA
<213> ORGANISM: Artificial Sequence
<220> FEATURE:
<223> OTHER INFORMATION: Primer for amplification

<400> SEQUENCE: 249
acgtagacaa gagctcgcaa                                              20

<210> SEQ ID NO 250
<211> LENGTH: 20
<212> TYPE: DNA
<213> ORGANISM: Artificial Sequence
<220> FEATURE:
<223> OTHER INFORMATION: Primer for amplification

<400> SEQUENCE: 250
catcacgtac gactgcgtcg                                              20

<210> SEQ ID NO 251
<211> LENGTH: 19
<212> TYPE: DNA

```
<213> ORGANISM: Artificial Sequence
<220> FEATURE:
<223> OTHER INFORMATION: Primer for amplification

<400> SEQUENCE: 251
tgcaactttg tgctgagca                                                   19

<210> SEQ ID NO 252
<211> LENGTH: 20
<212> TYPE: DNA
<213> ORGANISM: Artificial Sequence
<220> FEATURE:
<223> OTHER INFORMATION: Primer for amplification

<400> SEQUENCE: 252
tatcgcttcc gggcattgtc                                                  20

<210> SEQ ID NO 253
<211> LENGTH: 25
<212> TYPE: DNA
<213> ORGANISM: Artificial Sequence
<220> FEATURE:
<223> OTHER INFORMATION: Primer for amplification

<400> SEQUENCE: 253
aaatcgatct cgtcaaattt cagac                                            25

<210> SEQ ID NO 254
<211> LENGTH: 20
<212> TYPE: DNA
<213> ORGANISM: Artificial Sequence
<220> FEATURE:
<223> OTHER INFORMATION: Primer for amplification

<400> SEQUENCE: 254
aggaaccaca aatcgccata                                                  20

<210> SEQ ID NO 255
<211> LENGTH: 20
<212> TYPE: DNA
<213> ORGANISM: Artificial Sequence
<220> FEATURE:
<223> OTHER INFORMATION: Primer for amplification

<400> SEQUENCE: 255
gacgtgaaga ttactacgct                                                  20

<210> SEQ ID NO 256
<211> LENGTH: 20
<212> TYPE: DNA
<213> ORGANISM: Artificial Sequence
<220> FEATURE:
<223> OTHER INFORMATION: Primer for amplification

<400> SEQUENCE: 256
agttcaatgc tgaaccacac                                                  20

<210> SEQ ID NO 257
<211> LENGTH: 25
<212> TYPE: DNA
<213> ORGANISM: Artificial Sequence
<220> FEATURE:
<223> OTHER INFORMATION: Primer for amplification

<400> SEQUENCE: 257
tagccgcgac cacggtaaga aggag                                            25
```

<210> SEQ ID NO 258
<211> LENGTH: 20
<212> TYPE: DNA
<213> ORGANISM: Artificial Sequence
<220> FEATURE:
<223> OTHER INFORMATION: Primer for amplification

<400> SEQUENCE: 258
cagcgcatca cccggaaaca                                               20

<210> SEQ ID NO 259
<211> LENGTH: 20
<212> TYPE: DNA
<213> ORGANISM: Artificial Sequence
<220> FEATURE:
<223> OTHER INFORMATION: Primer for amplification

<400> SEQUENCE: 259
atcgtgatca ttaacctgat                                               20

<210> SEQ ID NO 260
<211> LENGTH: 20
<212> TYPE: DNA
<213> ORGANISM: Artificial Sequence
<220> FEATURE:
<223> OTHER INFORMATION: Primer for amplification

<400> SEQUENCE: 260
ttaccctgat aaattaccgc                                               20

<210> SEQ ID NO 261
<211> LENGTH: 20
<212> TYPE: DNA
<213> ORGANISM: Artificial Sequence
<220> FEATURE:
<223> OTHER INFORMATION: Primer for amplification

<400> SEQUENCE: 261
ccatccgttg aatgagtttt                                               20

<210> SEQ ID NO 262
<211> LENGTH: 20
<212> TYPE: DNA
<213> ORGANISM: Artificial Sequence
<220> FEATURE:
<223> OTHER INFORMATION: Primer for amplification

<400> SEQUENCE: 262
tggtgttaac tggcaaaatc                                               20

<210> SEQ ID NO 263
<211> LENGTH: 20
<212> TYPE: DNA
<213> ORGANISM: Artificial Sequence
<220> FEATURE:
<223> OTHER INFORMATION: Primer for amplification

<400> SEQUENCE: 263
gtgacttcca acggcaaaag                                               20

<210> SEQ ID NO 264
<211> LENGTH: 20
<212> TYPE: DNA
<213> ORGANISM: Artificial Sequence
<220> FEATURE:

<223> OTHER INFORMATION: Primer for amplification

<400> SEQUENCE: 264
ccgttggttt gatagcaata                                       20

<210> SEQ ID NO 265
<211> LENGTH: 20
<212> TYPE: DNA
<213> ORGANISM: Artificial Sequence
<220> FEATURE:
<223> OTHER INFORMATION: Primer for amplification

<400> SEQUENCE: 265
gaatctggtg tatatggcga                                       20

<210> SEQ ID NO 266
<211> LENGTH: 20
<212> TYPE: DNA
<213> ORGANISM: Artificial Sequence
<220> FEATURE:
<223> OTHER INFORMATION: Primer for amplification

<400> SEQUENCE: 266
tcttcgctat tacgccagct                                       20

<210> SEQ ID NO 267
<211> LENGTH: 20
<212> TYPE: DNA
<213> ORGANISM: Artificial Sequence
<220> FEATURE:
<223> OTHER INFORMATION: Primer for amplification

<400> SEQUENCE: 267
cgtcagcgga tgtatctggt                                       20

<210> SEQ ID NO 268
<211> LENGTH: 20
<212> TYPE: DNA
<213> ORGANISM: Artificial Sequence
<220> FEATURE:
<223> OTHER INFORMATION: Primer for amplification

<400> SEQUENCE: 268
gcggaatttc tggttcgtaa                                       20

<210> SEQ ID NO 269
<211> LENGTH: 20
<212> TYPE: DNA
<213> ORGANISM: Artificial Sequence
<220> FEATURE:
<223> OTHER INFORMATION: Primer for amplification

<400> SEQUENCE: 269
ttgtcaacga tggggtcatg                                       20

<210> SEQ ID NO 270
<211> LENGTH: 20
<212> TYPE: DNA
<213> ORGANISM: Artificial Sequence
<220> FEATURE:
<223> OTHER INFORMATION: Primer for amplification

<400> SEQUENCE: 270
aaaaatgccg acataacgtc                                       20

<210> SEQ ID NO 271
<211> LENGTH: 20
<212> TYPE: DNA
<213> ORGANISM: Artificial Sequence
<220> FEATURE:
<223> OTHER INFORMATION: Primer for amplification

<400> SEQUENCE: 271
tctcaaagcg cgcaagttcg                                           20

<210> SEQ ID NO 272
<211> LENGTH: 24
<212> TYPE: DNA
<213> ORGANISM: Artificial Sequence
<220> FEATURE:
<223> OTHER INFORMATION: Primer for amplification

<400> SEQUENCE: 272
ggtattgatg taccgggtga gatt                                      24

<210> SEQ ID NO 273
<211> LENGTH: 20
<212> TYPE: DNA
<213> ORGANISM: Artificial Sequence
<220> FEATURE:
<223> OTHER INFORMATION: Primer for amplification

<400> SEQUENCE: 273
tcgacagaac gacaccaaat                                           20

<210> SEQ ID NO 274
<211> LENGTH: 20
<212> TYPE: DNA
<213> ORGANISM: Artificial Sequence
<220> FEATURE:
<223> OTHER INFORMATION: Primer for amplification

<400> SEQUENCE: 274
cactgtgaac gaaggatcgt                                           20

<210> SEQ ID NO 275
<211> LENGTH: 20
<212> TYPE: DNA
<213> ORGANISM: Artificial Sequence
<220> FEATURE:
<223> OTHER INFORMATION: Primer for amplification

<400> SEQUENCE: 275
tgttggcaat attgatgaag                                           20

<210> SEQ ID NO 276
<211> LENGTH: 20
<212> TYPE: DNA
<213> ORGANISM: Artificial Sequence
<220> FEATURE:
<223> OTHER INFORMATION: Primer for amplification

<400> SEQUENCE: 276
gacatcgctt tcaacattgg                                           20

<210> SEQ ID NO 277
<211> LENGTH: 20
<212> TYPE: DNA
<213> ORGANISM: Artificial Sequence
<220> FEATURE:
<223> OTHER INFORMATION: Primer for amplification

<400> SEQUENCE: 277
gacagacagg cgaactgacg                                               20

<210> SEQ ID NO 278
<211> LENGTH: 20
<212> TYPE: DNA
<213> ORGANISM: Artificial Sequence
<220> FEATURE:
<223> OTHER INFORMATION: Primer for amplification

<400> SEQUENCE: 278
gcgcagattt gcagattcgt                                               20

<210> SEQ ID NO 279
<211> LENGTH: 20
<212> TYPE: DNA
<213> ORGANISM: Artificial Sequence
<220> FEATURE:
<223> OTHER INFORMATION: Primer for amplification

<400> SEQUENCE: 279
tggcggcagt gaagagaagc                                               20

<210> SEQ ID NO 280
<211> LENGTH: 20
<212> TYPE: DNA
<213> ORGANISM: Artificial Sequence
<220> FEATURE:
<223> OTHER INFORMATION: Primer for amplification

<400> SEQUENCE: 280
gcaataacgc gctcgtaatc                                               20

<210> SEQ ID NO 281
<211> LENGTH: 20
<212> TYPE: DNA
<213> ORGANISM: Artificial Sequence
<220> FEATURE:
<223> OTHER INFORMATION: Primer for amplification

<400> SEQUENCE: 281
acaaagcagg ataagtcgca                                               20

<210> SEQ ID NO 282
<211> LENGTH: 20
<212> TYPE: DNA
<213> ORGANISM: Artificial Sequence
<220> FEATURE:
<223> OTHER INFORMATION: Primer for amplification

<400> SEQUENCE: 282
cacttcaggt aaggctgtga                                               20

<210> SEQ ID NO 283
<211> LENGTH: 25
<212> TYPE: DNA
<213> ORGANISM: Artificial Sequence
<220> FEATURE:
<223> OTHER INFORMATION: Primer for amplification

<400> SEQUENCE: 283
cagagaactg cgtaagtatt acgca                                         25

<210> SEQ ID NO 284
<211> LENGTH: 25

```
<212> TYPE: DNA
<213> ORGANISM: Artificial Sequence
<220> FEATURE:
<223> OTHER INFORMATION: Primer for amplification

<400> SEQUENCE: 284
tagtggtaac aagcgtgaaa aacaa                                               25

<210> SEQ ID NO 285
<211> LENGTH: 25
<212> TYPE: DNA
<213> ORGANISM: Artificial Sequence
<220> FEATURE:
<223> OTHER INFORMATION: Primer for amplification

<400> SEQUENCE: 285
atgaagactc cgtaaacgtt tcccc                                               25

<210> SEQ ID NO 286
<211> LENGTH: 25
<212> TYPE: DNA
<213> ORGANISM: Artificial Sequence
<220> FEATURE:
<223> OTHER INFORMATION: Primer for amplification

<400> SEQUENCE: 286
caaaaataga cacaccggga gttca                                               25

<210> SEQ ID NO 287
<211> LENGTH: 939
<212> TYPE: DNA
<213> ORGANISM: Lactococcus lactis

<400> SEQUENCE: 287
atgagaatta caattgccgg tgcaggagcg atggggagtc gttttggttt aatgcttcat         60
aaaggtggca atgaagtaac ccttatagat ggatggcctg aacacgttaa agcgattaaa        120
gagcatggtt tgcgagctaa ttacaatgga gaagaactca ccgctcatct atcggttgag        180
ttacaatctg agatttcttc taaagaaaaa acagatttaa ttattttgtt tacaaaagcc        240
atgcaattag ataagatgct acaagatatt aaaccattaa ttgacgagca taccaaggta        300
ctttgcttac taaatggaat tggtcacgaa gatactatag aaaaatatgt ttcgaaaaat        360
aatatctttta ttggtaatac tatgtggact gctggattga aggtccagg taaagctaaa        420
ttatttggtg atggttcggt tgagctacaa aatcttattt caggtgagga agaaacagct        480
aaaaagttag cagaaatatt atcagaatcg ggactgaatg ctaaatattc taacaatatt        540
cattattcta tttatagaaa agcttgtgtt aatggaacaa tgaatgggct ttgtactatt        600
ttagacacta tatggccgg attaggtgaa acaaaaccag cacatgatat ggttgttact        660
attgttaatg aatttgcagc agtagcaaaa tttgagaatg taaaccttga tattgctgaa        720
gtagttcagc acgttgaaac atgttttgat ccatctacaa ttggattaca ttacccttct        780
atgtatcagg atttgattaa aaataatcga ttgacagaga ttgactatat taatgggggct        840
gtttcacgta aagtaaaaaa atataatgta gccacacctt attgtgattt cttaacacaa        900
ttagttcaca gcaagaaga gttattaaaa gcaaaataa                                939

<210> SEQ ID NO 288
<211> LENGTH: 312
<212> TYPE: PRT
<213> ORGANISM: Lactococcus lactis
```

```
<400> SEQUENCE: 288

Met Arg Ile Thr Ile Ala Gly Ala Gly Ala Met Gly Ser Arg Phe Gly
1               5                   10                  15

Leu Met Leu His Lys Gly Gly Asn Glu Val Thr Leu Ile Asp Gly Trp
            20                  25                  30

Pro Glu His Val Lys Ala Ile Lys Glu His Gly Leu Arg Ala Asn Tyr
        35                  40                  45

Asn Gly Glu Glu Leu Thr Ala His Leu Ser Val Glu Leu Gln Ser Glu
    50                  55                  60

Ile Ser Ser Lys Glu Lys Thr Asp Leu Ile Ile Leu Phe Thr Lys Ala
65                  70                  75                  80

Met Gln Leu Asp Lys Met Leu Gln Asp Ile Lys Pro Leu Ile Asp Glu
                85                  90                  95

His Thr Lys Val Leu Cys Leu Leu Asn Gly Ile Gly His Glu Asp Thr
            100                 105                 110

Ile Glu Lys Tyr Val Ser Lys Asn Asn Ile Phe Ile Gly Asn Thr Met
            115                 120                 125

Trp Thr Ala Gly Leu Glu Gly Pro Gly Lys Ala Lys Leu Phe Gly Asp
130                 135                 140

Gly Ser Val Glu Leu Gln Asn Leu Ile Ser Gly Glu Glu Glu Thr Ala
145                 150                 155                 160

Lys Lys Leu Ala Glu Ile Leu Ser Glu Ser Gly Leu Asn Ala Lys Tyr
                165                 170                 175

Ser Asn Asn Ile His Tyr Ser Ile Tyr Arg Lys Ala Cys Val Asn Gly
            180                 185                 190

Thr Met Asn Gly Leu Cys Thr Ile Leu Asp Thr Asn Met Ala Gly Leu
        195                 200                 205

Gly Glu Thr Lys Pro Ala His Asp Met Val Val Thr Ile Val Asn Glu
        210                 215                 220

Phe Ala Ala Val Ala Lys Phe Glu Asn Val Asn Leu Asp Ile Ala Glu
225                 230                 235                 240

Val Val Gln His Val Glu Thr Cys Phe Asp Pro Ser Thr Ile Gly Leu
                245                 250                 255

His Tyr Pro Ser Met Tyr Gln Asp Leu Ile Lys Asn Asn Arg Leu Thr
            260                 265                 270

Glu Ile Asp Tyr Ile Asn Gly Ala Val Ser Arg Lys Gly Lys Lys Tyr
        275                 280                 285

Asn Val Ala Thr Pro Tyr Cys Asp Phe Leu Thr Gln Leu Val His Ser
    290                 295                 300

Lys Glu Glu Leu Leu Lys Ala Lys
305                 310
```